(12) United States Patent
Pyo et al.

(10) Patent No.: US 11,522,136 B2
(45) Date of Patent: Dec. 6, 2022

(54) ORGANIC LIGHT-EMITTING DIODE WITH HIGH EFFICIENCY

(71) Applicant: SFC CO., LTD., Cheongju (KR)

(72) Inventors: Sung-Wan Pyo, Daejeon (KR); So Young Shim, Daejeon (KR); Yun-Ah Lee, Suwon (KR); Se Jin Yu, Gyeongsan (KR)

(73) Assignee: SFC CO., LTD., Cheongju (KR)

( * ) Notice: Subject to any disclaimer, the term of this patent is extended or adjusted under 35 U.S.C. 154(b) by 862 days.

(21) Appl. No.: 15/334,772

(22) Filed: Oct. 26, 2016

(65) Prior Publication Data

US 2017/0141321 A1 May 18, 2017

(30) Foreign Application Priority Data

Nov. 12, 2015 (KR) ........................ 10-2015-0158590

(51) Int. Cl.
| | | |
|---|---|---|
| *H01L 51/00* | (2006.01) | |
| *C07D 307/91* | (2006.01) | |
| *C07D 307/94* | (2006.01) | |
| *C07D 493/10* | (2006.01) | |
| *C09K 11/02* | (2006.01) | |
| *C09K 11/06* | (2006.01) | |
| *H01L 51/50* | (2006.01) | |

(52) U.S. Cl.
CPC ........ *H01L 51/0061* (2013.01); *C07D 307/91* (2013.01); *C07D 307/94* (2013.01); *C07D 493/10* (2013.01); *C09K 11/025* (2013.01); *C09K 11/06* (2013.01); *H01L 51/006* (2013.01); *C09K 2211/1007* (2013.01); *C09K 2211/1014* (2013.01); *C09K 2211/1088* (2013.01); *H01L 51/0058* (2013.01); *H01L 51/0073* (2013.01); *H01L 51/5012* (2013.01); *H01L 51/5096* (2013.01)

(58) Field of Classification Search
CPC ... C07C 211/54; C07C 211/55; C07C 211/60; C07D 307/77; C07D 307/91; C07D 405/14; C09K 2211/1011; H01L 51/0059; H01L 51/0072; H01L 51/0073; H01L 51/0074
See application file for complete search history.

(56) References Cited

U.S. PATENT DOCUMENTS

2016/0351818 A1* 12/2016 Kim ................... C09K 11/06

FOREIGN PATENT DOCUMENTS

| KR | 10-2008-0015865 | 2/2008 |
| KR | 10-2012-0047706 | 5/2012 |
| KR | 10-1555155 | 9/2015 |
| KR | 10-2015-0116337 | 10/2015 |

* cited by examiner

*Primary Examiner* — Sean M DeGuire
(74) *Attorney, Agent, or Firm* — STIP Law Group, LLC

(57) ABSTRACT

Disclosed herein is an organic light-emitting diode, comprising: a first electrode; a second electrode facing the first electrode; and an electron-blocking layer and a light-emitting layer sequentially interposed between the first electrode and the second electrode, wherein the light-emitting layer comprises at least one of the amine compounds represented by the following Chemical Formula A or B, and the electron-blocking layer comprises the compound represented by the following Chemical Formula C. Chemical Formulas A, B and C are as described in the Specification.

13 Claims, 1 Drawing Sheet

| 80 |
|----|
| 70 |
| 60 |
| 50 |
| 40 |
| 30 |
| 20 |
| 10 |

ORGANIC LIGHT-EMITTING DIODE WITH HIGH EFFICIENCY

CROSS REFERENCE TO RELATED APPLICATION(S)

This application claims priority to and incorporates herein by reference all disclosure in Korean Patent Application No. 10-2015-0158590 filed Nov. 12, 2015.

BACKGROUND OF THE INVENTION

1. Field of the Invention

The present disclosure relates to an organic light-emitting diode with high efficiency. More particularly, the present disclosure relates to an organic light-emitting diode having high efficiency wherein materials of specific structures for a dopant and an electron-blocking layer are used in a light-emitting layer.

2. Description of the Related Art

Organic light-emitting diodes (OLEDs), based on self-luminescence, are used to create digital displays having the advantage of being able to be made thinner and lighter than liquid crystal displays. In addition, an OLED display exhibits a much faster response time than an LCD. Accordingly, organic light-emitting diodes find applications in the illumination field as well as the full-color display field.

The materials used as organic layers in organic light-emitting diodes may be divided into luminescent materials and charge-carrying materials, for example, a hole injection material, a hole transport material, an electron injection material, and an electron transport material. As for the luminescent materials, there are two main families of OLED: those based on small molecules and those employing polymers.

Meanwhile, when a single material is employed as the luminescent material, intermolecular actions cause the maximum luminescence wavelength to shift toward a longer wavelength, resulting in a reduction in color purity and light emission efficiency. In this regard, a host-dopant system may be used as a luminescent material so as to increase the color purity and the light emission efficiency through energy transfer.

This is based on the principle whereby, when a dopant is smaller in energy band gap than a host accounting for the light-emitting layer, the addition of a small amount of the dopant to the host generates excitons from the light-emitting layer so that the excitons are transported to the dopant, emitting light at high efficiency. Here, light of desired wavelengths can be obtained depending on the kind of dopant because the wavelength of the host moves to the wavelength range of the dopant.

With regard to the related arts pertaining to dopant compounds in the light-emitting layer, reference may be made to Korean Unexamined Patent Application Publication No. 10-2008-0015865 (Feb. 20, 2008), which describes an organic light-emitting device using an arylamine-coupled indenofluorene derivative, and to Korean Unexamined Patent Application Publication No. 10-2012-0047706 (May 14, 2012), which describes an organic photoelectric device using a compound in which dibenzofuran or dibenzothiophene coexists with fluorene or carbazole.

Further, an electron-blocking layer or an auxiliary light-emitting layer may be interposed between a hole transport layer and a light-emitting layer in an organic light-emitting diode in order to bring about an improvement in luminous efficiency and luminance.

As a related art for an electron-blocking layer or auxiliary light-emitting layer, mention may be made of Korean Patent No. 10-1555155 (Sep. 22, 2015) and Korean Unexamined Patent Application Publication No. 10-2015-0116337 (Oct. 15, 2015) which respectively describe the availability of an amine compound having a bis(fluorenyl) group as a compound for an electron-blocking layer and the use of a carbazole derivative in an auxiliary light-emitting layer.

However, there is still a continued need to develop organic light-emitting diodes exhibiting higher efficiency.

RELATED ART DOCUMENT

Korean Unexamined Patent Application Publication No. 10-2008-0015865 (Feb. 20, 2008)
Korean Unexamined Patent Application Publication No. 10-2012-0047706 (May 14, 2012)
Korean Patent No. 10-1555155 (Sep. 22, 2015)
Korean Unexamined Patent Application Publication No. 10-2015-0116337 (Oct. 15, 2015)

SUMMARY OF THE INVENTION

Therefore, the present disclosure aims to provide a novel organic light-emitting diode (OLED) with high efficiency, wherein an appropriate material is introduced into a specific layer of an OLED.

In accordance with an aspect thereof, the present disclosure provides an organic light-emitting diode, comprising: a first electrode; a second electrode facing the first electrode; and an electron-blocking layer and a light-emitting layer interposed in that order between the first electrode and the second electrode, wherein the light-emitting layer comprises at least one of the amine compounds represented by the following Chemical Formula A or B, and the electron-blocking layer comprises the compound represented by the following Chemical Formula C:

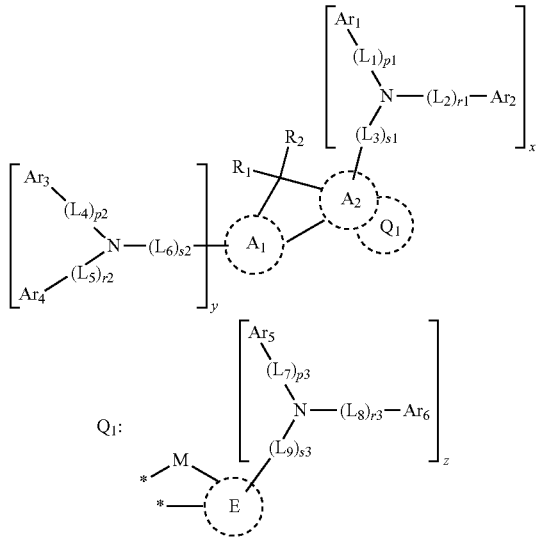

[Chemical Formula A]

[Chemical Formula B]

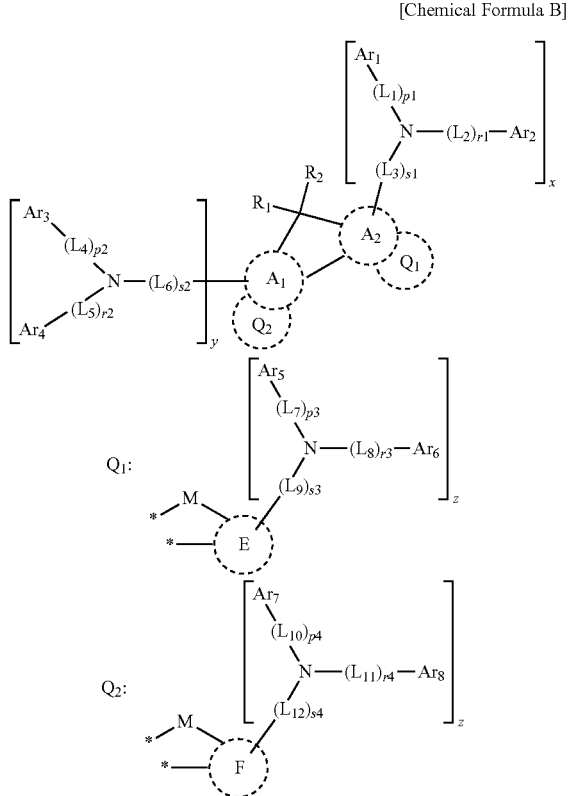

wherein, $A_1$, $A_2$, E, and F may be the same or different, and are each independently a substituted or unsubstituted aromatic hydrocarbon ring of 6 to 50 carbon atoms, or a substituted or unsubstituted heteroaromatic ring of 2 to 40 carbon atoms wherein two adjacent carbon atoms of the aromatic ring $A_1$ and two adjacent carbon atoms of the aromatic ring $A_2$ form a 5-membered fused ring together with a carbon atom to which the substituents $R_1$ and $R_2$ are bonded;

linkers $L_1$ to $L_{12}$ may be the same or different, and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from among N—$R_3$, $CR_4R_5$, $SiR_6R_7$, $GeR_8R_9$, O, S, and Se;

$R_1$ to $R_9$, and $Ar_1$ to $Ar_8$ may be the same or different, and are each independently any one selected from among hydrogen, deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkylgermanium of 1 to 30 carbon atoms, a substituted or unsubstituted arylgermanium of 6 to 30 carbon atoms, a cyano, a nitro, and a halogen, with the proviso that $R_1$ and $R_2$ together may form a mono- or polycyclic aliphatic or aromatic ring, which may be a heterocyclic ring containing a heteroatom selected from among N, O, P, Si, S, Ge, Se, and Te as a ring member;

p1 to p4, r1 to r4, and s1 to s4 are each independently an integer of 1 to 3, with the proviso that when any of them is 2 or greater, the corresponding linkers may be the same or different, x is an integer of 1 or 2, and y and z may be the same or different, and are each independently an integer of 0 to 3; and $Ar_1$ may form a ring with $Ar_2$, $Ar_3$ may form a ring with $Ar_4$, $Ar_5$ may form a ring with $Ar_6$, and $Ar_7$ may form a ring with $Ar_8$, two adjacent carbon atoms of the $A_2$ ring moiety of Chemical Formula A may occupy respective positions * of Structural Formula $Q_1$ to form a fused ring, and two adjacent carbon atoms of the $A_1$ ring moiety of Chemical Formula B may occupy respective positions * of structural Formula $Q_2$ to form a fused ring,

[Chemical Formula C]

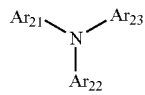

wherein, $Ar_{21}$ to $Ar_{23}$ may be the same or different and are each independently selected from among a substituted or unsubstituted aryl of 6 to 50 carbon atoms, a substituted or unsubstituted heteroaryl of 3 to 50 carbon atoms containing O, N or S as a heteroatom, and a compound represented by the following Structural Formula A, with the proviso that at least one of $Ar_{21}$ to $Ar_{23}$ is the compound of Structural Formula A:

[Structural Formula A]

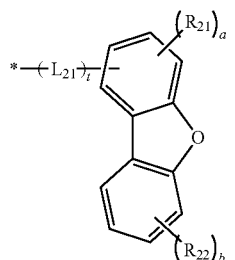

wherein, $L_{21}$ is selected from among a single bond, a substituted or unsubstituted alkylene of 1 to 30 carbon atoms, a substituted or unsubstituted cycloalkylene of 3 to 30 carbon atoms, a substituted or unsubstituted aryl of 6 to 50 carbon atoms, and a substituted or unsubstituted heteroaryl of 3 to 50 carbon atoms containing O, N or S as a heteroatom;

t is an integer of 1 to 3, with the proviso that when it is 2 or greater, the corresponding $L_{21}$'s may be the same or different, $R_{21}$ and $R_{22}$ may be the same or different, and are each independently selected from the group consisting of hydrogen, deuterium, a substituted or unsubstituted alkyl of 1 to 30 carbon atoms, a substituted or unsubstituted alkenyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 3 to 50 carbon atoms containing O, N or S as a heteroatom, a substituted or unsubstituted silicone, a substituted or unsubstituted boron, a substituted or unsubstituted silane, a carbonyl, a phosphoryl, an amino, a nitrile, a hydroxyl, a nitro, a halogen, an amide, and an ester;

a is an integer of 0 to 3, and b is an integer of 0 to 4, with the proviso that when a and b are each 2 or greater, the corresponding $R_{21}$'s and $R_{22}$'s are the same or different, wherein the term 'substituted' in the expression 'substituted or unsubstituted' for Chemical Formulas A, B and C means having at least one substituent selected from the group consisting of a deuterium, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a hetero arylamino of 1 to 24 carbon atoms, an alkylsilyl of 1 to 24 carbon atoms, an arylsilyl of 6 to 24 carbon atoms, and an aryloxy of 1 to 24 carbon atoms.

BREW DESCRIPTION OF THE DRAWINGS

The above and other objects, features and advantages of the present disclosure will be more clearly understood from the following detailed description taken in conjunction with the accompanying drawing, in which:

FIGURE is a schematic cross-sectional view of the structure of an organic light-emitting diode according to some embodiments of the present disclosure.

DESCRIPTION OF THE PREFERRED EMBODIMENTS

Hereinafter, some embodiments which can be easily embodied by those skilled in the art will be described with reference to the accompanying drawings. In the drawings of the invention, the sizes and dimensions of structures are illustrated by enlarging or reducing them relative to the actual sizes and dimensions to clarify the invention, the known configurations are not illustrated in order to emphasize characteristic configurations, and the invention is not limited to the drawings. In describing the phenomena of the preferred embodiments of the invention in detail, when it is determined that a detailed description of related known functions or configurations may unnecessarily obscure the gist of the invention, such a detailed description is omitted.

In addition, the size and thickness of each configuration illustrated in the drawings are arbitrarily illustrated for the sake of convenience of explanation, and thus the present disclosure may not be necessarily limited to what is shown in the illustration. Further, in the drawings, the thicknesses of layers and regions may be exaggerated for clarity. It will be understood that when an element such as a layer, film, region or substrate is referred to as being "on" another element, it may be directly on the other element or intervening elements may also be present.

Throughout the specification, when a portion may "include" a certain constituent element, unless specified otherwise, it may not be construed to exclude another constituent element but may be construed to further include other constituent elements.

In addition, unless explicitly described to the contrary, the word "comprise" and variations such as "comprises" or "comprising" will be understood to imply the inclusion of stated elements but not the exclusion of any other elements. Further, throughout the specification, the word "on" means positioning on or below the object portion, but does not essentially mean positioning on the lower side of the object portion based on a direction of gravity.

The present disclosure addresses an organic light-emitting diode, comprising: a first electrode; a second electrode facing the first electrode; and an electron-blocking layer and a light-emitting layer interposed in that order between the first electrode and the second electrode, wherein the light-emitting layer comprises at least one of the amine compounds represented by the following Chemical Formula A or B, and the electron-blocking layer comprises the compound represented by the following Chemical Formula C:

[Chemical Formula A]

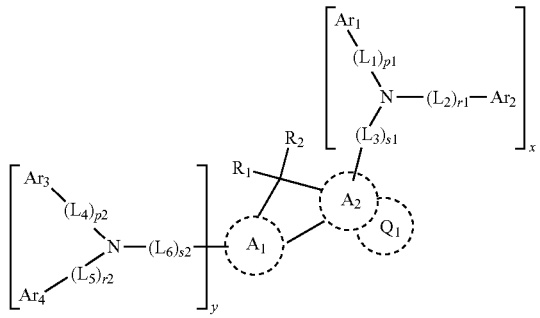

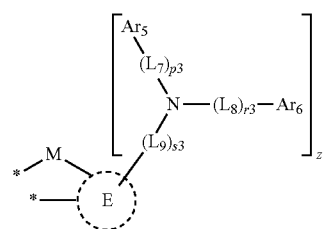

-continued

[Chemical Formula B]

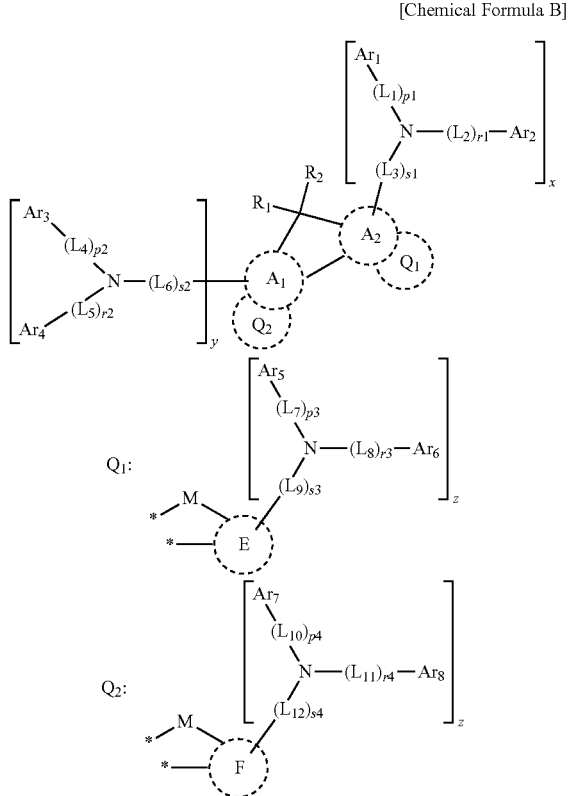

wherein, $A_1$, $A_2$, E, and F may be the same or different, and are each independently a substituted or unsubstituted aromatic hydrocarbon ring of 6 to 50 carbon atoms, or a substituted or unsubstituted heteroaromatic ring of 2 to 40 carbon atoms wherein two adjacent carbon atoms of the aromatic ring $A_1$ and two adjacent carbon atoms of the aromatic ring $A_2$ form a 5-membered fused ring together with a carbon atom to which substituents $R_1$ and $R_2$ are bonded;

linkers $L_1$ to $L_{12}$ may be the same or different, and are each independently selected from among a direct bond, a substituted or unsubstituted alkylene of 1 to 60 carbon atoms, a substituted or unsubstituted alkenylene of 2 to 60 carbon atoms, a substituted or unsubstituted alkynylene of 2 to 60 carbon atoms, a substituted or unsubstituted cycloalkylene of 3 to 60 carbon atoms, a substituted or unsubstituted heterocycloalkylene of 2 to 60 carbon atoms, a substituted or unsubstituted arylene of 6 to 60 carbon atoms, and a substituted or unsubstituted heteroarylene of 2 to 60 carbon atoms;

M is any one selected from among N—$R_3$, $CR_4R_5$, $SiR_6R_7$, $GeR_8R_9$, O, S, and Se;

$R_1$ to $R_9$, and $Ar_1$ to $Ar_8$ may be the same or different, and are each independently any one selected from among hydrogen, deuterium, a substituted or unsubstituted alkyl of 1 to 30 carbon atoms, a substituted or unsubstituted aryl of 6 to 50 carbon atoms, a substituted or unsubstituted alkenyl of 2 to 30 carbon atoms, a substituted or unsubstituted alkynyl of 2 to 20 carbon atoms, a substituted or unsubstituted cycloalkyl of 3 to 30 carbon atoms, a substituted or unsubstituted cycloalkenyl of 5 to 30 carbon atoms, a substituted or unsubstituted heteroaryl of 2 to 50 carbon atoms, a substituted or unsubstituted heterocycloalkyl of 2 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted alkylsilyl of 1 to 30 carbon atoms, a substituted or unsubstituted arylsilyl of 6 to 30 carbon atoms, a substituted or unsubstituted alkyl germanium of 1 to 30 carbon atoms, a substituted or unsubstituted aryl germanium of 6 to 30 carbon atoms, a cyano, a nitro, and a halogen, with the proviso that $R_1$ and $R_2$ together may form a mono- or polycyclic aliphatic or aromatic ring, which may be a heterocyclic ring containing a heteroatom selected from among N, O, P, Si, S, Ge, Se, and Te as a ring member;

p1 to p4, r1 to r4, and s1 to s4 are each independently an integer of 1 to 3, with the proviso that when any of them is 2 or greater, the corresponding linkers may be the same or different, x is an integer of 1 or 2, and y and z may be the same or different and are each independently an integer of 0 to 3; and $Ar_1$ may form a ring with $Ar_2$, $Ar_3$ may form a ring with $Ar_4$, $Ar_5$ may form a ring with $Ar_6$, and $Ar_7$ may form a ring with $Ar_8$, two adjacent carbon atoms of the $A_2$ ring moiety of Chemical Formula A may occupy respective positions * of Structural Formula $Q_1$ to form a fused ring, two adjacent carbon atoms of the $A_1$ ring moiety of Chemical Formula B may occupy respective positions * of structural Formula $Q_2$ to form a fused ring,

[Chemical Formula C]

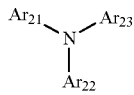

wherein, $Ar_{21}$ to $Ar_{23}$ may be the same or different and are each independently selected from among a substituted or unsubstituted aryl of 6 to 50 carbon atoms, a substituted or unsubstituted heteroaryl of 3 to 50 carbon atoms containing O, N or S as a heteroatom, and a compound represented by the following Structural Formula A, with the proviso that at least one of $Ar_{21}$ to $Ar_{23}$ is the compound of Structural Formula A:

[Structural Formula A]

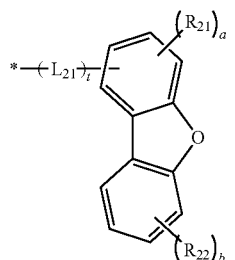

wherein, $L_{21}$ is selected from among a single bond, a substituted or unsubstituted alkylene of 1 to 30 carbon atoms, a substituted or unsubstituted cycloalkylene of 3 to 30 carbon atoms, a substituted or unsubstituted aryl of 6 to 50 carbon atoms, and a substituted or unsubstituted heteroaryl of 3 to 50 carbon atoms containing O, N or S as a heteroatom;

t is an integer of 1 to 3, with the proviso that when it is 2 or greater, the corresponding $L_{21}$'s may be the same or different, $R_{21}$ and $R_{22}$ may be the same or different, and are each independently selected from the group consisting of hydrogen, deuterium, a substituted or unsubstituted alkyl of 1 to 30 carbon atoms, a substituted or unsubstituted alkenyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 3 to 50 carbon atoms containing O, N or S as a heteroatom, a substituted or unsubstituted silicone, a substituted or unsubstituted boron, a substituted or unsubstituted silane, a carbonyl, a phosphoryl, an amino, a nitrile, a hydroxyl, a nitro, a halogen, an amide, and an ester; and a is an integer of 0 to 3, and b is an integer of 0 to 4, with the proviso that when a and b are each 2 or greater, the corresponding $R_{21}$'s and $R_{22}$'s are the same or different, wherein the term 'substituted' in the expression 'substituted or unsubstituted' for Chemical Formulas A, B and C means having at least one substituent selected from the group consisting of a deuterium, a cyano, a halogen, a hydroxy, a nitro, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkoxy of 1 to 24 carbon atoms, an alkylamino of 1 to 24 carbon atoms, an arylamino of 6 to 24 carbon atoms, a hetero arylamino of 1 to 24 carbon atoms, an alkylsilyl of 1 to 24 carbon atoms, an arylsilyl of 6 to 24 carbon atoms, and an aryloxy of 6 to 24 carbon atoms.

The expression indicating the number of carbon atoms such as in "a substituted or unsubstituted alkyl of 1 to 30 carbon atoms", "a substituted or unsubstituted aryl of 6 to 50 carbon atoms", etc. means the total number of carbon atoms of, for example, the alkyl or aryl radical or moiety alone, exclusive of the number of carbon atoms of the substituent. For instance, a phenyl group with a butyl at the para position falls within the scope of an aryl of 6 carbon atoms although it is substituted with a butyl radical of 4 carbon atoms.

As used herein, the term "aryl" means an organic radical, derived from an aromatic hydrocarbon by removing one hydrogen atom. Further, the aromatic system may include a fused ring that is formed by adjacent substituents on the aryl radical.

Examples of the aryl include phenyl, o-biphenyl, m-biphenyl, p-biphenyl, o-terphenyl, m-terphenyl, p-terphenyl, naphthyl, anthryl, phenanthryl, pyrenyl, indenyl, fluorenyl, tetrahydronaphthyl, perylenyl, chrysenyl, naphthacenyl, and fluoranthenyl, at least one hydrogen atom of which may be substituted by a deuterium atom, a halogen atom, a hydroxy, a nitro, a cyano, a silyl, an amino (—$NH_2$, —NH(R), —N(R')(R") wherein R' and R" are each independently an alkyl of 1 to 10 alkyl, in this case, called "alkylamino"), an amidino, a hydrazine, a hydrazone, a carboxyl, a sulfonic acid, a phosphoric acid, an alkyl of 1 to 24 carbon atoms, a halogenated alkyl of 1 to 24 carbon atoms, an alkenyl of 2 to 24 carbon atoms, an alkynyl of 2 to 24 carbon atoms, a heteroalkyl of 1 to 24 carbon atoms, an aryl of 6 to 24 carbon atoms, an arylalkyl of 7 to 24 carbon atoms, a heteroaryl of 2 to 24 carbon atoms, or a heteroarylalkyl of 2 to 24 carbon atoms.

The substituent heteroaryl used in the compound of the present disclosure refers to a cyclic aromatic system of 2 to 24 carbon atoms containing one to three heteroatoms selected from among N, O, P, Si, S, Ge, Se, and Te. In the aromatic system, two or more rings may be fused. One or more hydrogen atoms on the heteroaryl may be substituted by the same substituents as on the aryl.

As used herein, the term "heteroaromatic ring" refers to an aromatic hydrocarbon ring containing as a ring member at least one heteroatom selected from among N, O, P, Si, S, Ge, Se, and Te.

Examples of the substituent alkyl useful in the present disclosure include methyl, ethyl, propyl, isopropyl, isobutyl, sec-butyl, tert-butyl, pentyl, iso-amyl, and hexyl. At least one hydrogen atom of the alkyl may be substituted by the same substituent as in the aryl.

Examples of the substituent alkoxy useful in the present disclosure include methoxy, ethoxy, propoxy, isobutyloxy, sec-butyloxy, pentyloxy, iso-amyloxy, and hexyloxy. At least one hydrogen atom of the alkoxy may be substituted by the same substituent as in the aryl.

Representative among examples of the silyl useful in the present disclosure are trimethylsilyl, triethylsilyl, triphenylsilyl, trimethoxysilyl, dimethoxyphenylsilyl, diphenylmethylsilyl, diphenylvinylsilyl, methylcyclobutylsilyl, and dimethylfurylsilyl. One or more hydrogen atom of the silyl may be substituted by the same substituent as in the aryl.

As used herein, the expression "(the organic layer) . . . comprising at least one organic compound" is construed to mean that the organic layer may include one or two or more different compounds that fall within the scope of the present disclosure.

The amine compound represented by Chemical Formula A or B used in the organic light-emitting diode of the present disclosure is characterized by a structure in which the moiety of Chemical Formula $Q_1$ in Chemical Formula A is connected to the ring $A_1$ while an amine moiety containing both $Ar_1$ and $Ar_2$ is bonded to the ring $A_2$, or in which the moieties of Chemical Formulas $Q_2$ and $Q_1$ are respectively connected to the rings $A_1$ and $A_2$ while an amine moiety containing both $Ar_1$ and $Ar_2$ is bonded to the ring $A_2$.

In Chemical Formula A or B, $A_1$, $A_2$, E and F may be the same or different and are each independently a substituted or unsubstituted aromatic hydrocarbon ring of 6 to 50 carbon atoms.

When $A_1$, $A_2$, E, and F in Chemical Formula A or B may be the same or different and are each independently a substituted or unsubstituted aromatic hydrocarbon ring of 6 to 50 carbon atoms, the aromatic hydrocarbon ring moieties may each be independently any one selected from among [Structural Formula 10] to [Structural Formula 21].

[Structural Formula 10]

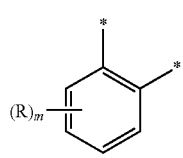

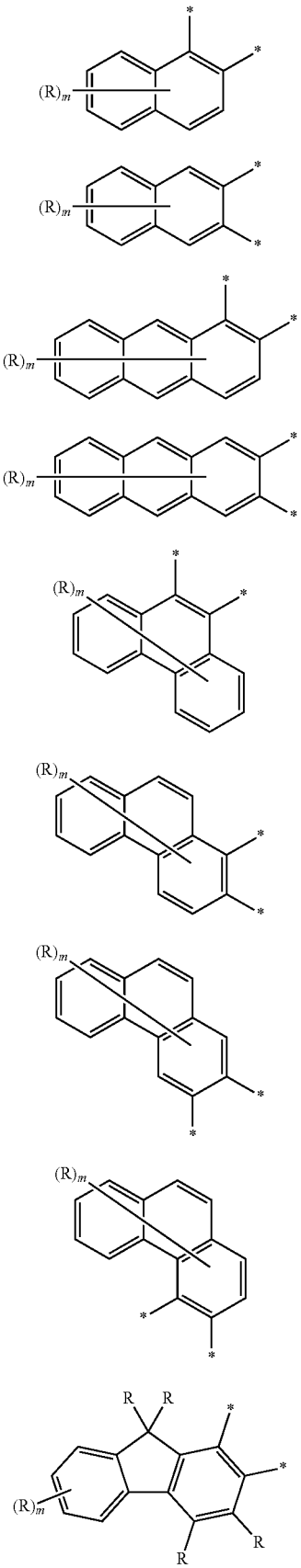

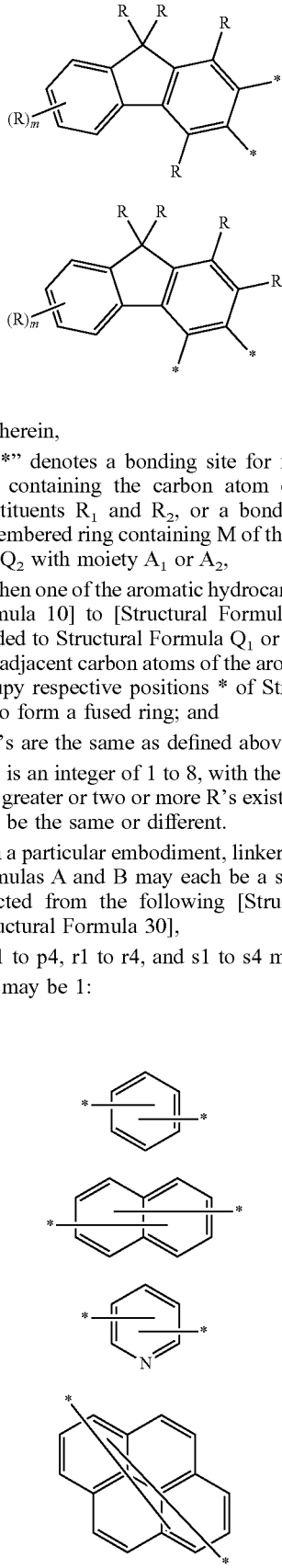

wherein,

"-*" denotes a bonding site for forming a 5-membered ring containing the carbon atom connected to both the substituents $R_1$ and $R_2$, or a bonding site for forming a 5-membered ring containing M of the structural Formula $Q_1$ and $Q_2$ with moiety $A_1$ or $A_2$, when one of the aromatic hydrocarbon rings of [Structural Formula 10] to [Structural Formula 21] for $A_1$ or $A_2$ is bonded to Structural Formula $Q_1$ or Structural Formula $Q_2$, two adjacent carbon atoms of the aromatic hydrocarbon ring occupy respective positions * of Structural Formula $Q_1$ or $Q_2$ to form a fused ring; and R's are the same as defined above for $R_1$ and $R_2$, m is an integer of 1 to 8, with the proviso that when m is 2 or greater or two or more R's exist, the corresponding R's may be the same or different.

In a particular embodiment, linkers $L_1$ to $L_{12}$ of Chemical Formulas A and B may each be a single bond, or any one selected from the following [Structural Formula 22] to [Structural Formula 30], p1 to p4, r1 to r4, and s1 to s4 may each be 1 or 2, and x may be 1:

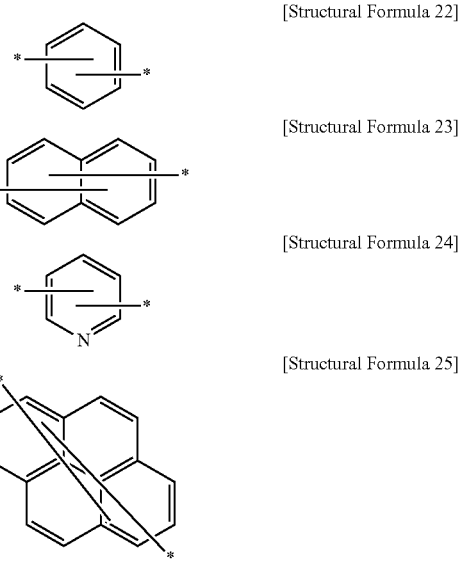

[Structural Formula 26]

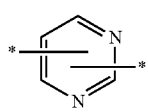

[Structural Formula 27]

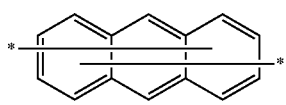

[Structural Formula 28]

[Structural Formula 29]

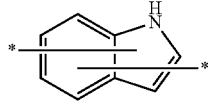

[Structural Formula 30]

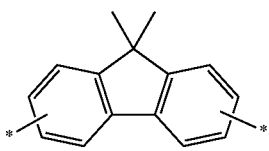

In the linker, each of the unsubstituted carbon atoms of the aromatic ring moiety is bound with a hydrogen atom or a deuterium atom.

In this case, x and y may each be 1, and z may be 0 or 1.

The amine compound represented by Chemical Formula A or B, useful in the organic light-emitting diode of the present disclosure, may be selected from compounds represented by the following [Chemical Formula 1] to [Chemical Formula 239], but is not limited thereto.

<Chemical Formula 1>

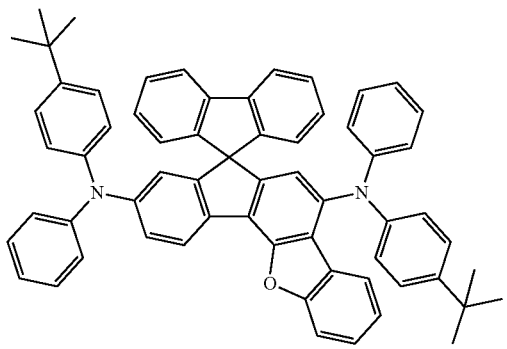

<Chemical Formula 2>

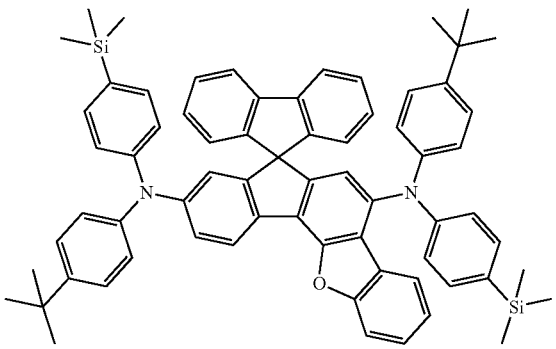

<Chemical Formula 3>

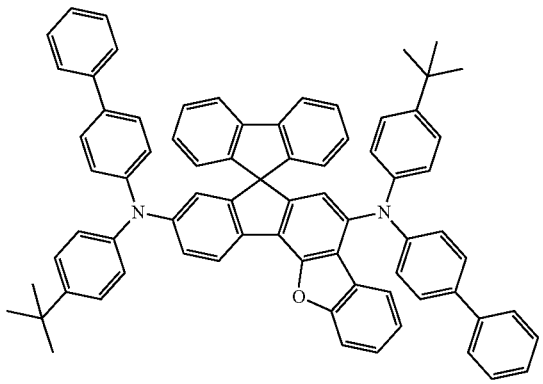

<Chemical Formula 4>

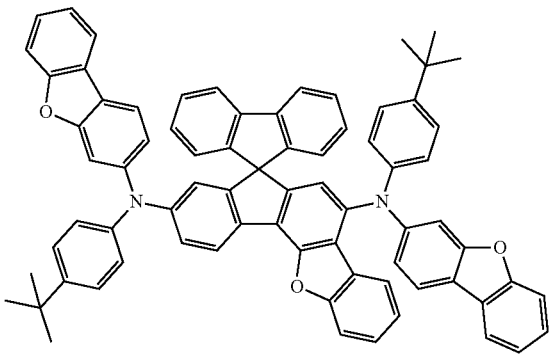

-continued
<Chemical Formula 5>
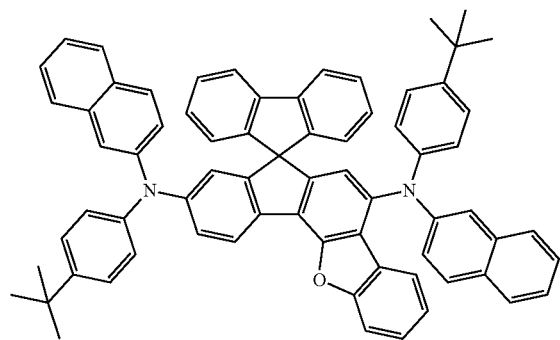
<Chemical Formula 6>
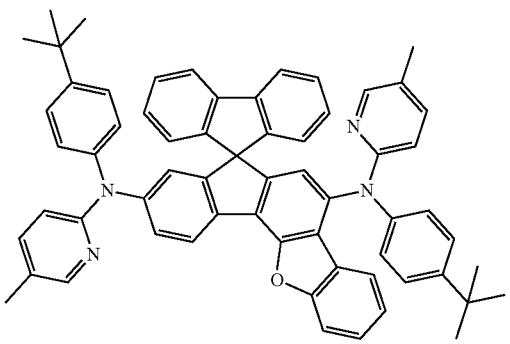
<Chemical Formula 7>
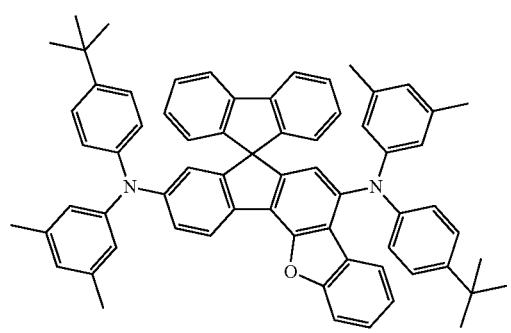
<Chemical Formula 8>
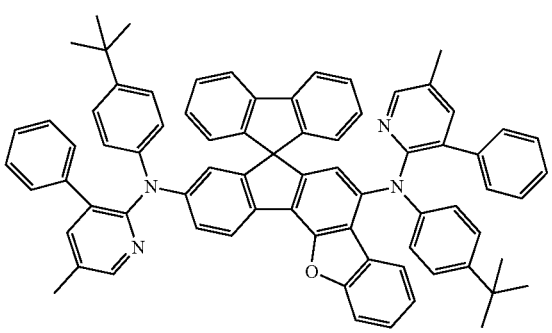
<Chemical Formula 9>
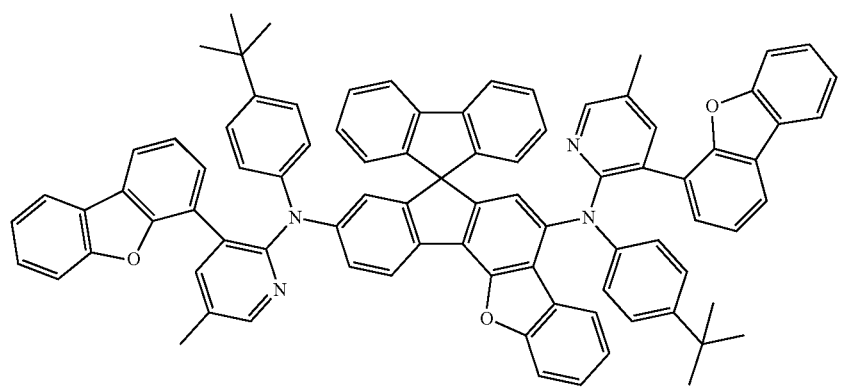
<Chemical Formula 10>
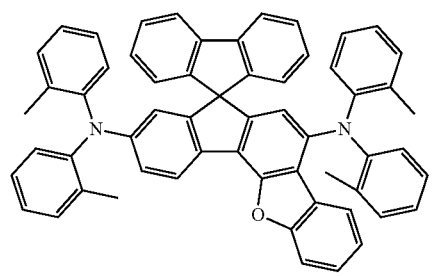
<Chemical Formula 11>
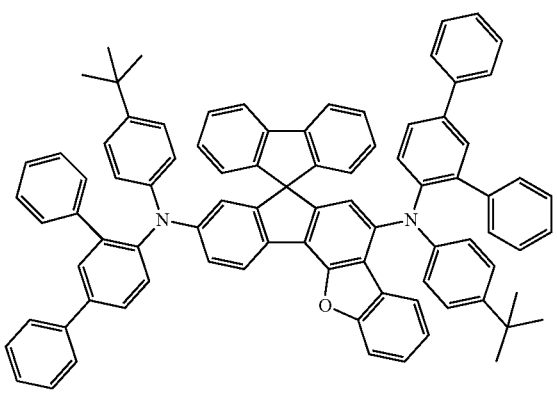

-continued
<Chemical Formula 12>
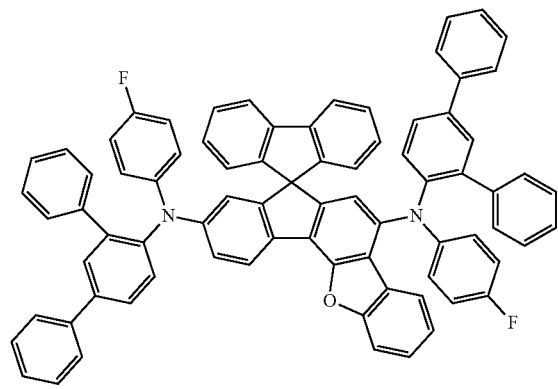
<Chemical Formula 13>
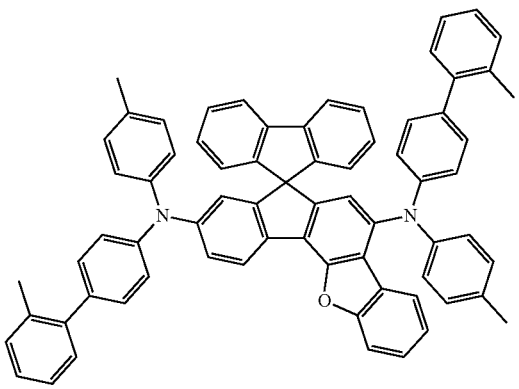
<Chemical Formula 14>
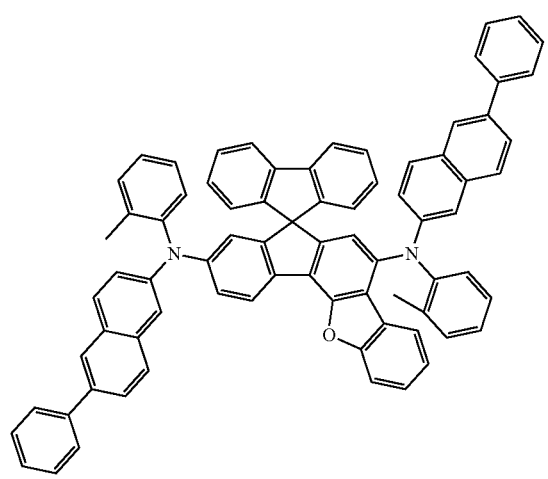
<Chemical Formula 15>
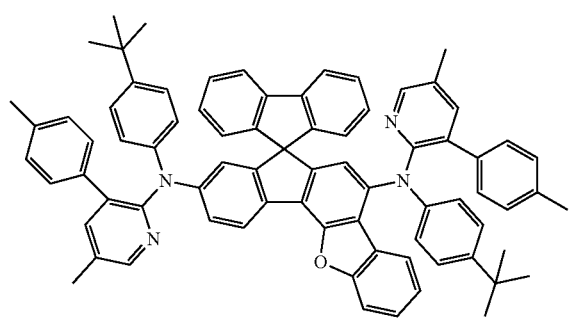
<Chemical Formula 16>
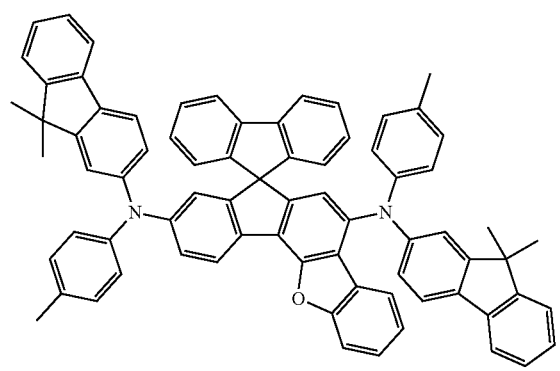
<Chemical Formula 17>
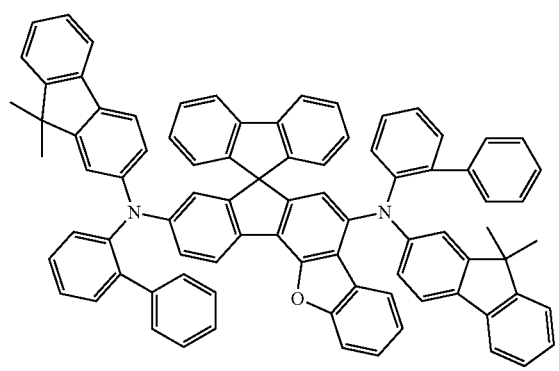
<Chemical Formula 18>
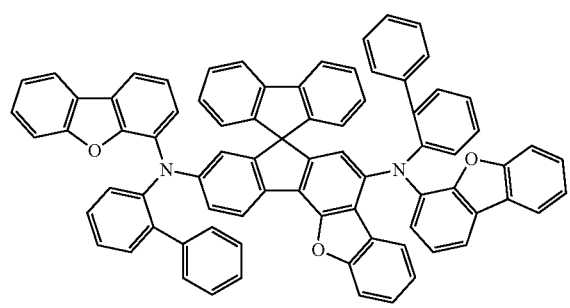
<Chemical Formula 19>
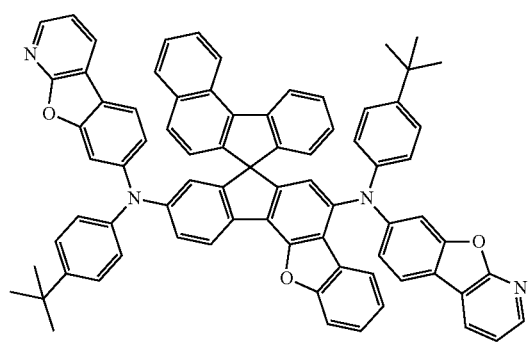

-continued
<Chemical Formula 20>
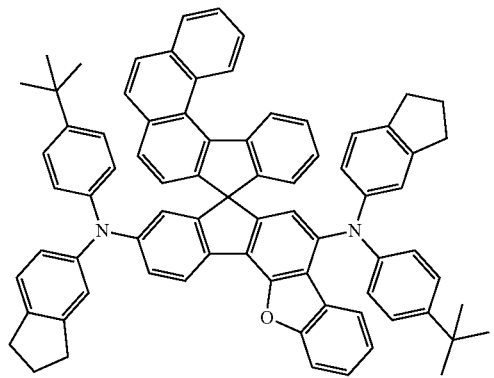
<Chemical Formula 21>
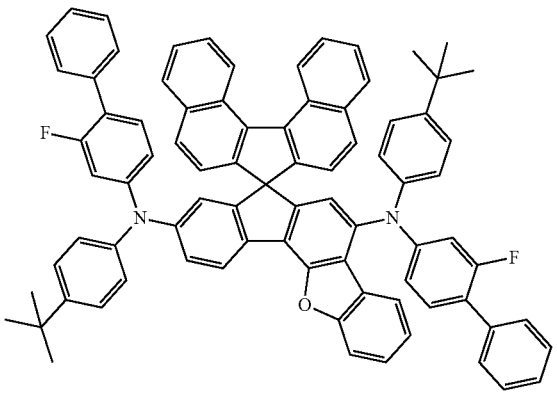
<Chemical Formula 22>
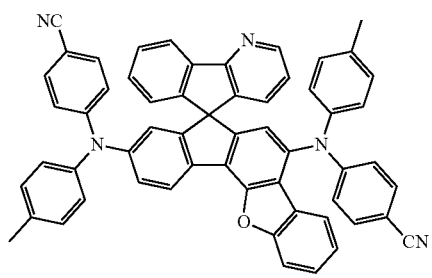
<Chemical Formula 23>
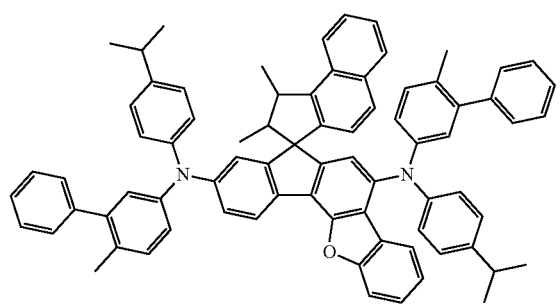
<Chemical Formula 24>
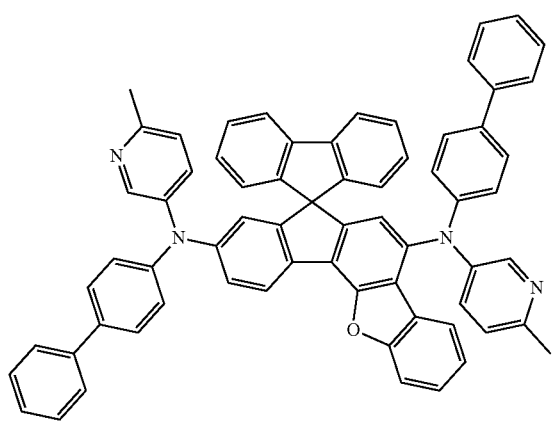
<Chemical Formula 25>
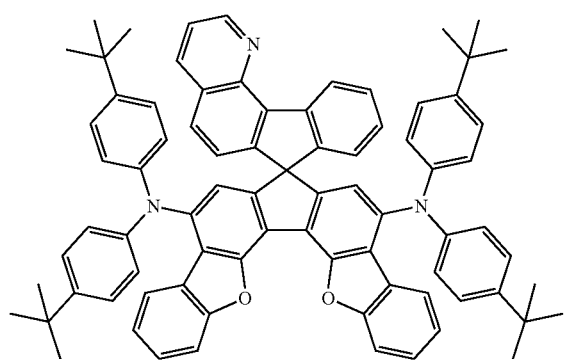

<Chemical Formula 26>
<Chemical Formula 27>
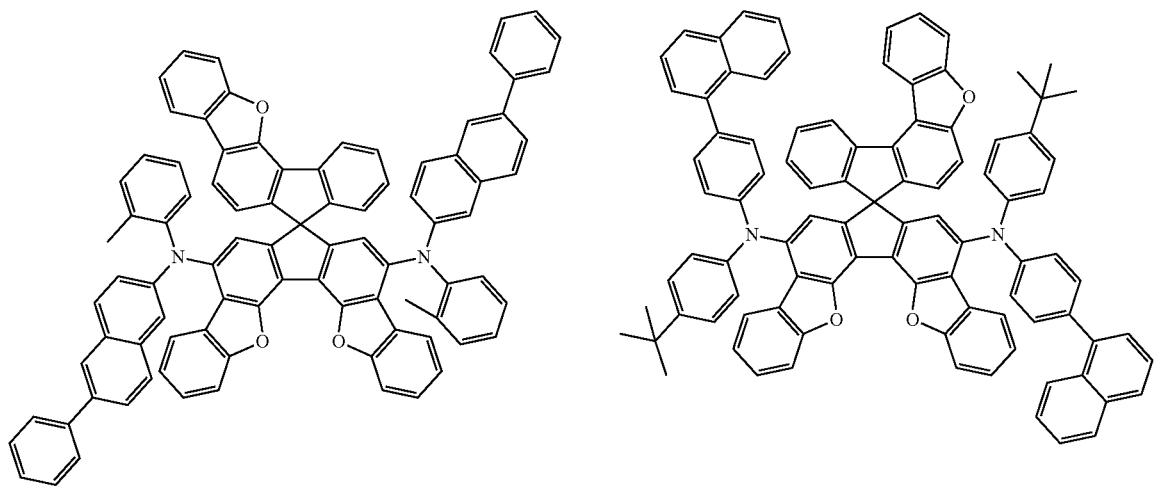
<Chemical Formula 28>
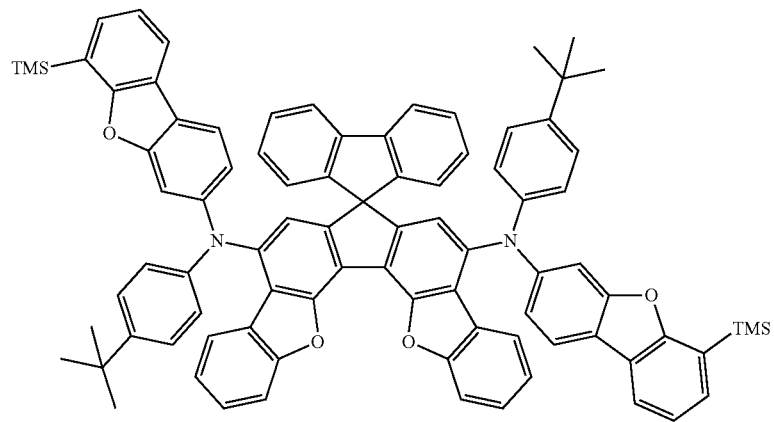
<Chemical Formula 29>
<Chemical Formula 30>
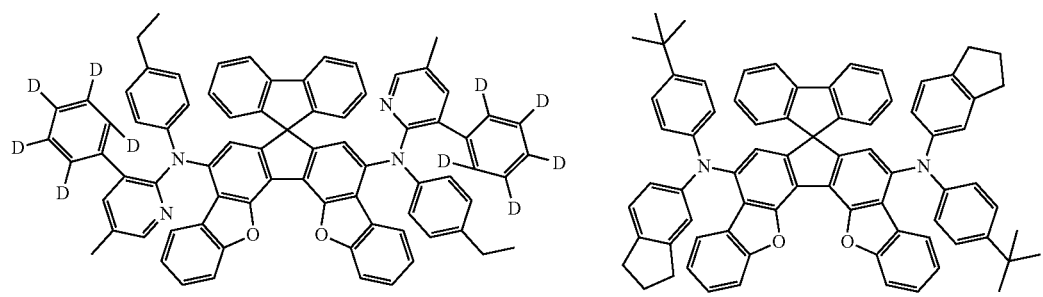

<Chemical Formula 31>
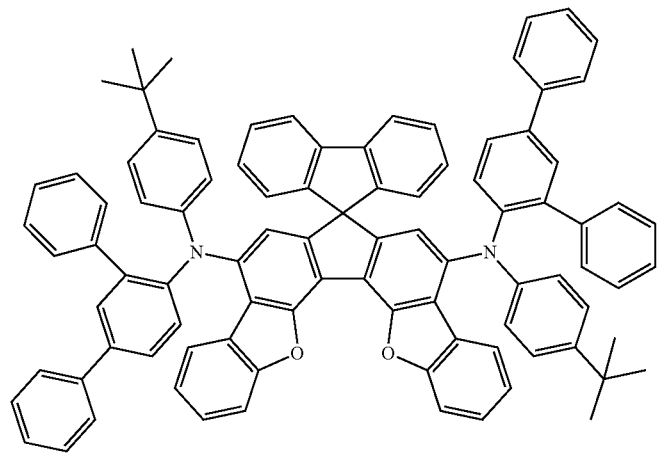
<Chemical Formula 32>
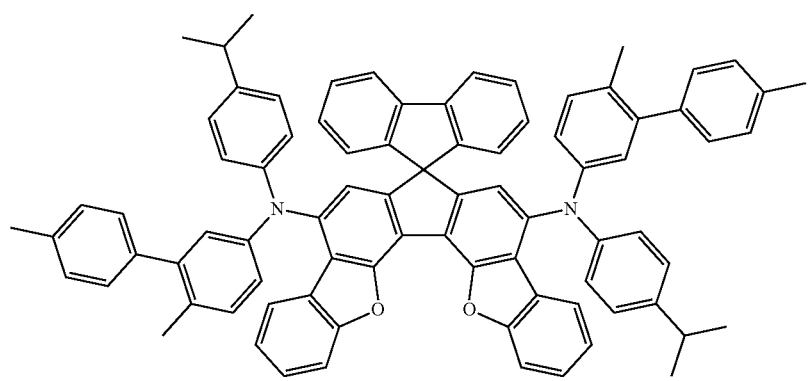
<Chemical Formula 33>
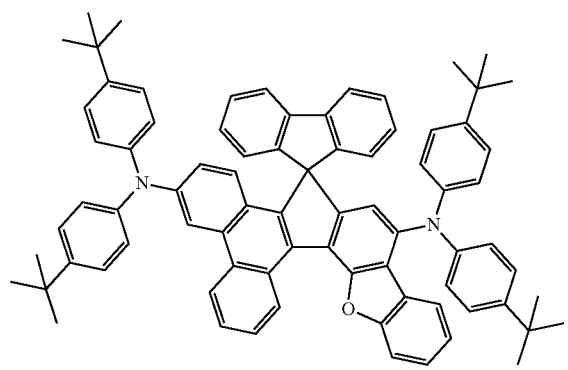
<Chemical Formula 34>
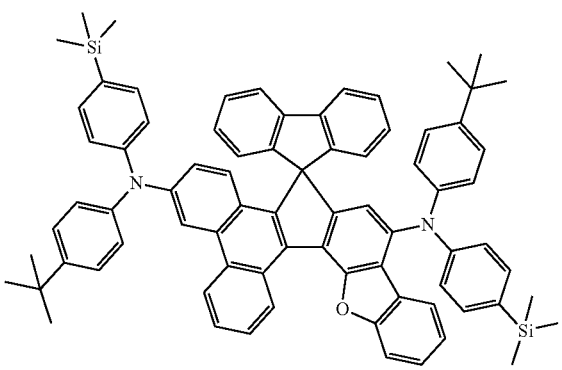

-continued
<Chemical Formula 35>
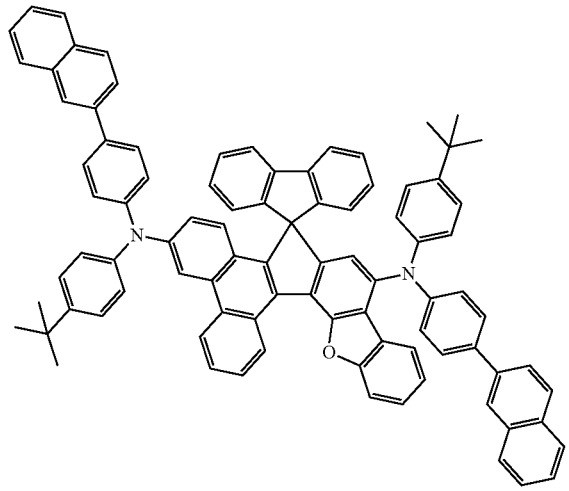
<Chemical Formula 36>
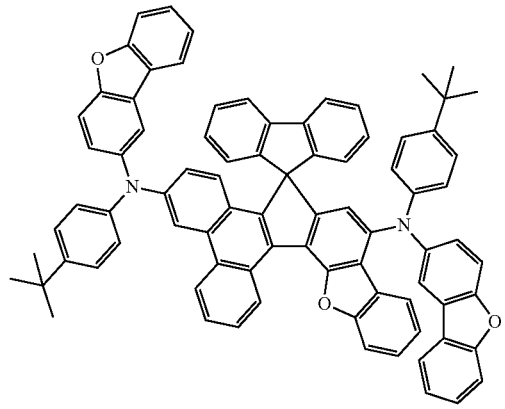
<Chemical Formula 37>
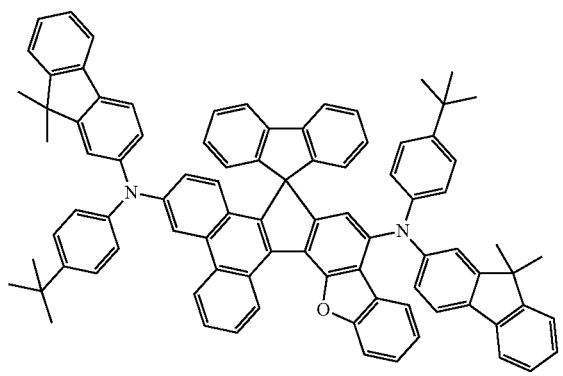
<Chemical Formula 38>
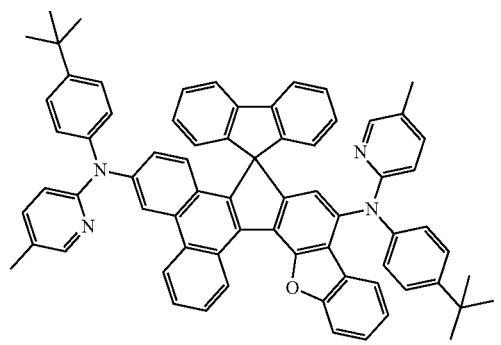
<Chemical Formula 39>
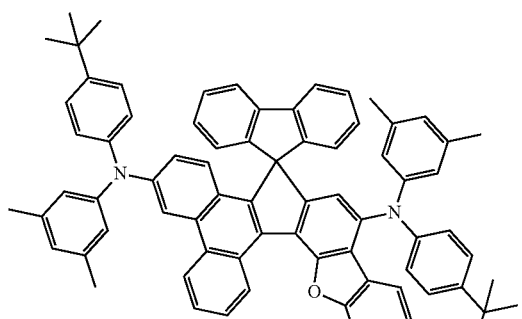
<Chemical Formula 40>
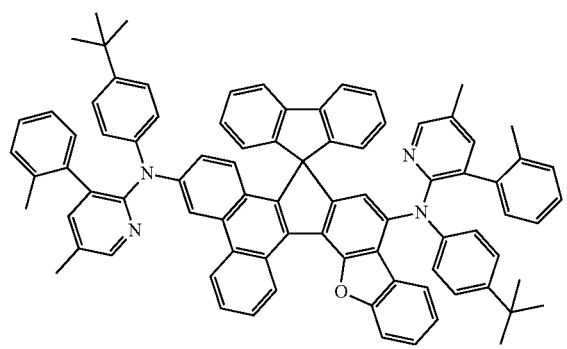
<Chemical Formula 41>
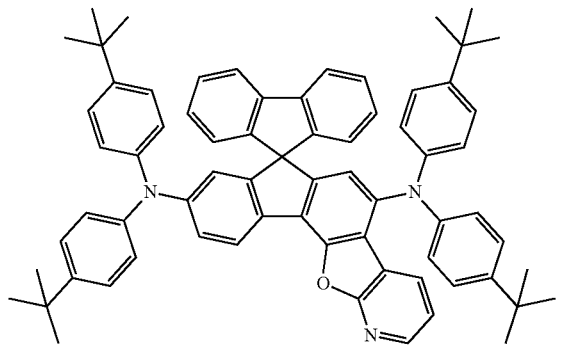
<Chemical Formula 42>
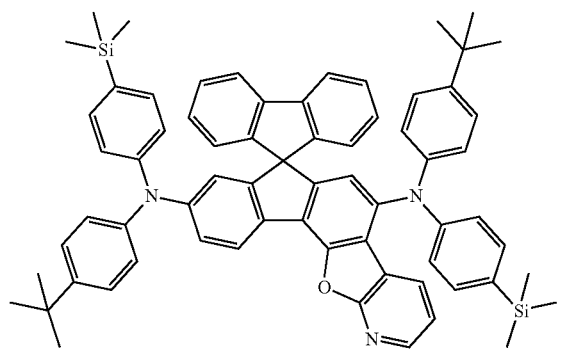

<Chemical Formula 43>
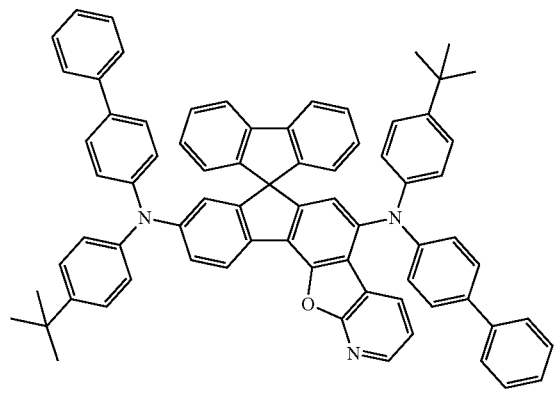
<Chemical Formula 44>
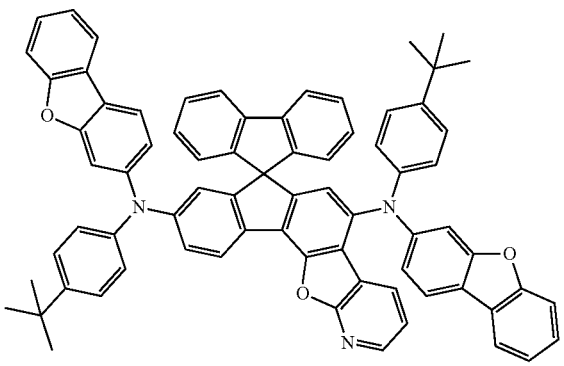
<Chemical Formula 45>
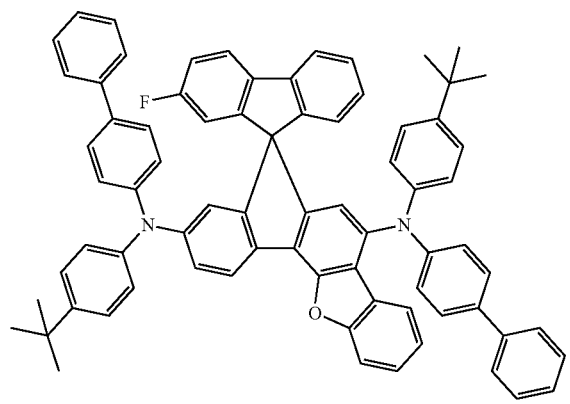
<Chemical Formula 46>
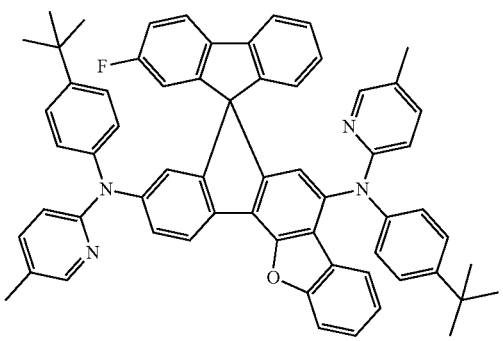
<Chemical Formula 47>
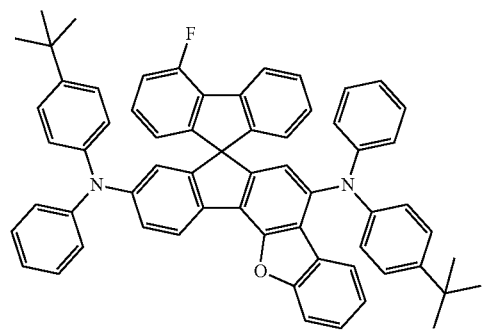
<Chemical Formula 48>
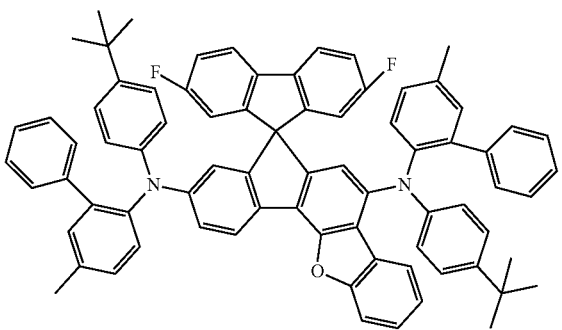
<Chemical Formula 49>
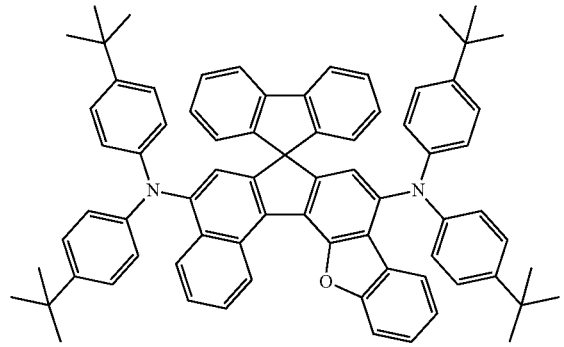
<Chemical Formula 50>
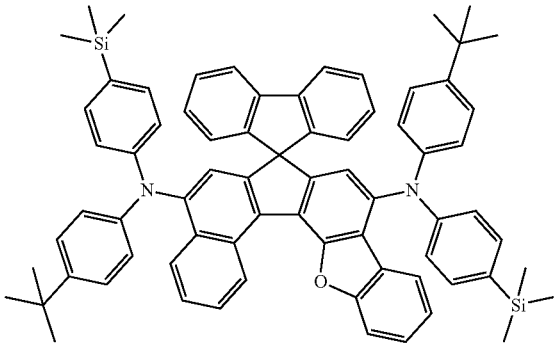

-continued
<Chemical Formula 51>
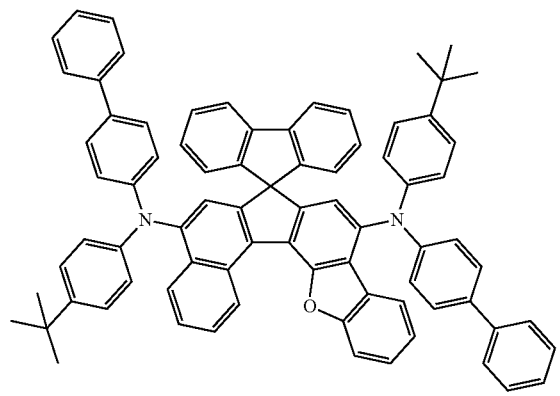
<Chemical Formula 52>
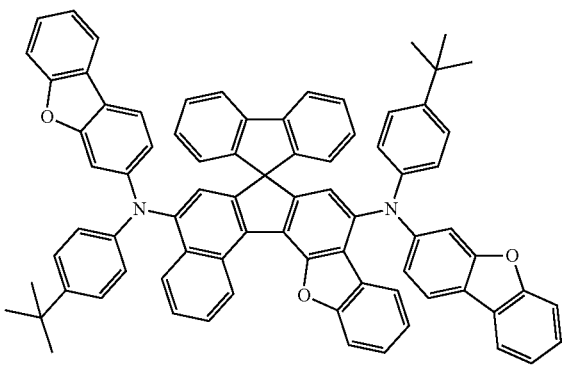
<Chemical Formula 53>
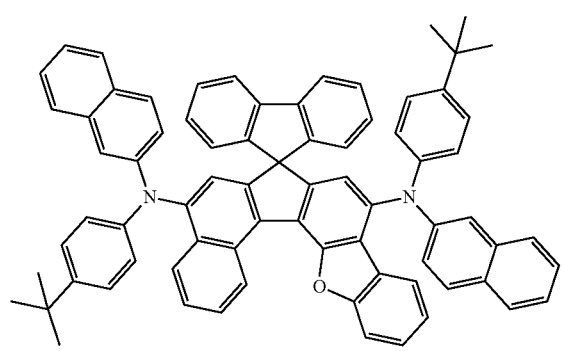
<Chemical Formula 54>
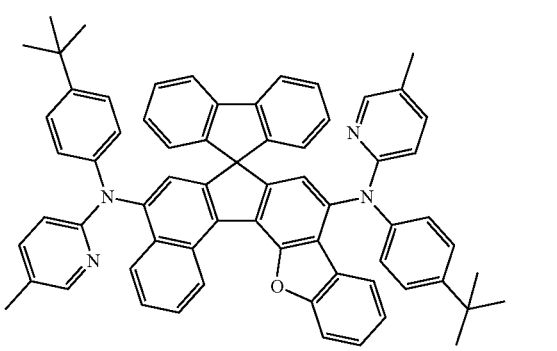
<Chemical Formula 55>
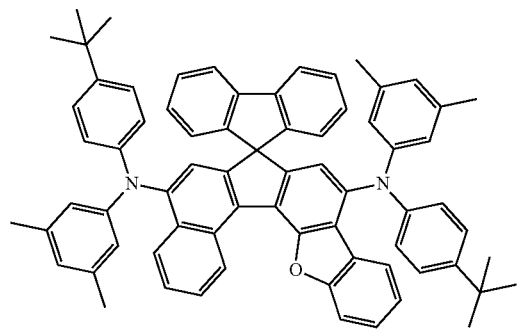
<Chemical Formula 56>
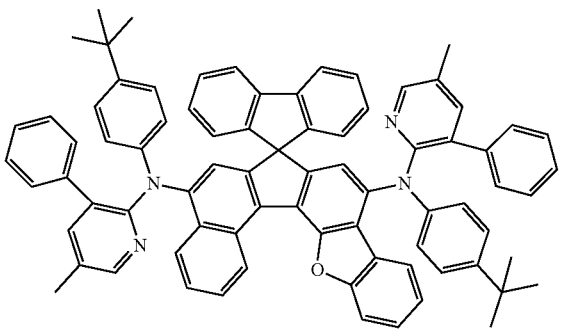
<Chemical Formula 57>
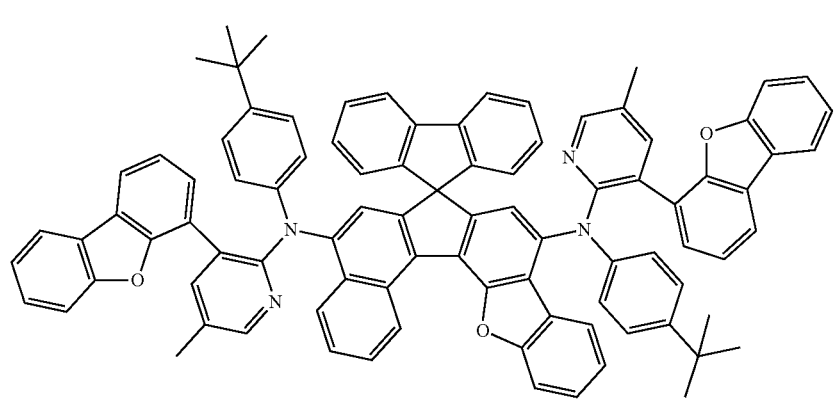

<Chemical Formula 58>
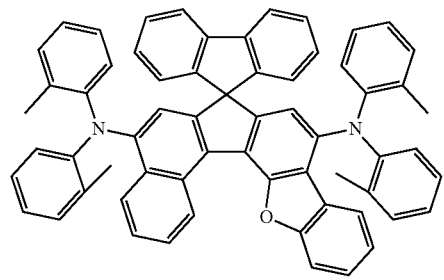
<Chemical Formula 59>
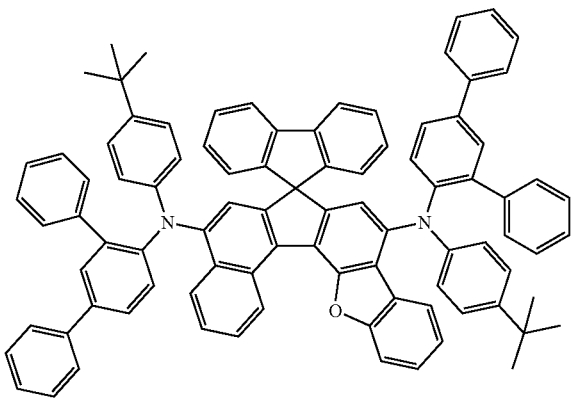
<Chemical Formula 60>
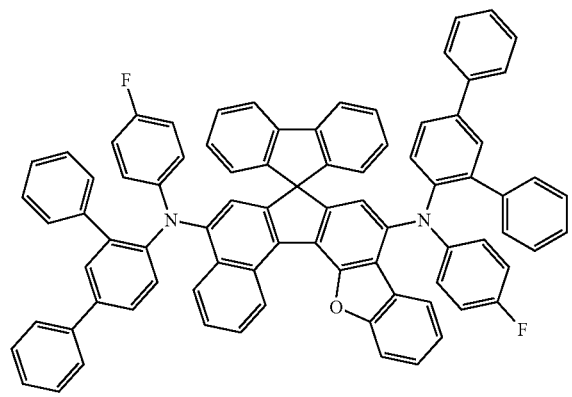
<Chemical Formula 61>
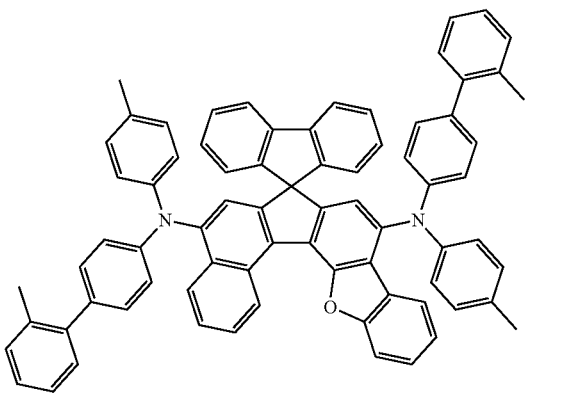
<Chemical Formula 62>
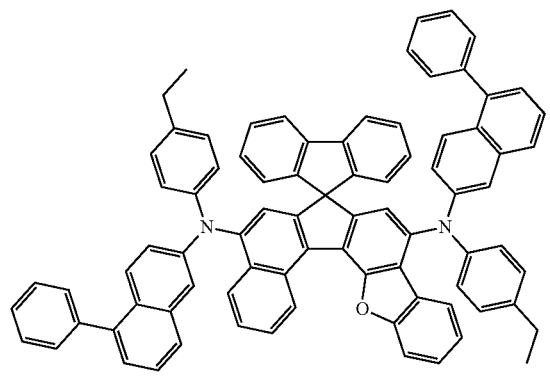
<Chemical Formula 63>
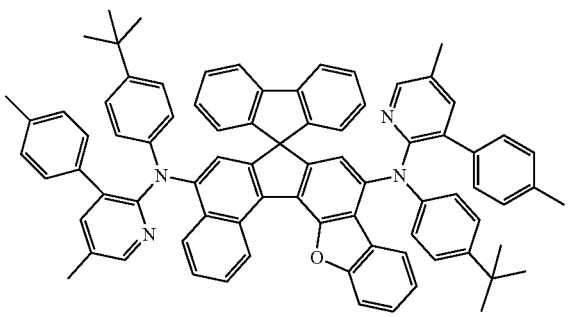
<Chemical Formula 64>
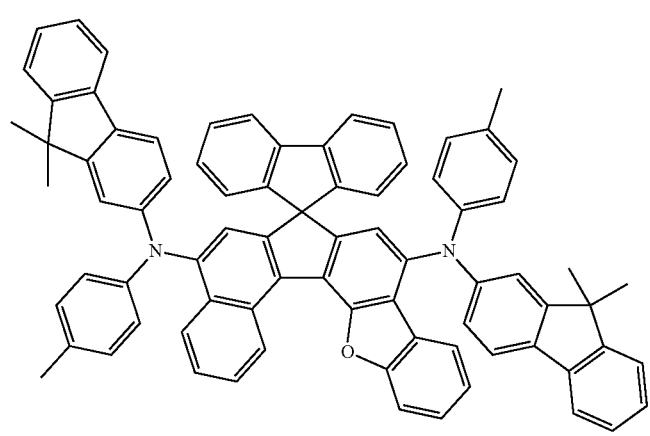

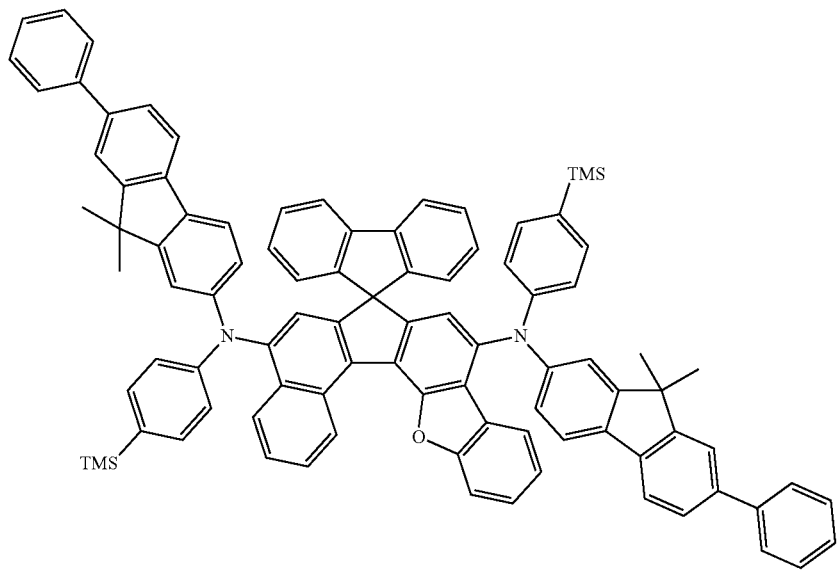
<Chemical Formula 65>
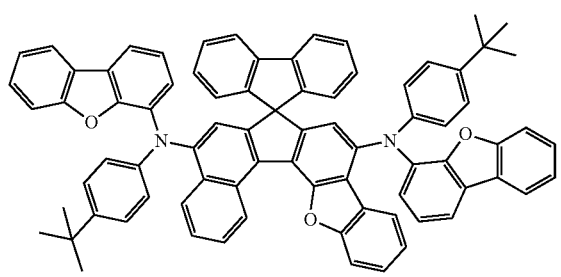
<Chemical Formula 66>
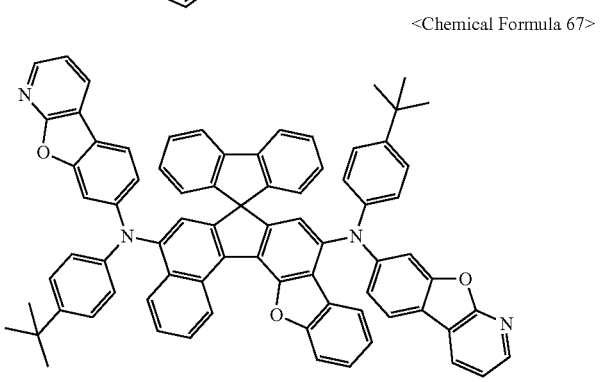
<Chemical Formula 67>
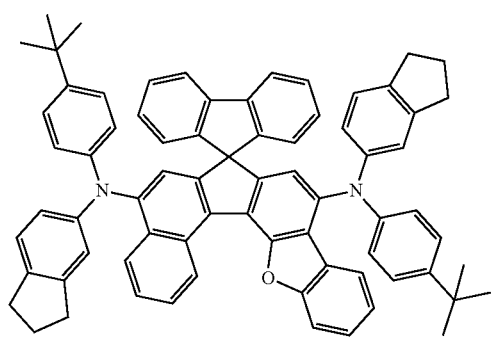
<Chemical Formula 68>
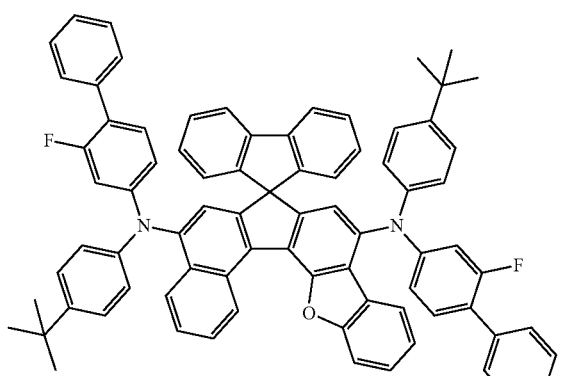
<Chemical Formula 69>
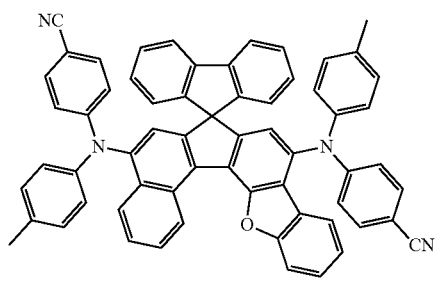
<Chemical Formula 70>
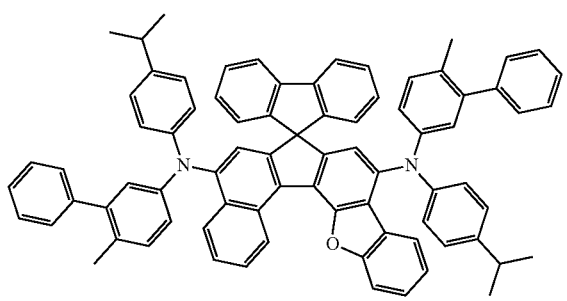
<Chemical Formula 71>

<Chemical Formula 72>
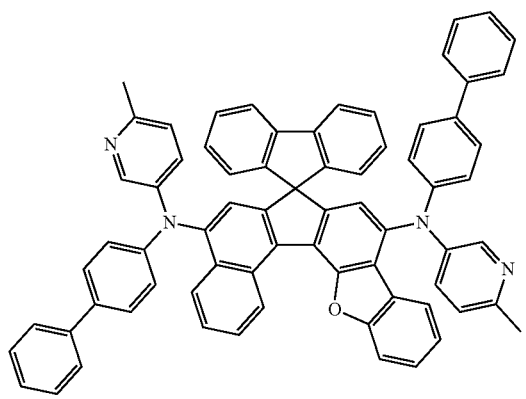
<Chemical Formula 73>
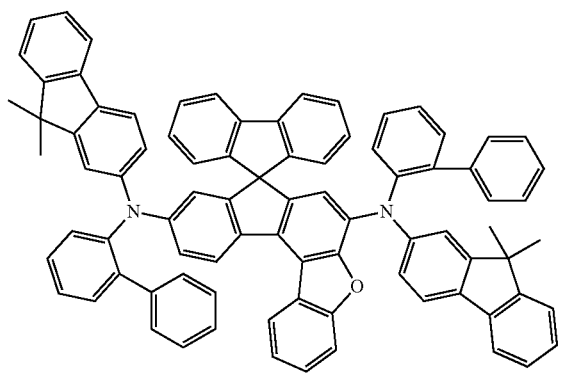
<Chemical Formula 74>
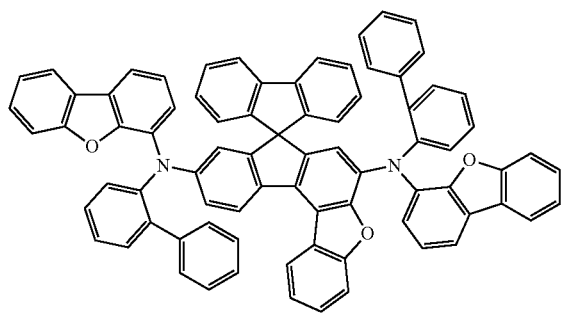
<Chemical Formula 75>
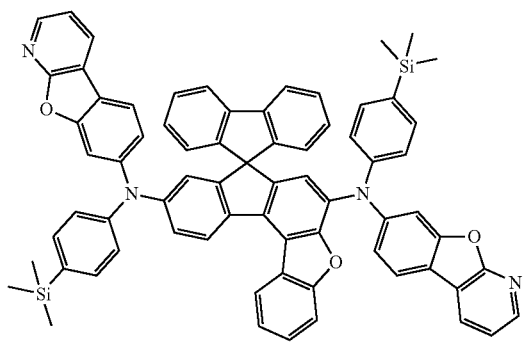
<Chemical Formula 76>
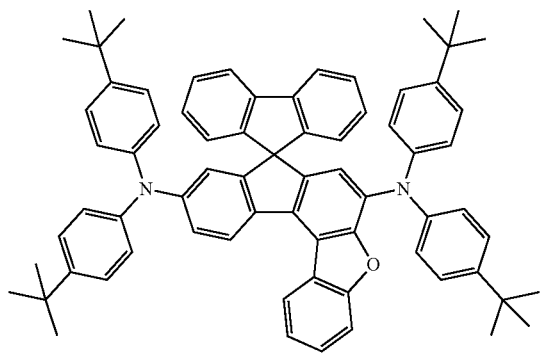
<Chemical Formula 77>
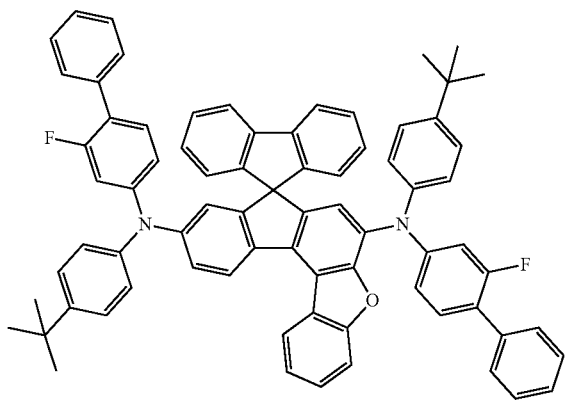
<Chemical Formula 78>
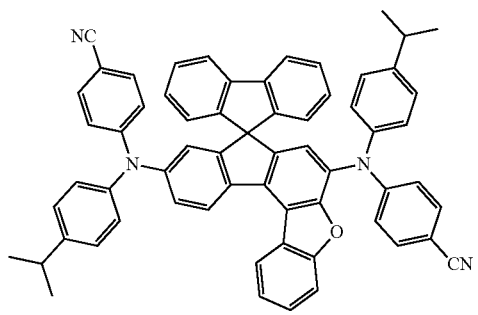
<Chemical Formula 79>
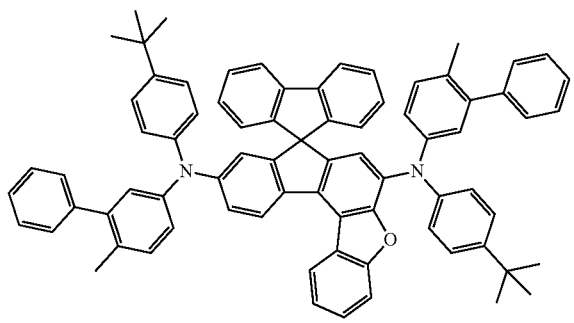

-continued
<Chemical Formula 80>
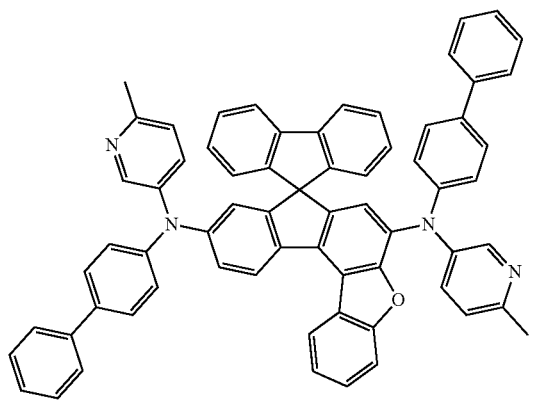
<Chemical Formula 81>
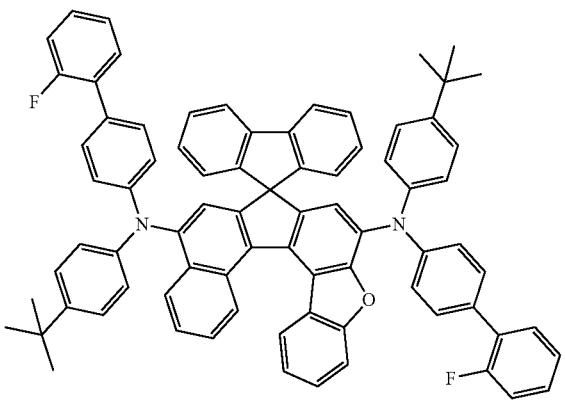
<Chemical Formula 82>
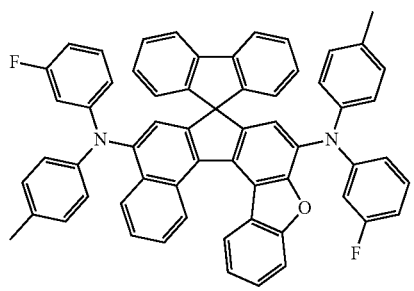
<Chemical Formula 83>
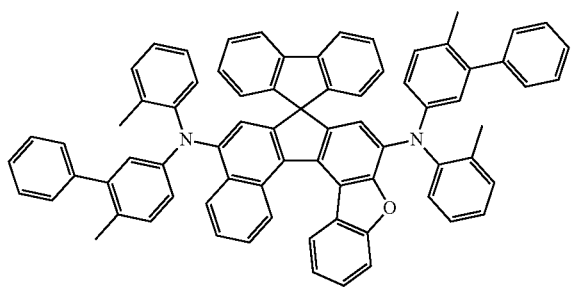
<Chemical Formula 84>
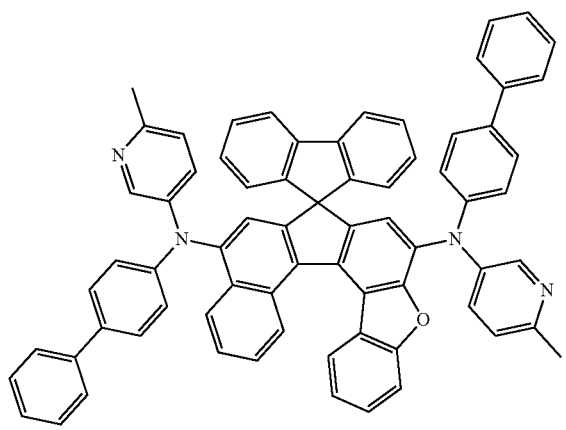
<Chemical Formula 85>
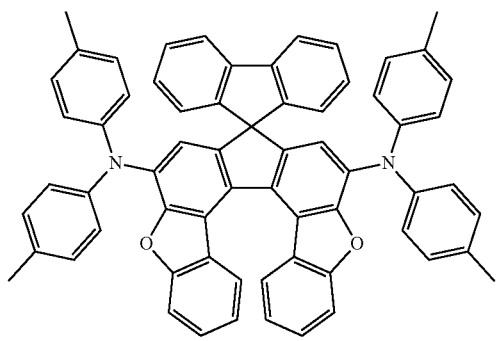
<Chemical Formula 86>
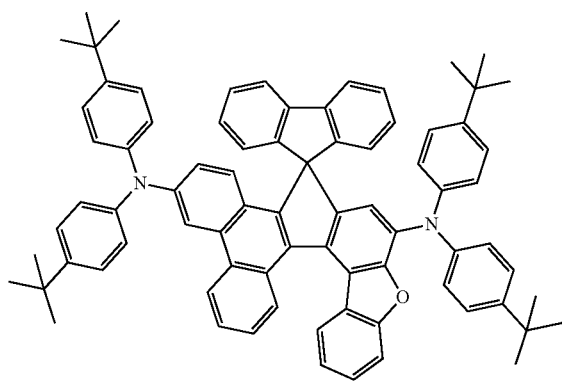
<Chemical Formula 87>
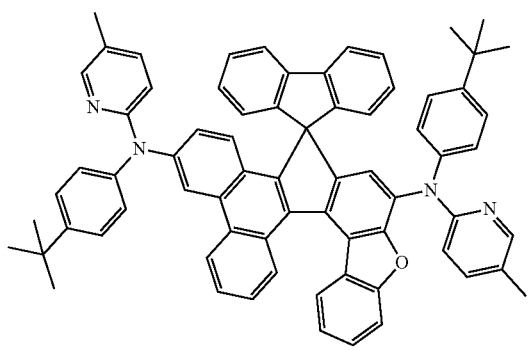

<Chemical Formula 88>
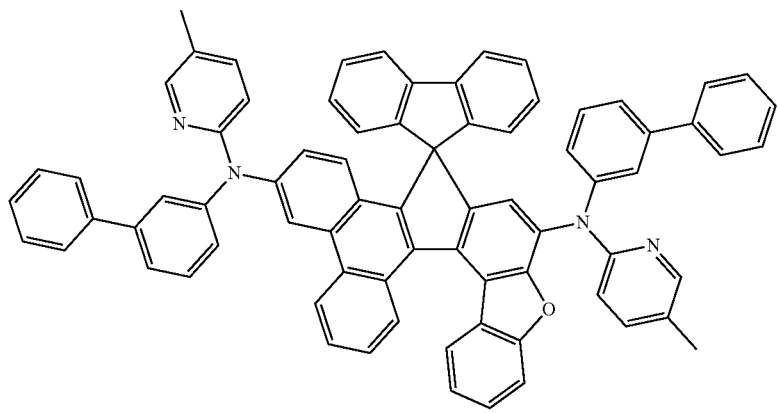
<Chemical Formula 89>
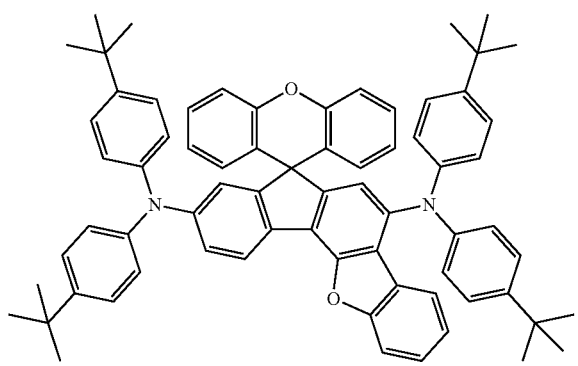
<Chemical Formula 90>
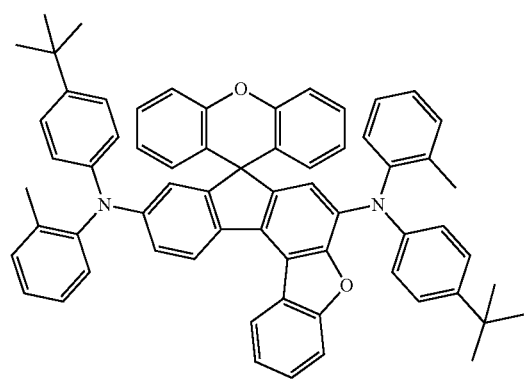
<Chemical Formula 91>
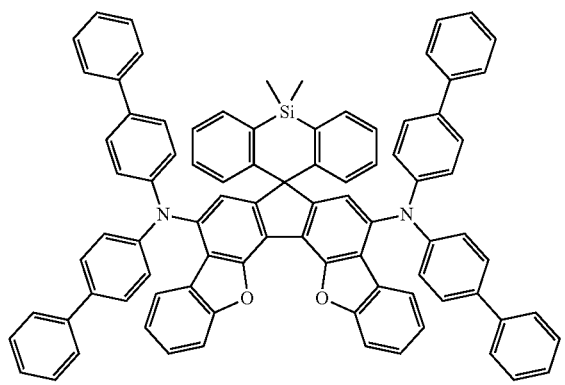
<Chemical Formula 92>
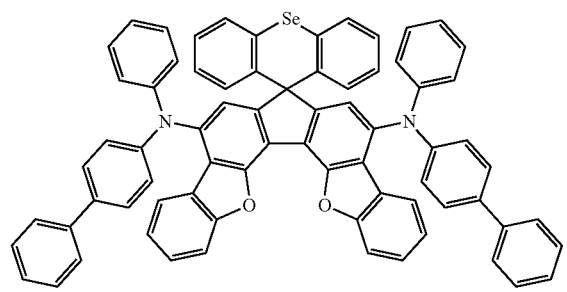
<Chemical Formula 93>
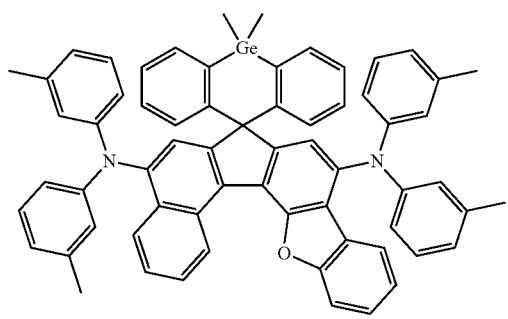
<Chemical Formula 94>
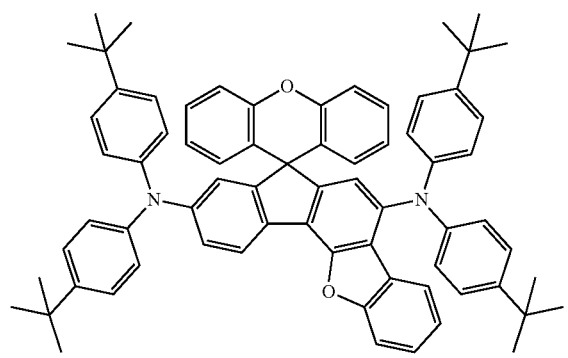

<Chemical Formula 95>
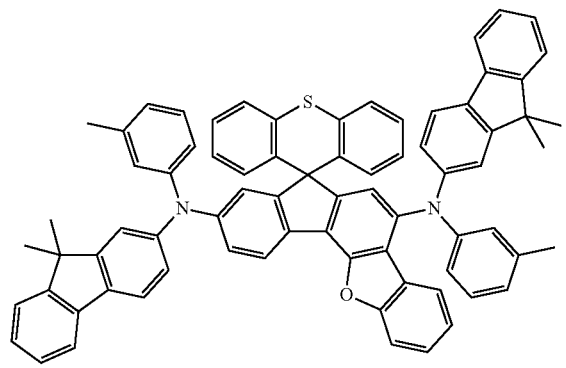
<Chemical Formula 96>
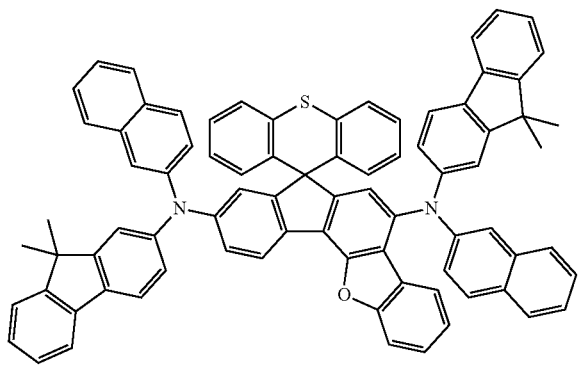
<Chemical Formula 97>
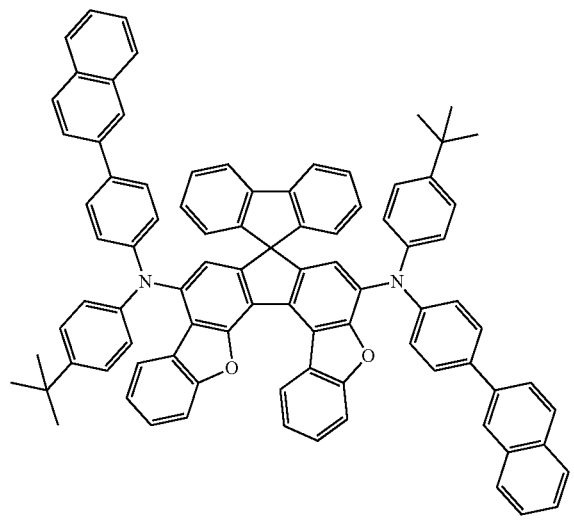
<Chemical Formula 98>
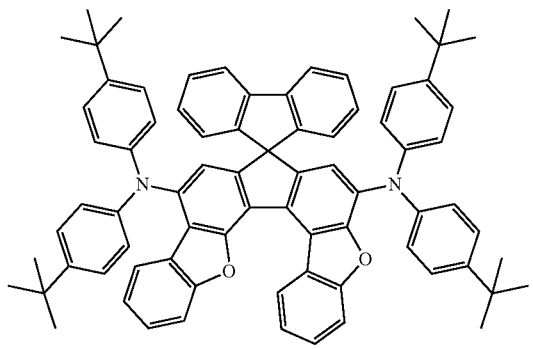
<Chemical Formula 99>
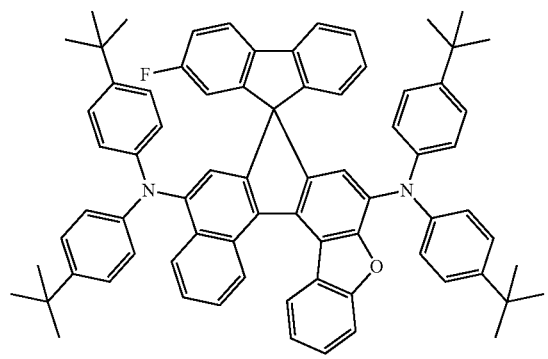
<Chemical Formula 100>
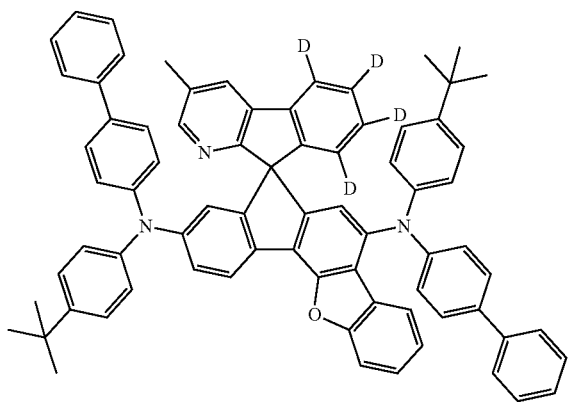

-continued
<Chemical Formula 101>
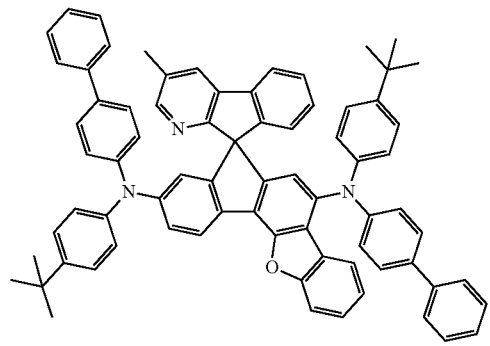
<Chemical Formula 102>
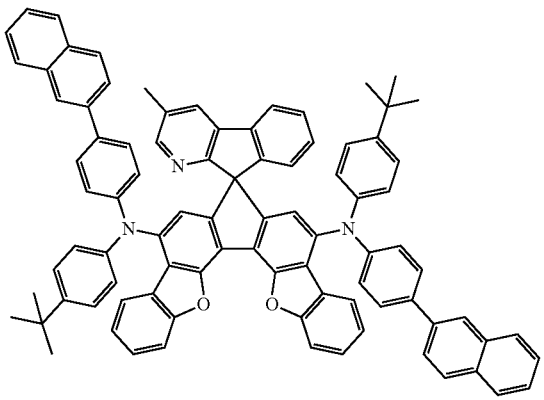
<Chemical Formula 103>
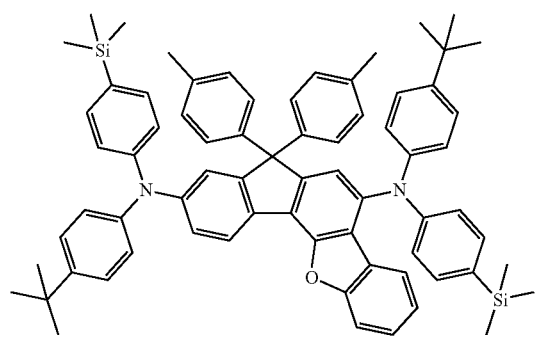
<Chemical Formula 104>
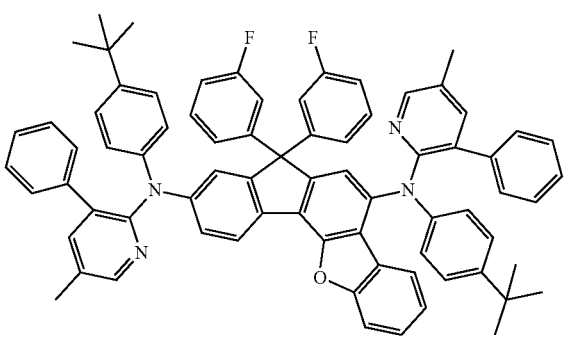
<Chemical Formula 105>
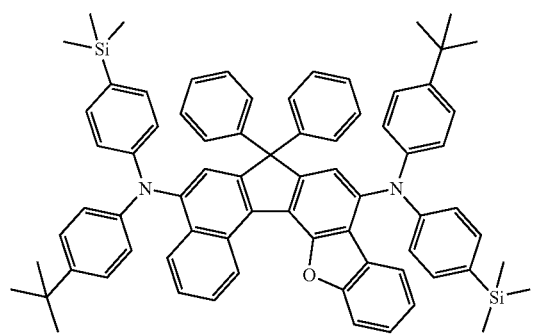
<Chemical Formula 106>
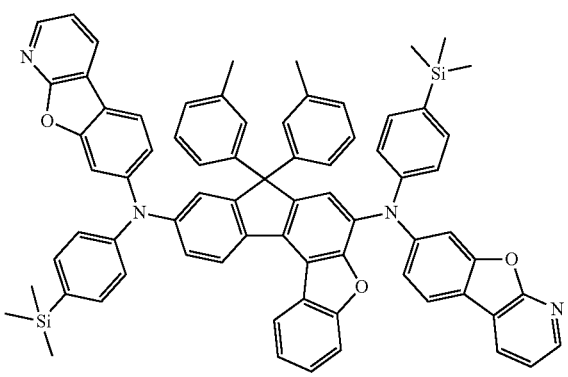
<Chemical Formula 107>
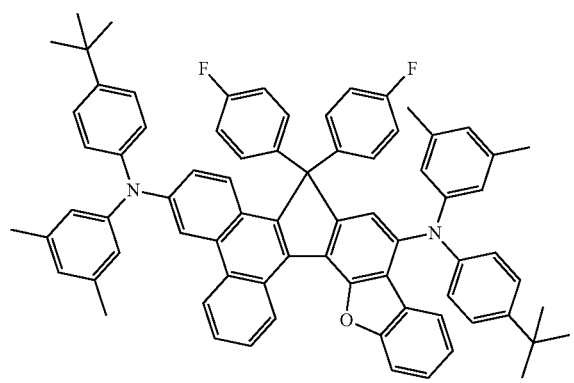
<Chemical Formula 108>
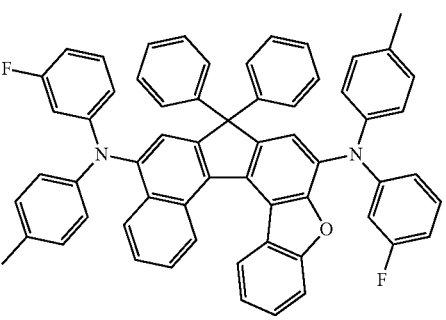

<Chemical Formula 109>
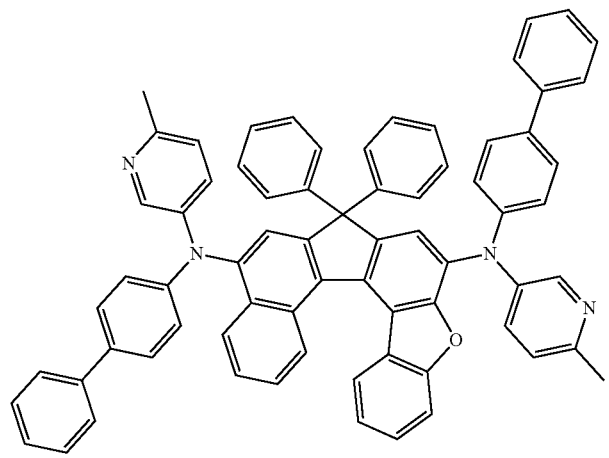
<Chemical Formula 110>
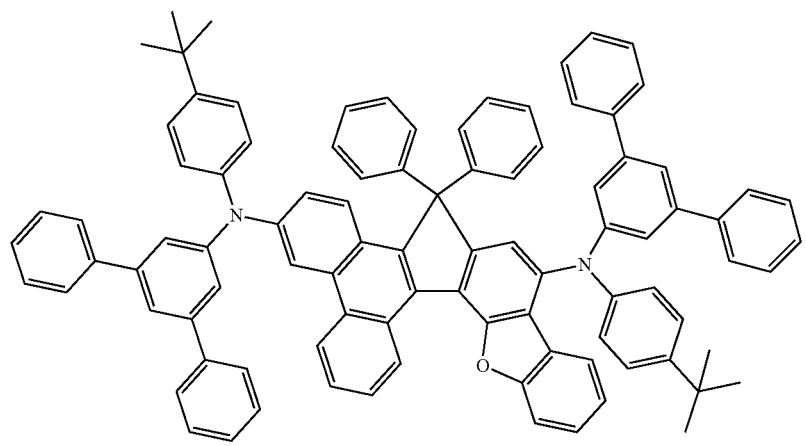
<Chemical Formula 111>
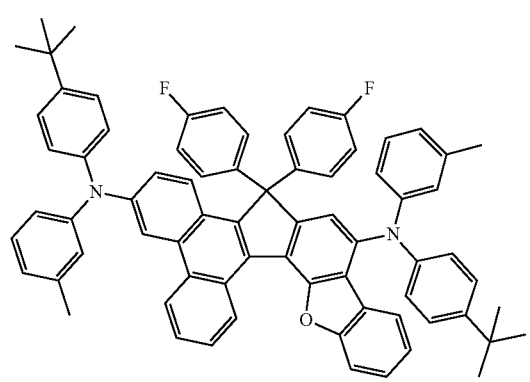
<Chemical Formula 112>
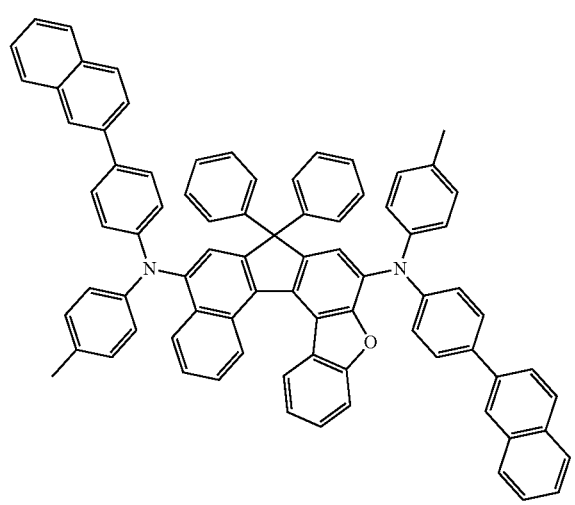

-continued
<Chemical Formula 113>
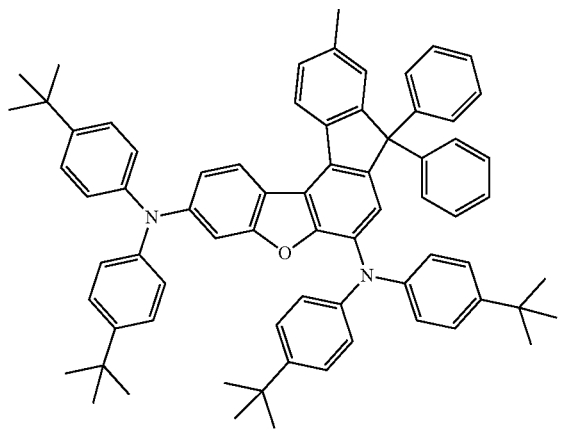
<Chemical Formula 114>
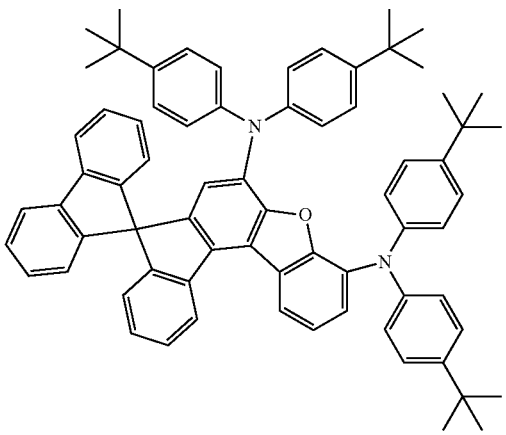
<Chemical Formula 115>
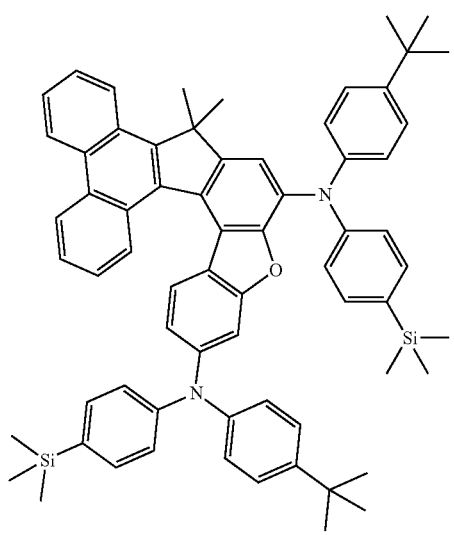
<Chemical Formula 116>
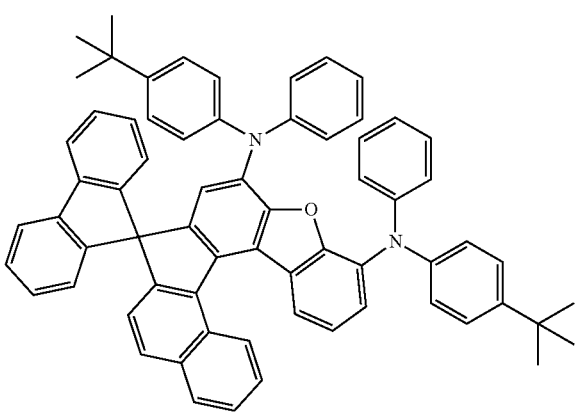
<Chemical Formula 117>
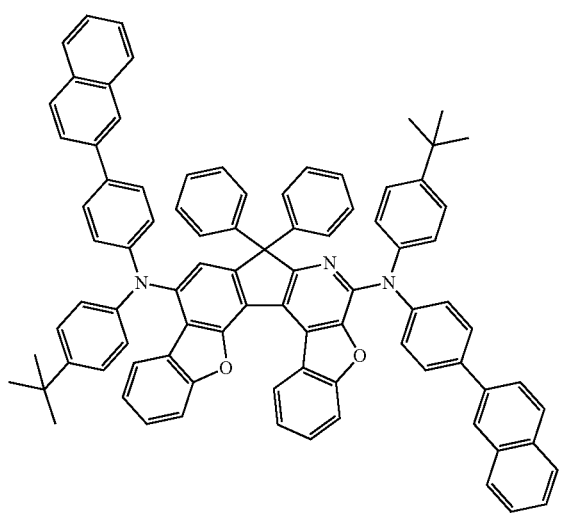
<Chemical Formula 118>
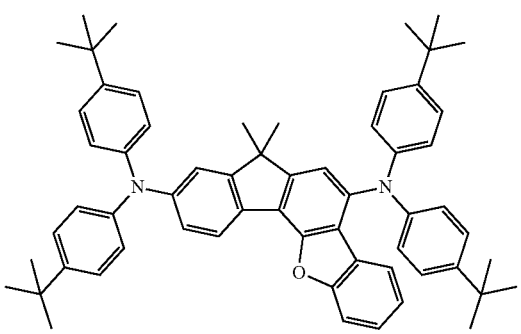

-continued
<Chemical Formula 119>
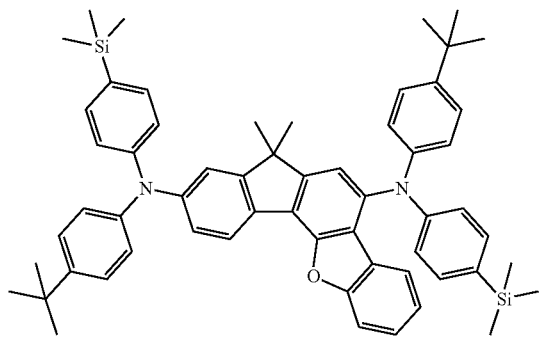
<Chemical Formula 120>
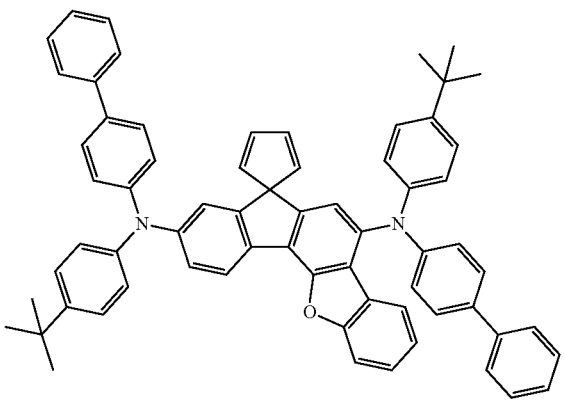
<Chemical Formula 121>
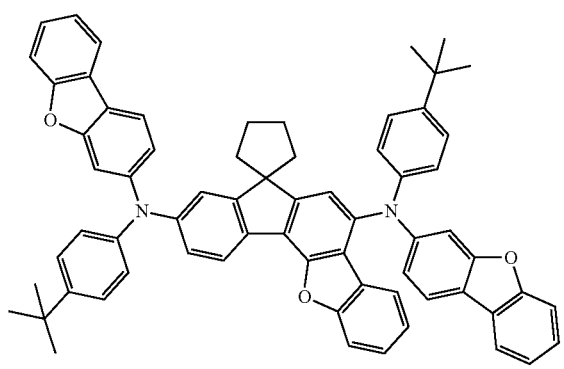
<Chemical Formula 122>
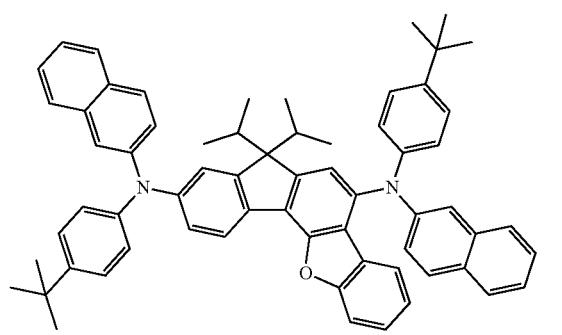
<Chemical Formula 123>
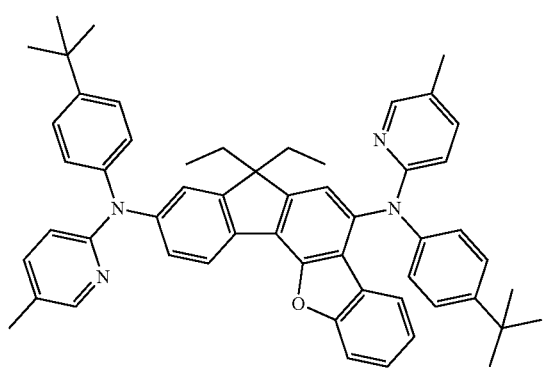
<Chemical Formula 124>
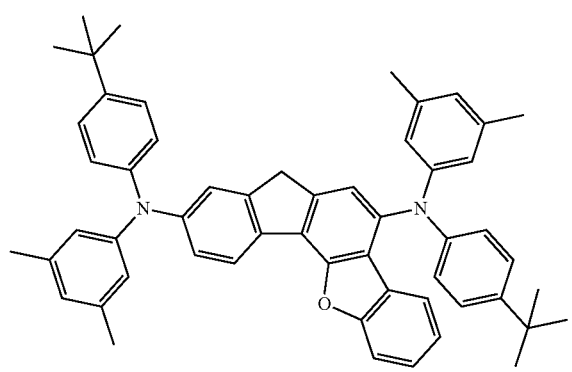
<Chemical Formula 125>
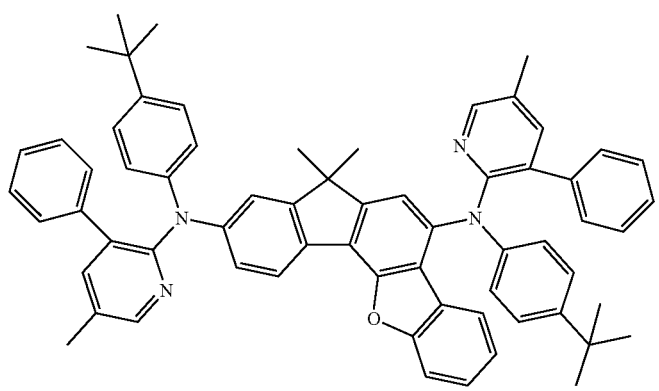

<Chemical Formula 126>
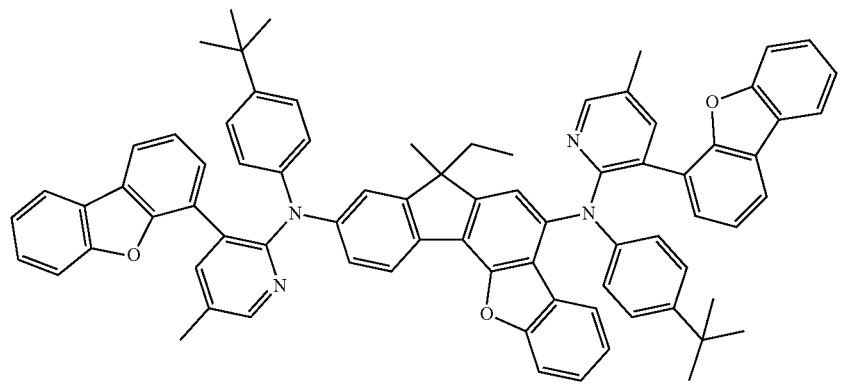
<Chemical Formula 127>
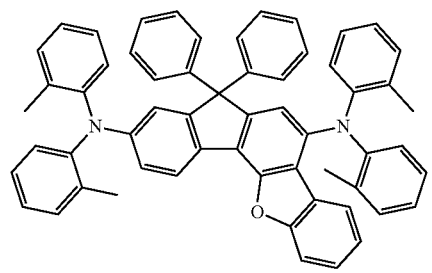
<Chemical Formula 128>
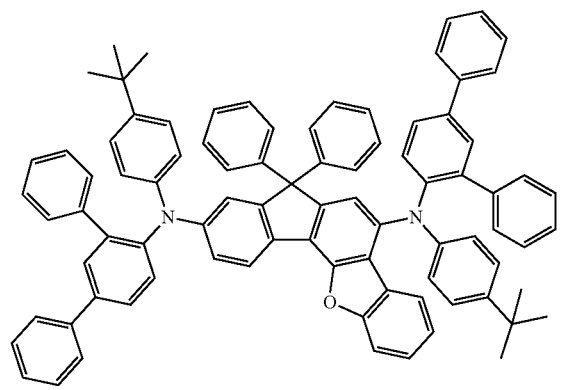
<Chemical Formula 129>
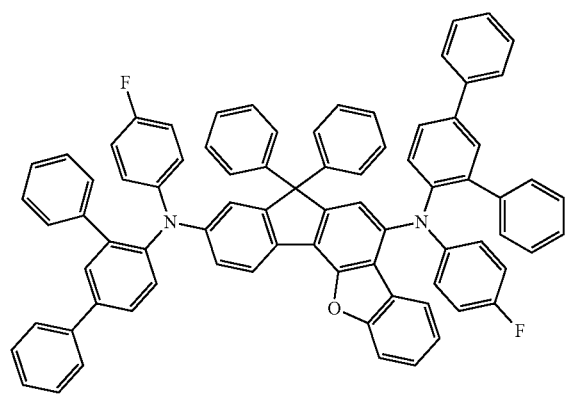
<Chemical Formula 130>
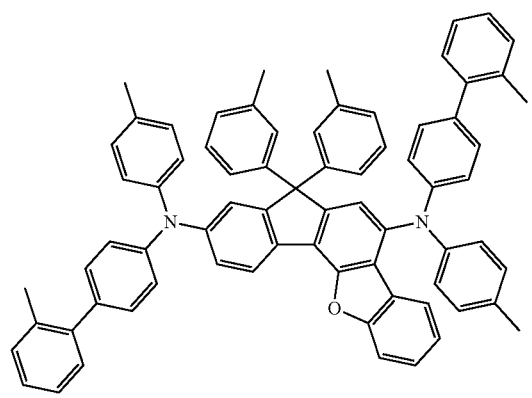

<Chemical Formula 131>
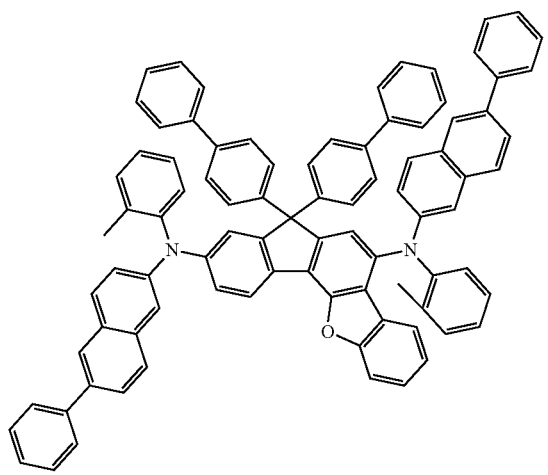
<Chemical Formula 132>
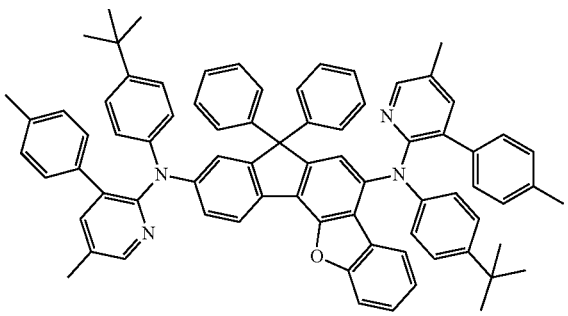
<Chemical Formula 133>
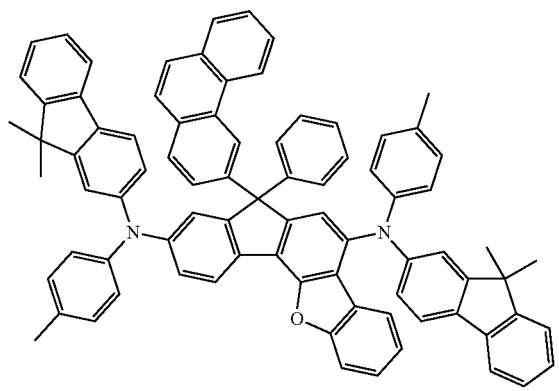
<Chemical Formula 134>
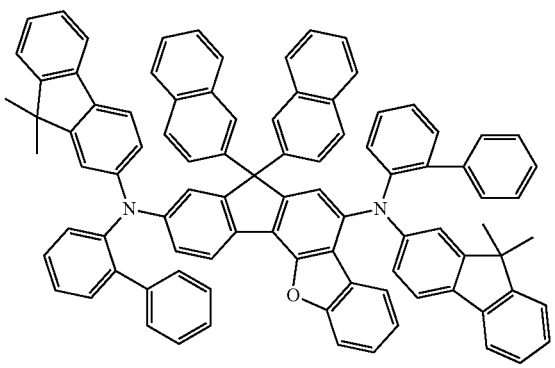
<Chemical Formula 135>
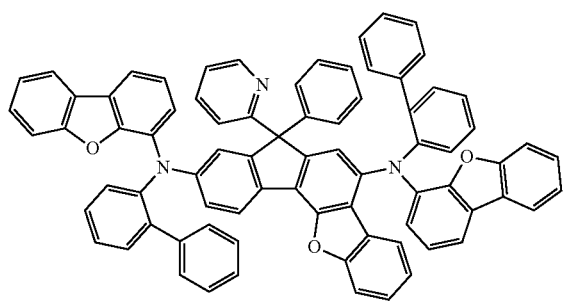
<Chemical Formula 136>
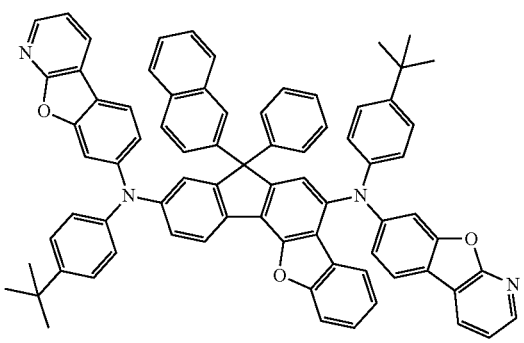

<Chemical Formula 137>
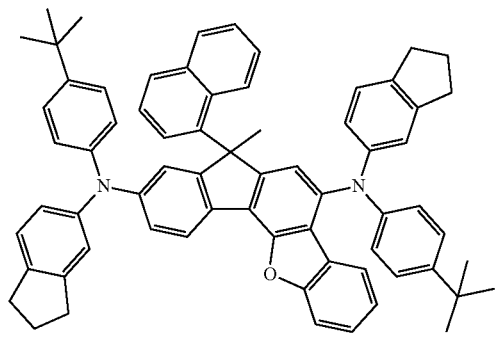
<Chemical Formula 138>
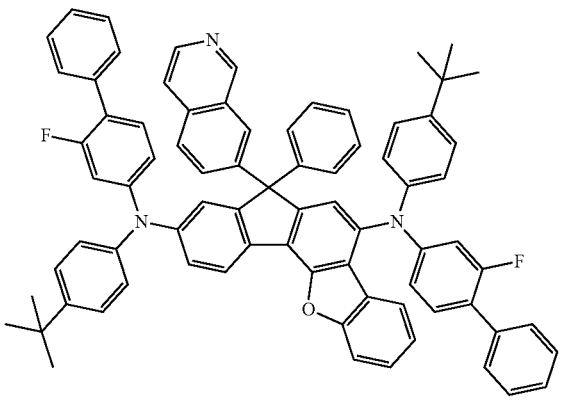
<Chemical Formula 139>
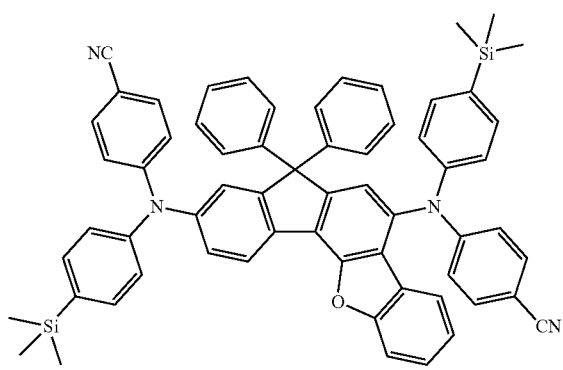
<Chemical Formula 140>
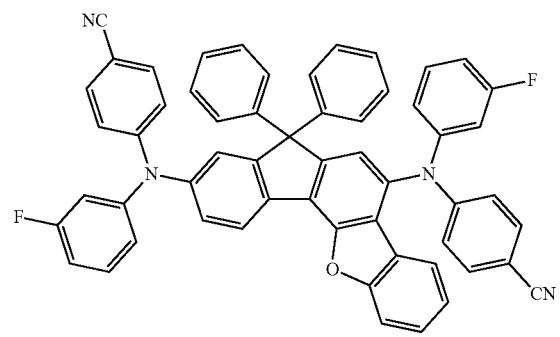
<Chemical Formula 141>
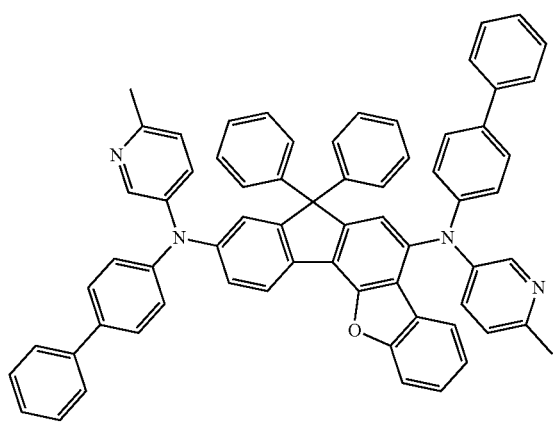
<Chemical Formula 142>
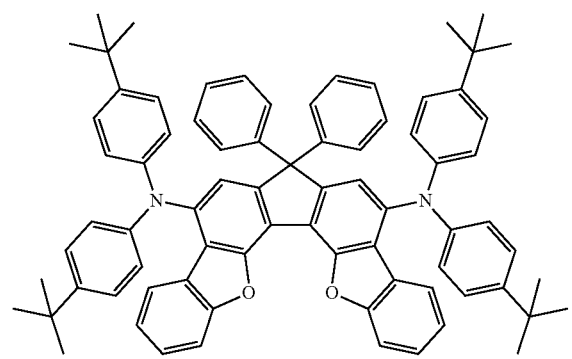

<Chemical Formula 143>
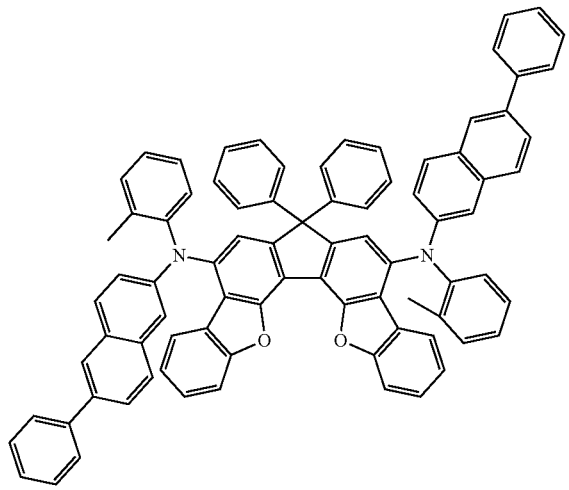
<Chemical Formula 144>
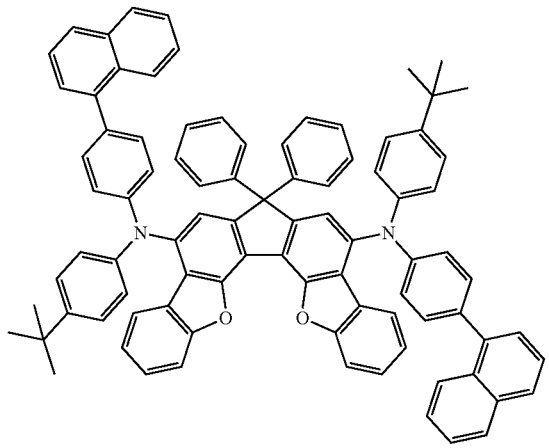
<Chemical Formula 145>
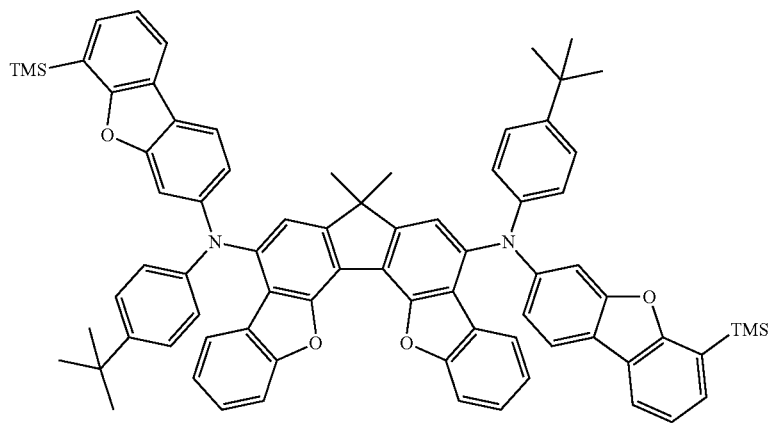
<Chemical Formula 146>
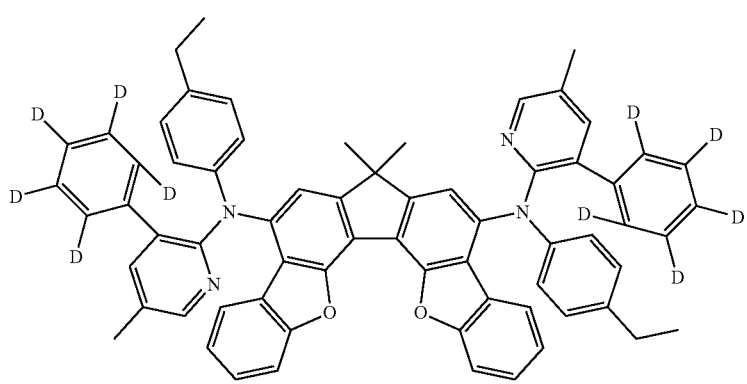

-continued
<Chemical Formula 147>
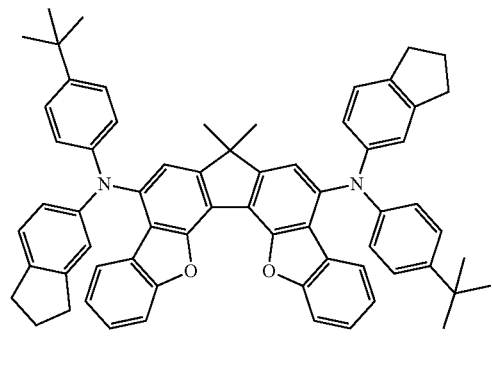
<Chemical Formula 148>
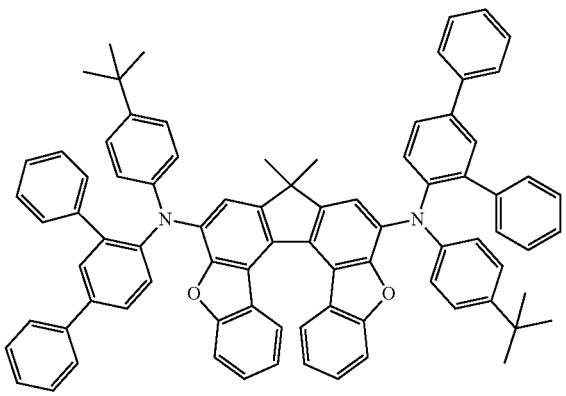
<Chemical Formula 149>
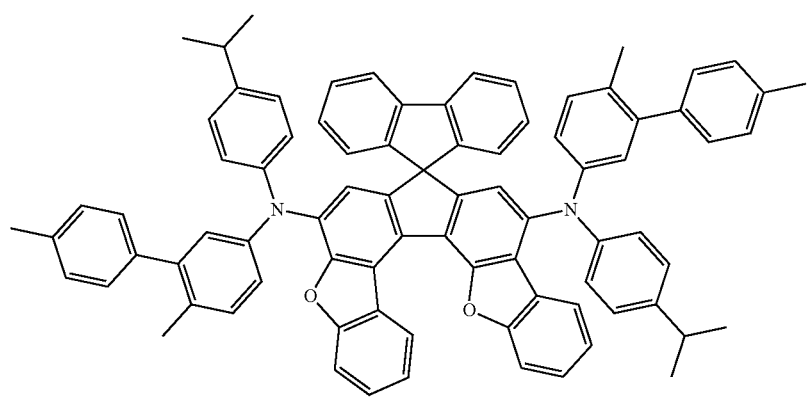
<Chemical Formula 150>
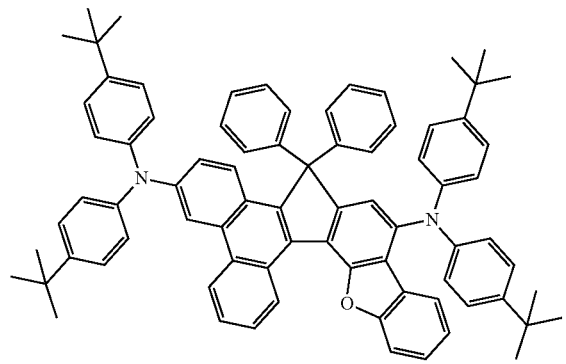
<Chemical Formula 151>
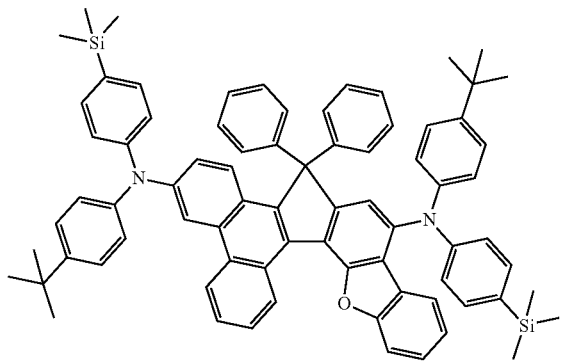

<Chemical Formula 152>
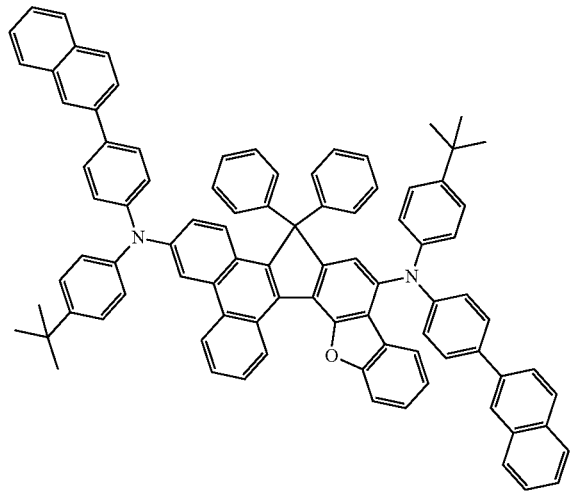
<Chemical Formula 153>
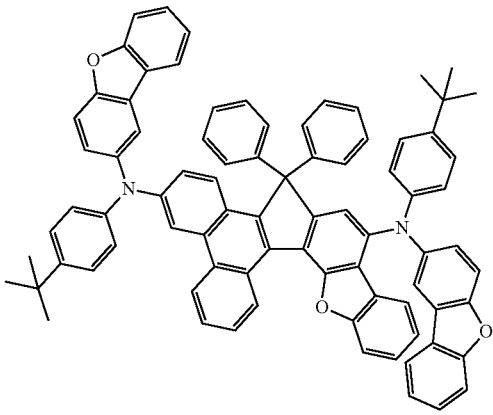
<Chemical Formula 154>
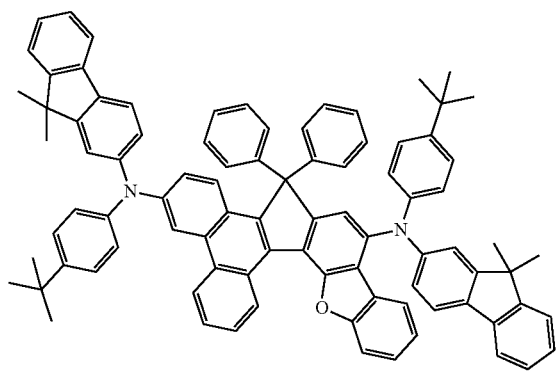
<Chemical Formula 155>
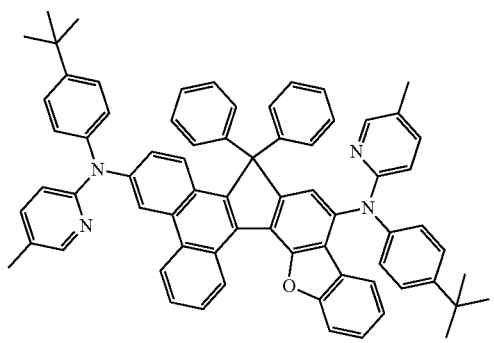
<Chemical Formula 156>
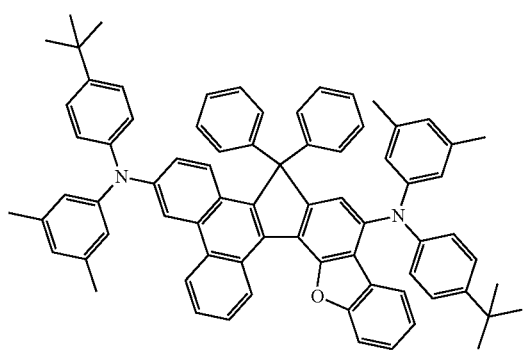
<Chemical Formula 157>
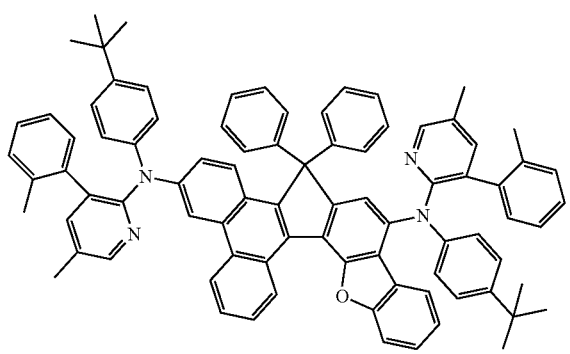
<Chemical Formula 158>
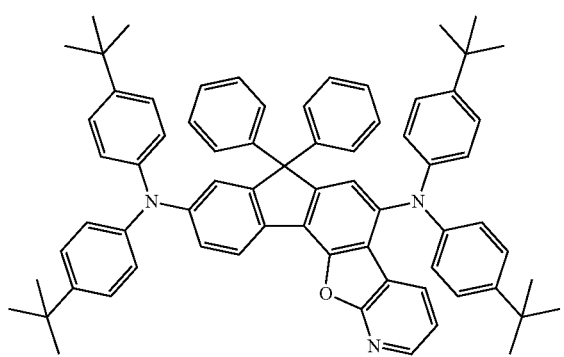
<Chemical Formula 159>
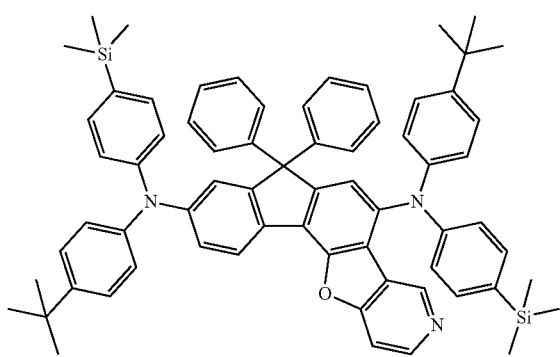

<Chemical Formula 160>
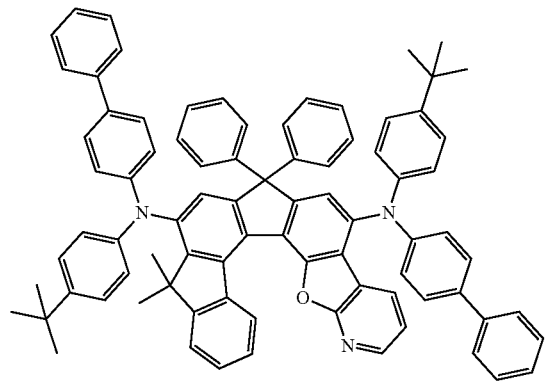
<Chemical Formula 161>
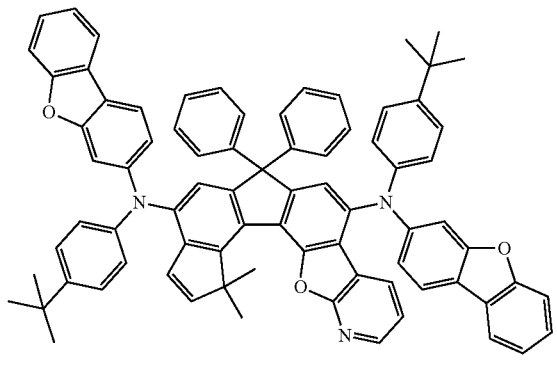
<Chemical Formula 162>
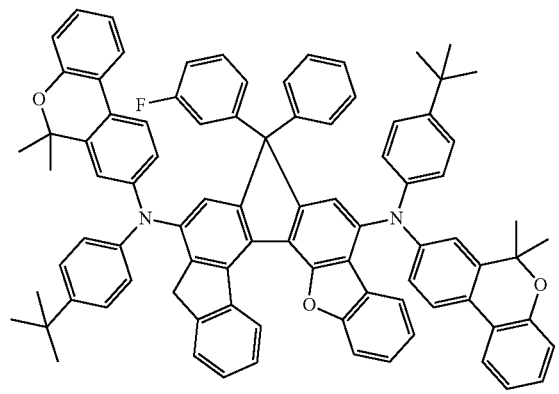
<Chemical Formula 163>
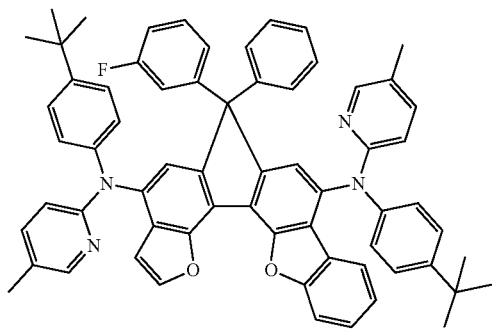
<Chemical Formula 164>
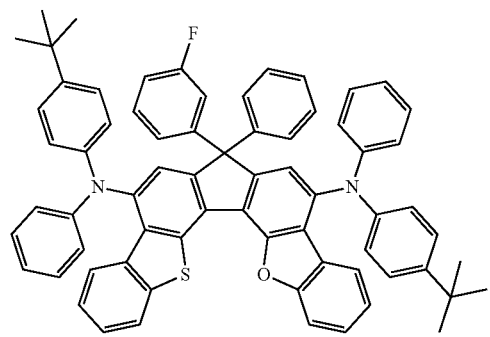
<Chemical Formula 165>
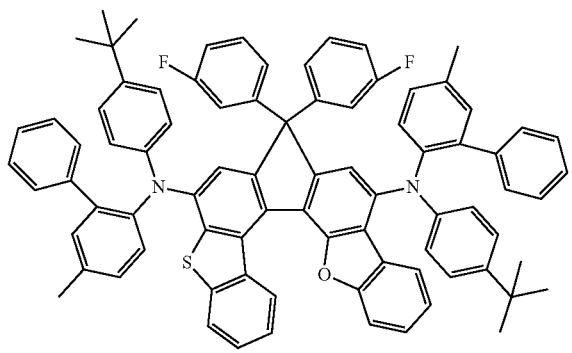
<Chemical Formula 166>
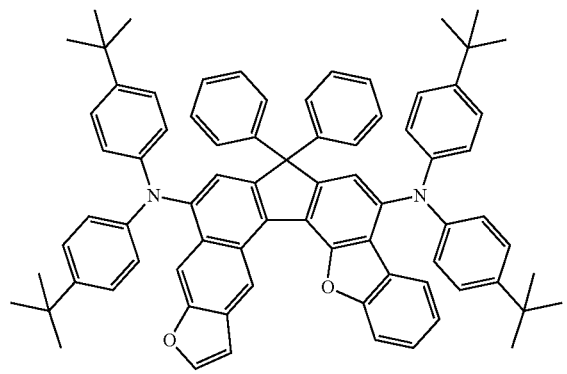
<Chemical Formula 167>
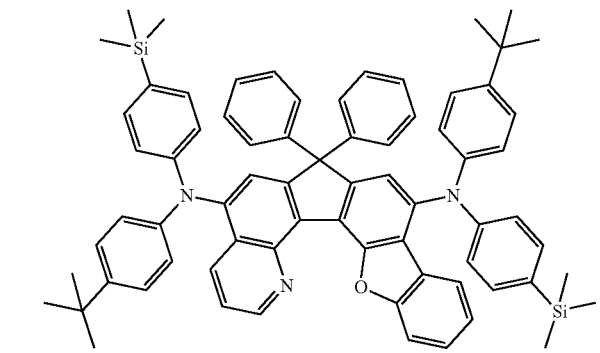

<Chemical Formula 168>
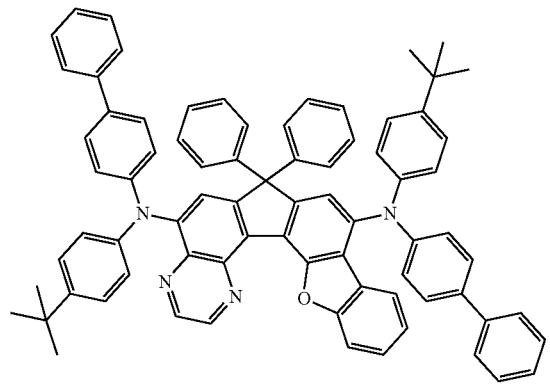
<Chemical Formula 169>
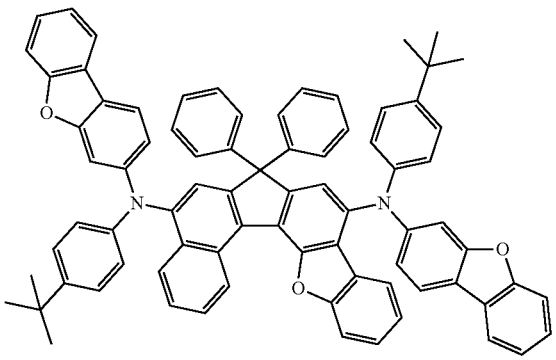
<Chemical Formula 170>
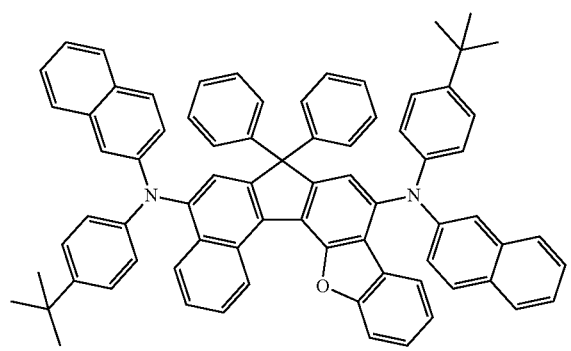
<Chemical Formula 171>
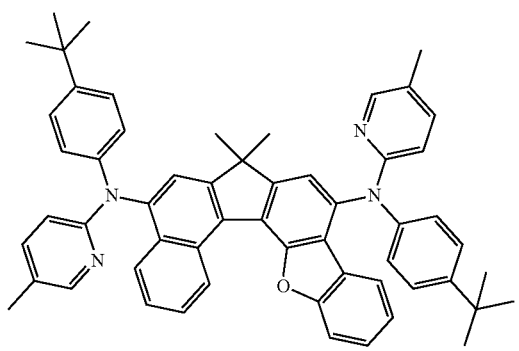
<Chemical Formula 172>
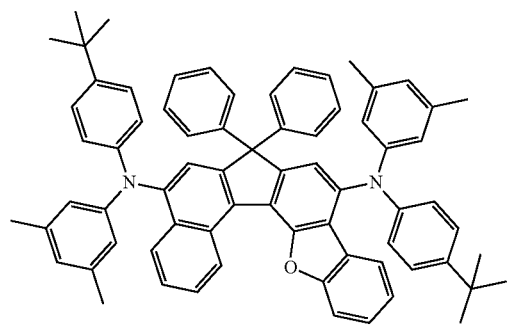
<Chemical Formula 173>
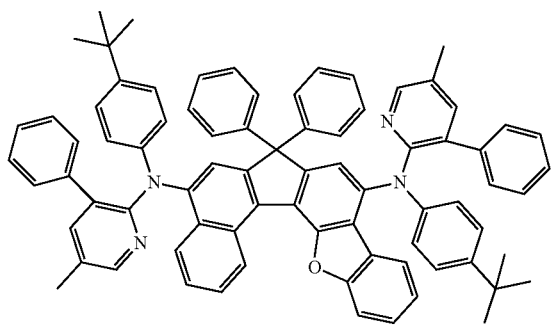
<Chemical Formula 174>
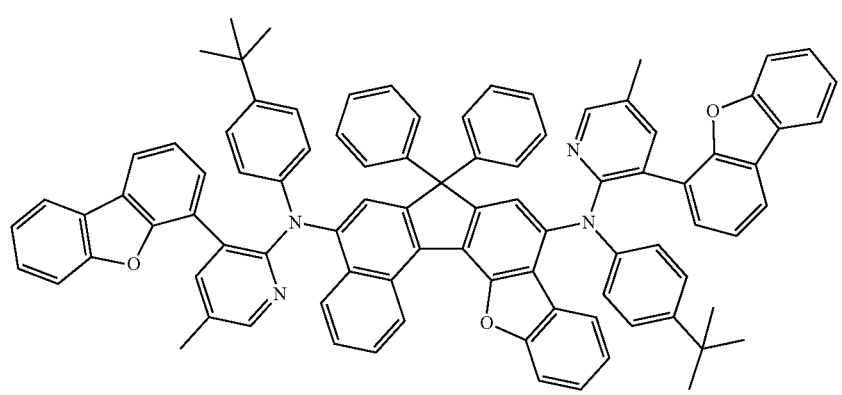

<Chemical Formula 175>
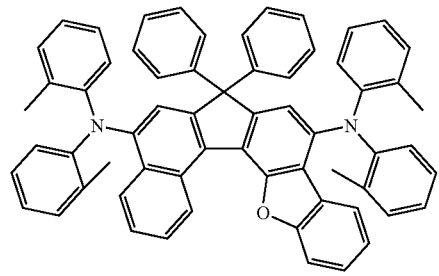
<Chemical Formula 176>
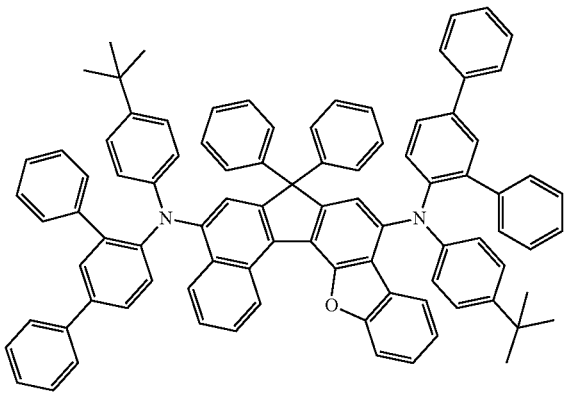
<Chemical Formula 177>
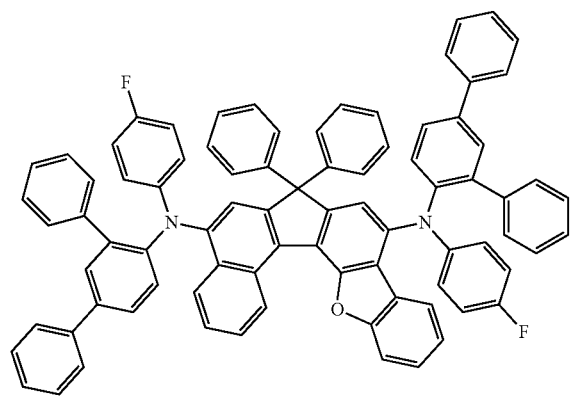
<Chemical Formula 178>
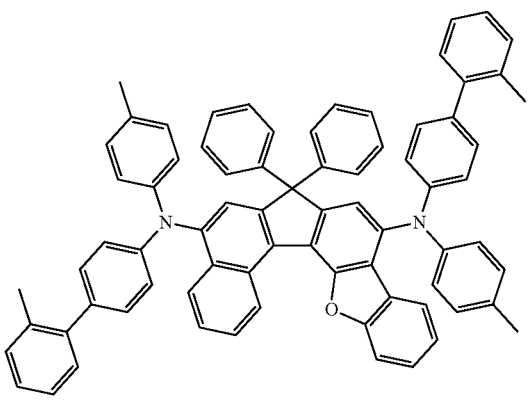
<Chemical Formula 179>
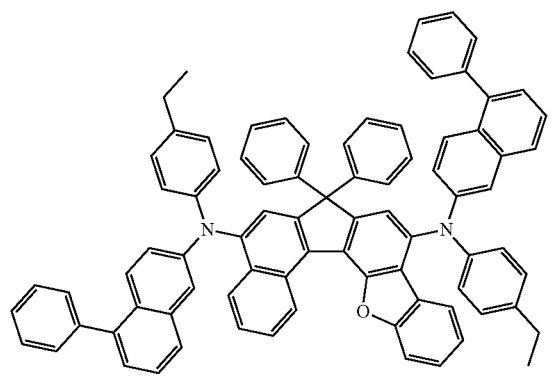
<Chemical Formula 180>
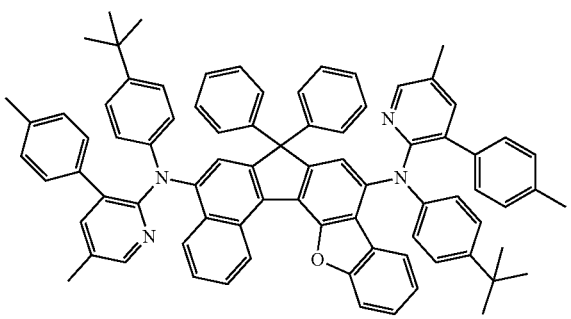
<Chemical Formula 181>
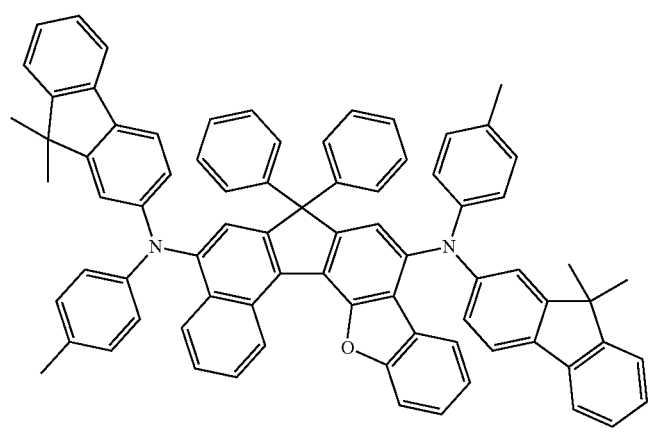

<Chemical Formula 182>
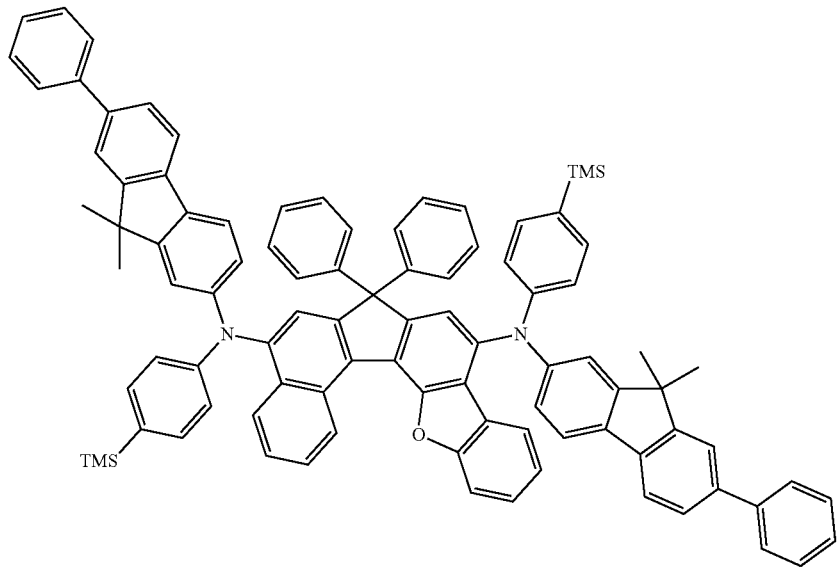
<Chemical Formula 183>
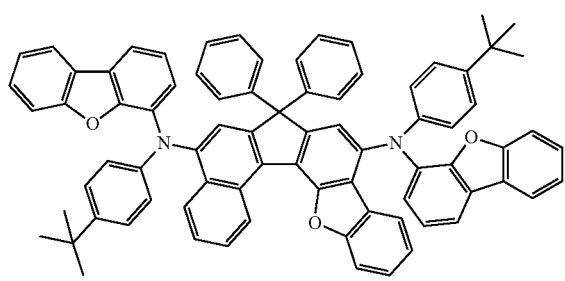
<Chemical Formula 184>
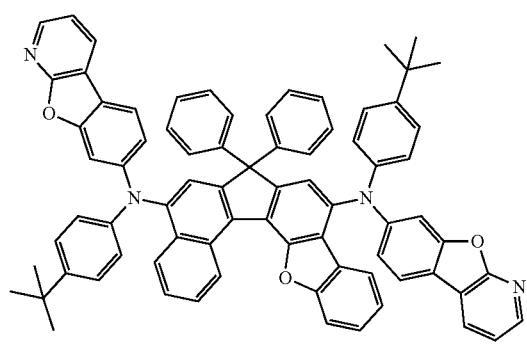
<Chemical Formula 185>
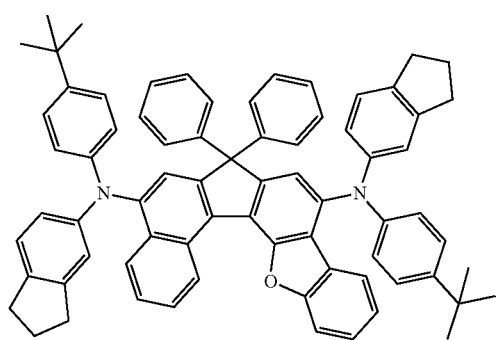
<Chemical Formula 186>
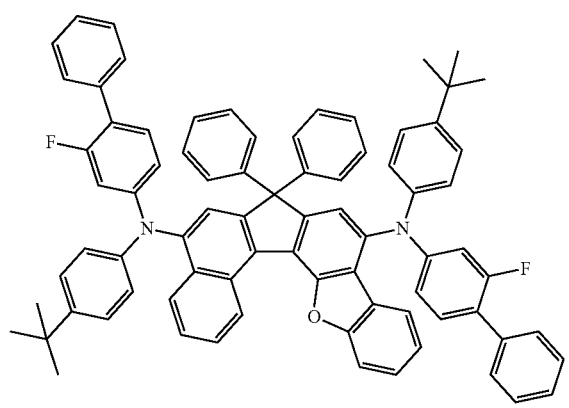

-continued
<Chemical Formula 187>
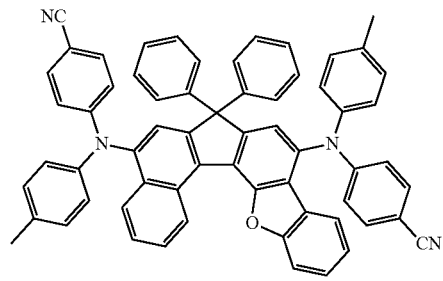
<Chemical Formula 188>
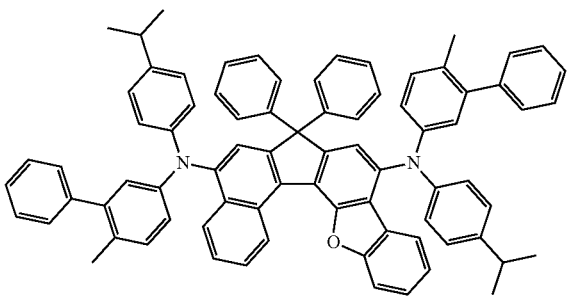
<Chemical Formula 189>
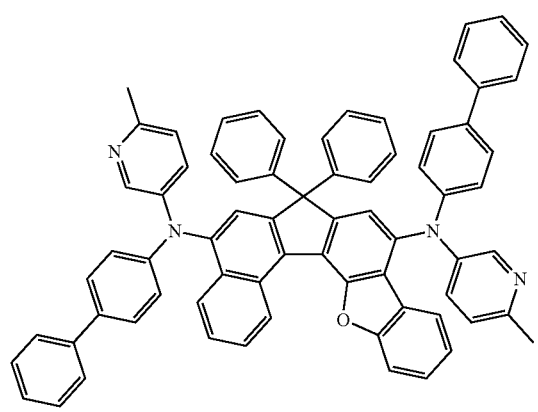
<Chemical Formula 190>
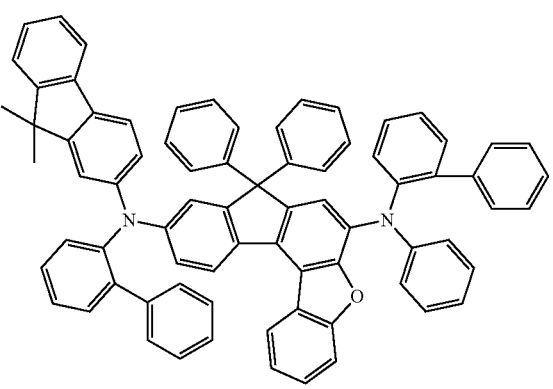
<Chemical Formula 191>
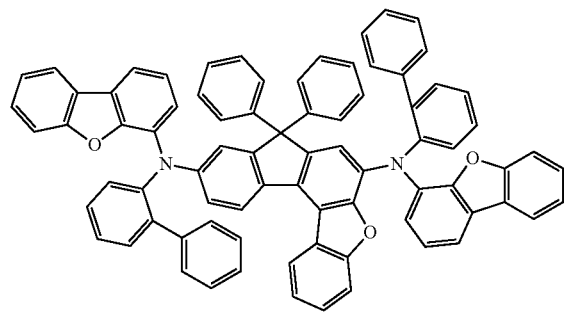
<Chemical Formula 192>
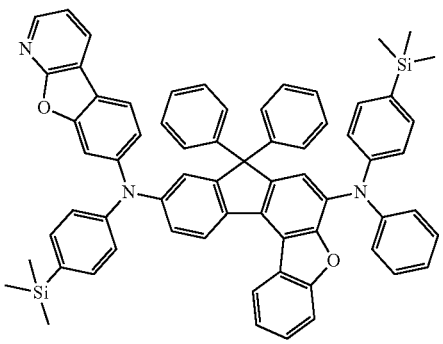
<Chemical Formula 193>
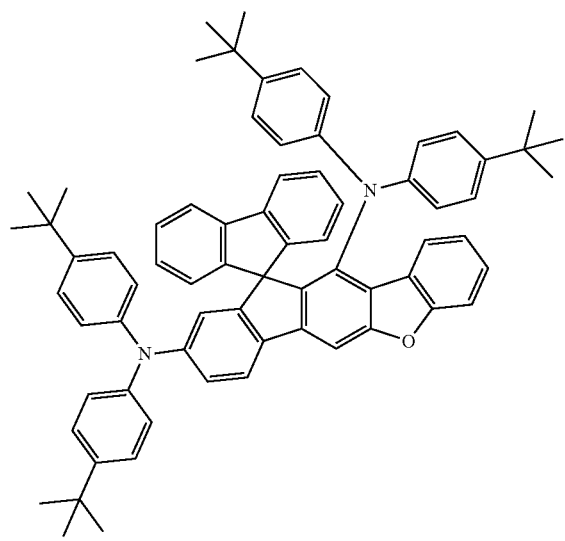
<Chemical Formula 194>
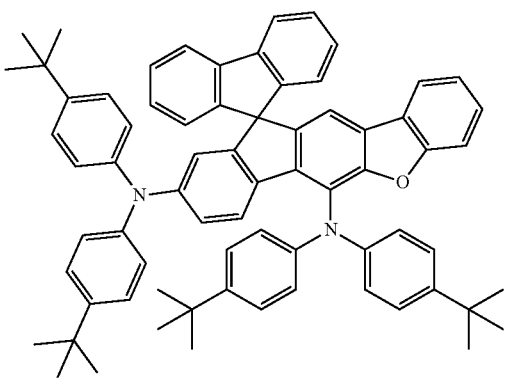

<Chemical Formula 195>
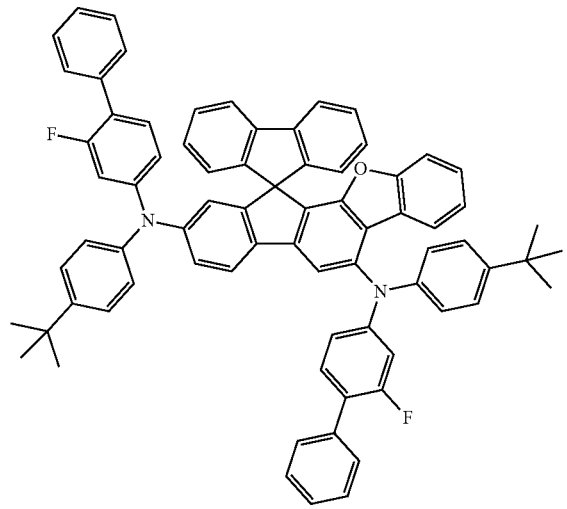
<Chemical Formula 196>
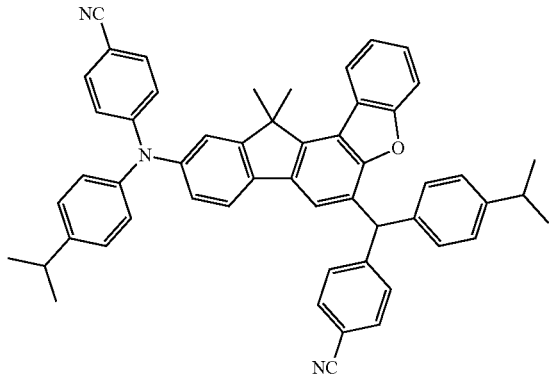
<Chemical Formula 197>
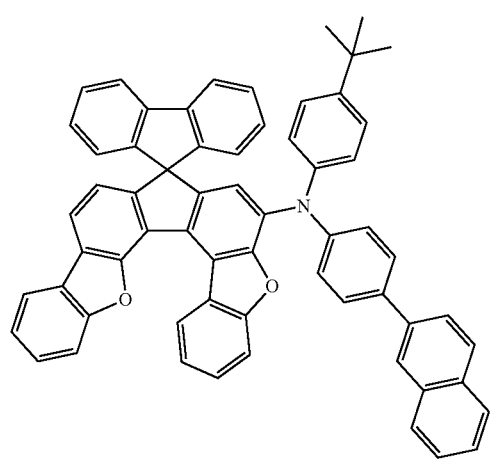
<Chemical Formula 198>
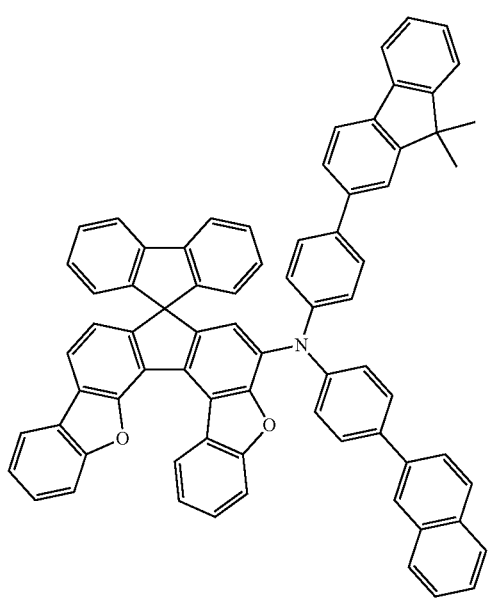

<Chemical Formula 199>
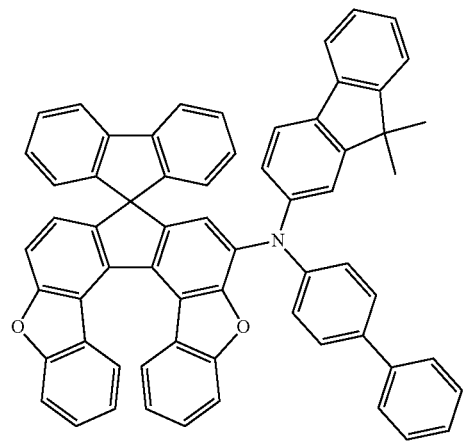
<Chemical Formula 200>
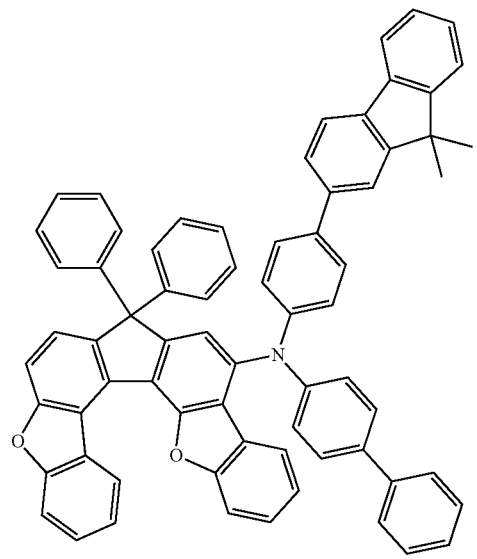
<Chemical Formula 201>
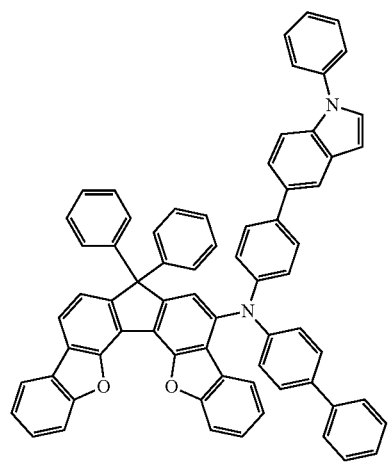
<Chemical Formula 202>
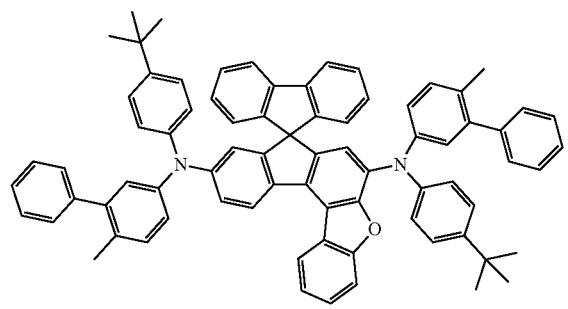
<Chemical Formula 203>
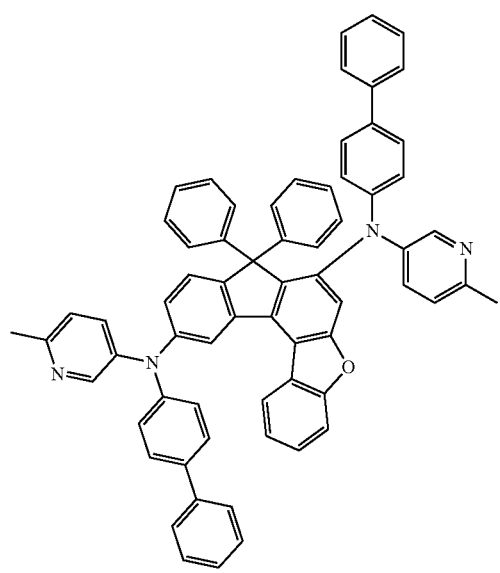
<Chemical Formula 204>
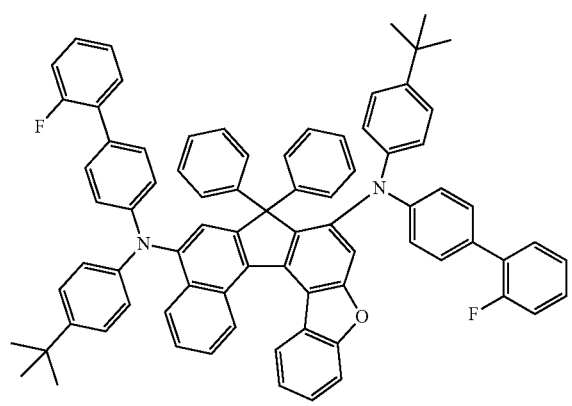

<Chemical Formula 205>
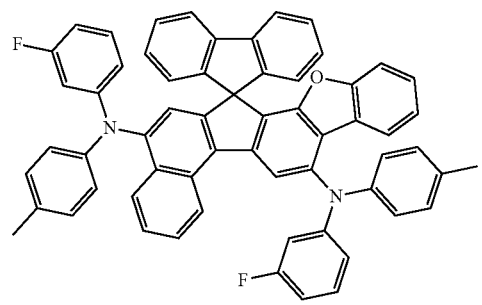
<Chemical Formula 206>
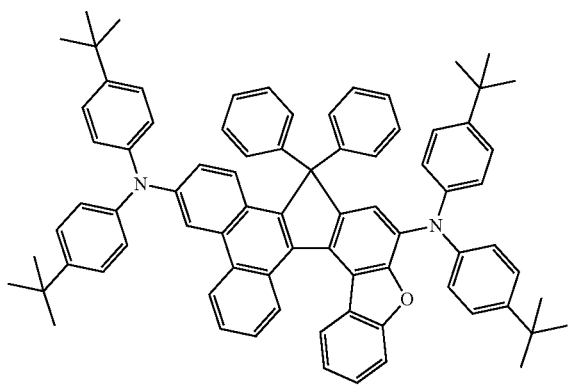
<Chemical Formula 207>
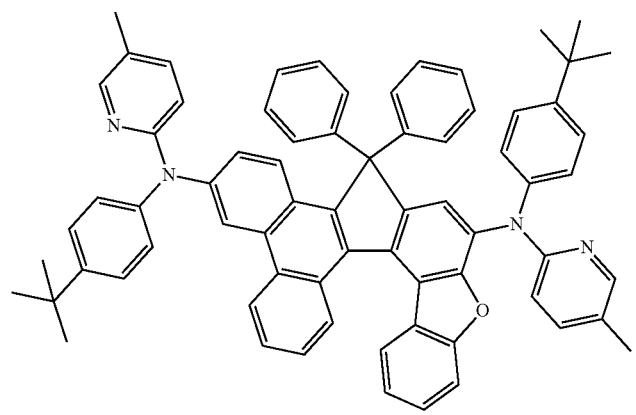
<Chemical Formula 208>
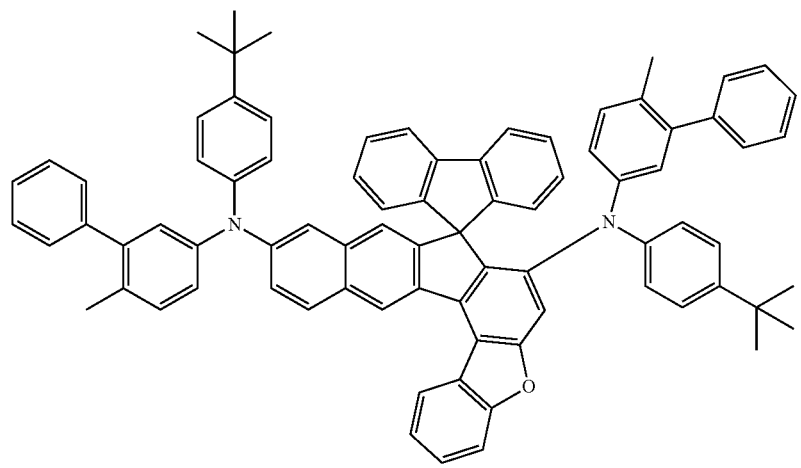

<Chemical Formula 209>
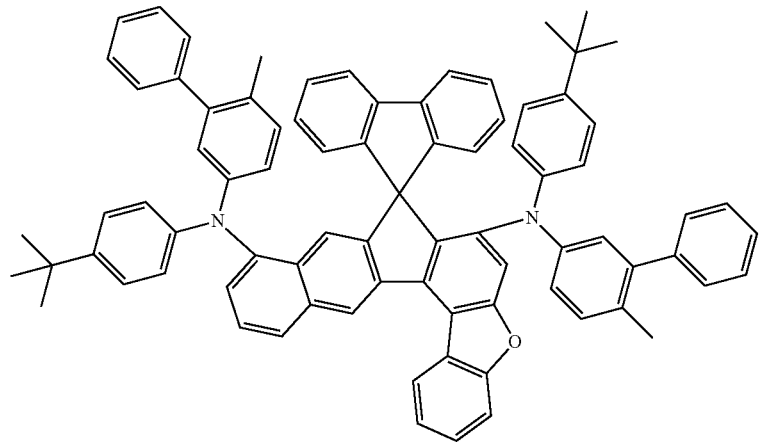
<Chemical Formula 210>
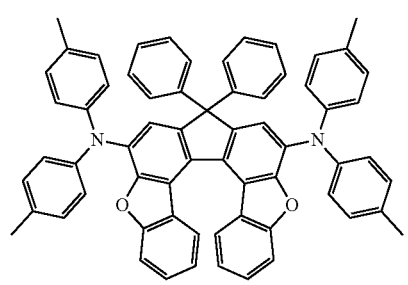
<Chemical Formula 211>
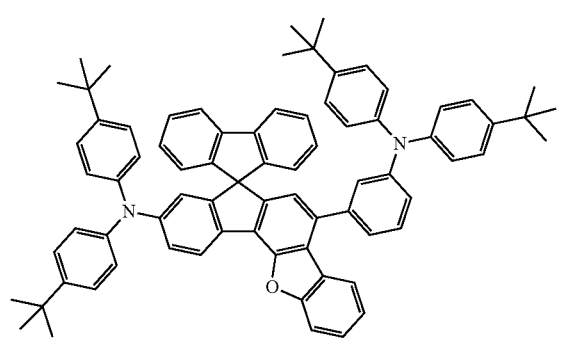
<Chemical Formula 212>
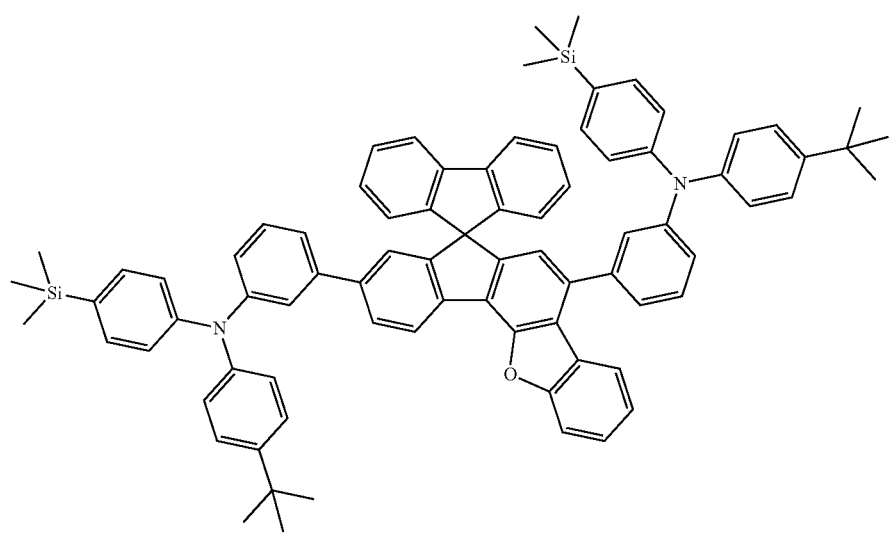

-continued
<Chemical Formula 213>
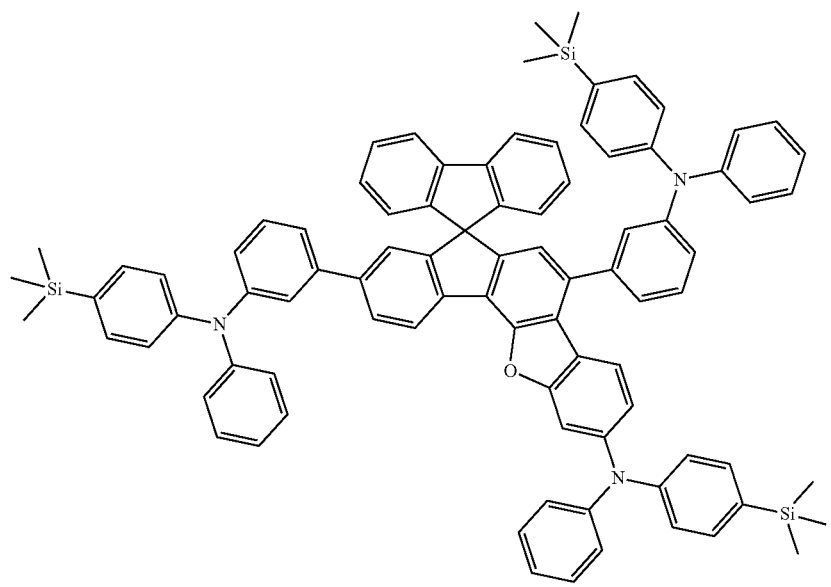
<Chemical Formula 214>
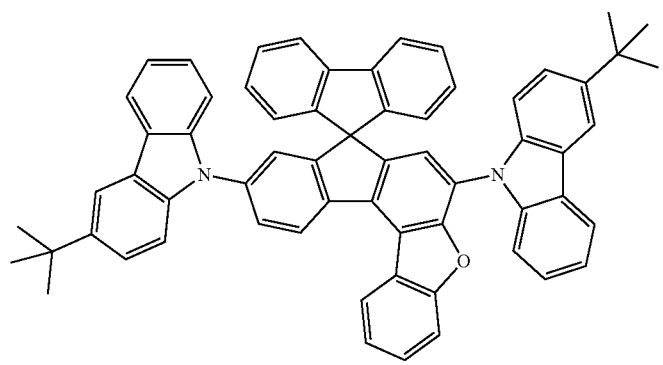
<Chemical Formula 215>
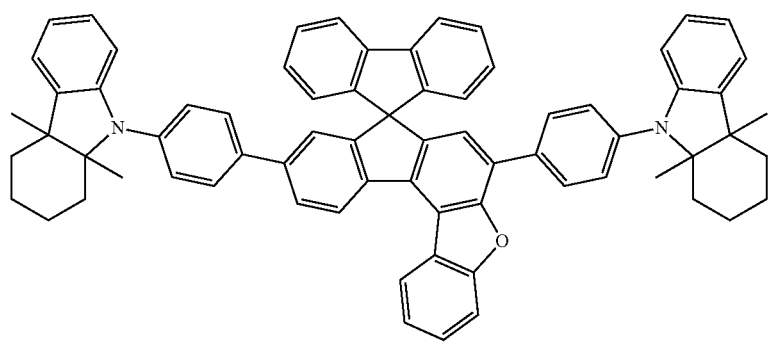
<Chemical Formula 216>
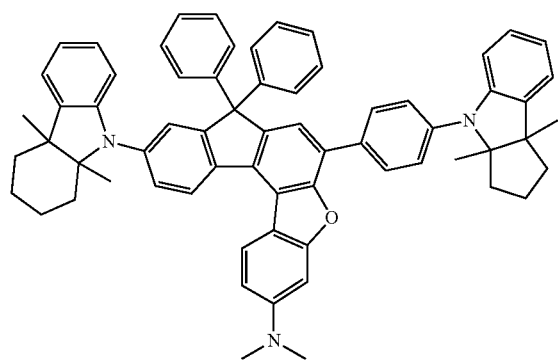
<Chemical Formula 217>
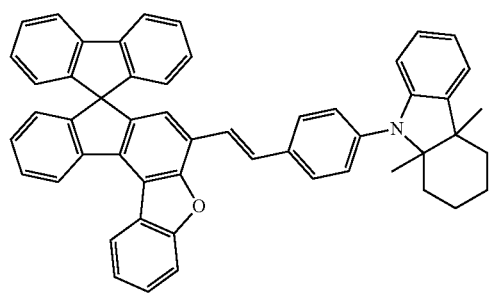

-continued
<Chemical Formula 218>
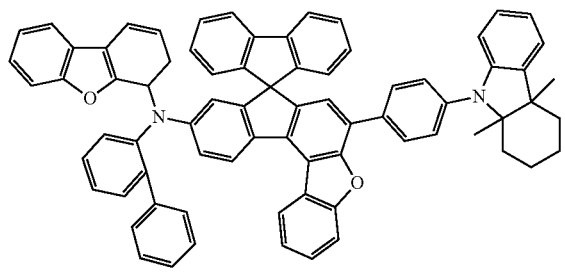
<Chemical Formula 219>
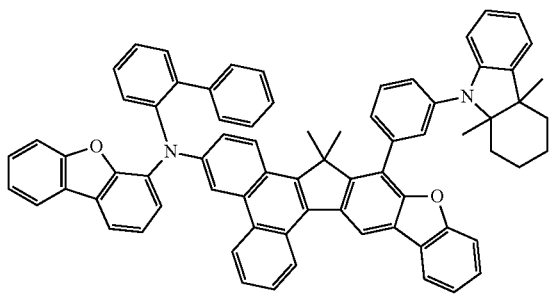
<Chemical Formula 220>
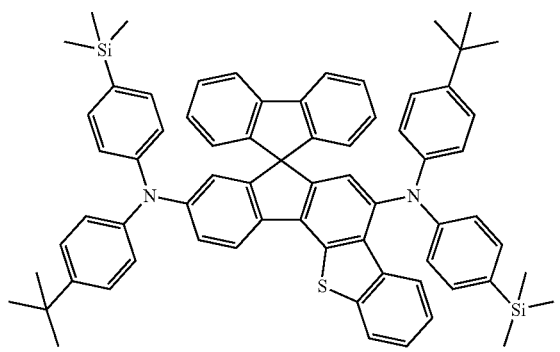
<Chemical Formula 221>
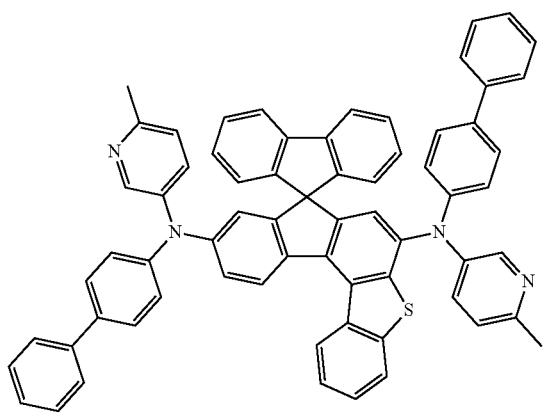
<Chemical Formula 222>
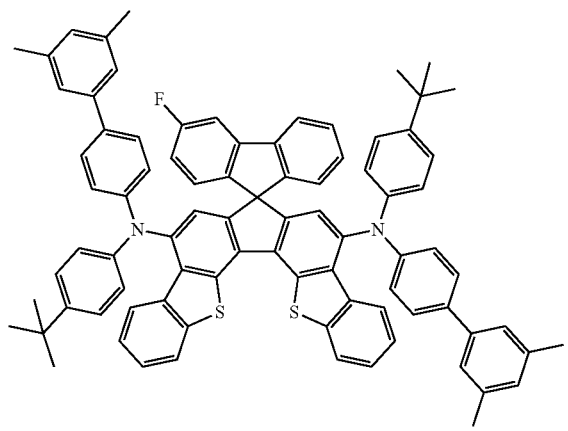
<Chemical Formula 223>
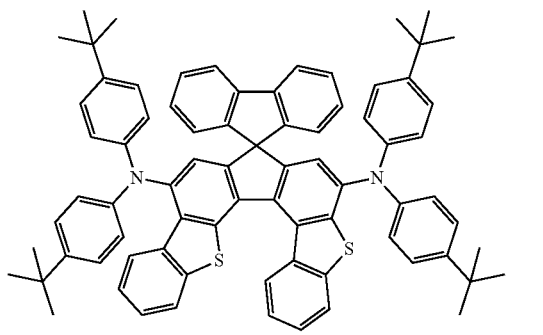
<Chemical Formula 224>
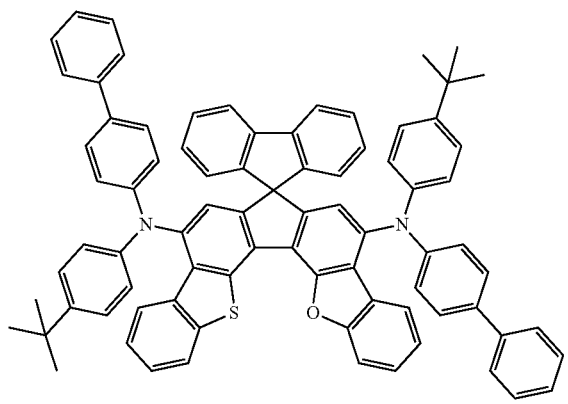
<Chemical Formula 225>
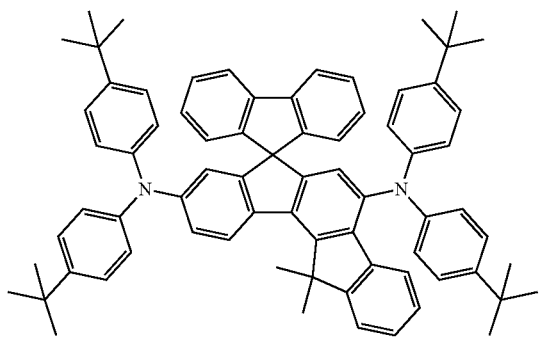

<Chemical Formula 226>
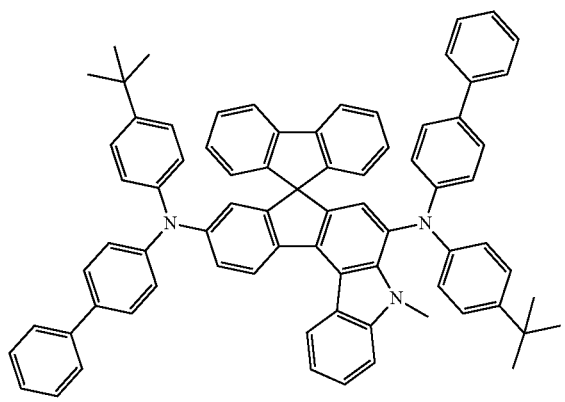
<Chemical Formula 227>
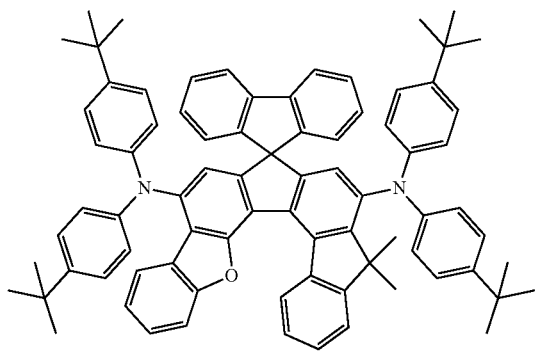
<Chemical Formula 228>
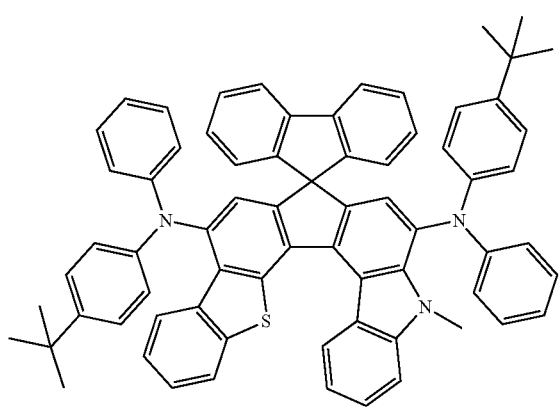
<Chemical Formula 229>
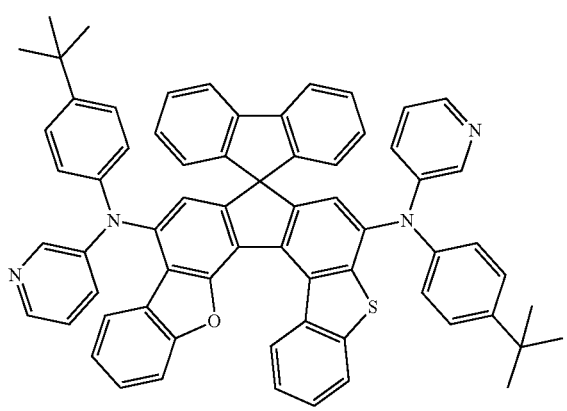
<Chemical Formula 230>
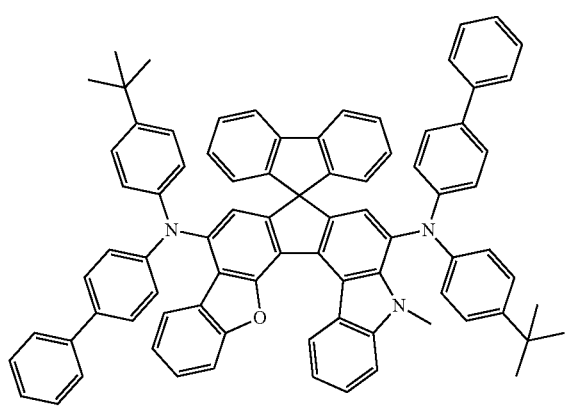
<Chemical Formula 231>
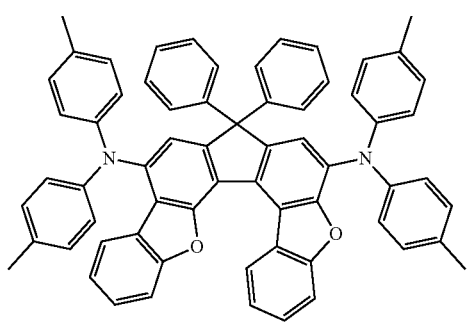

-continued
<Chemical Formula 232>
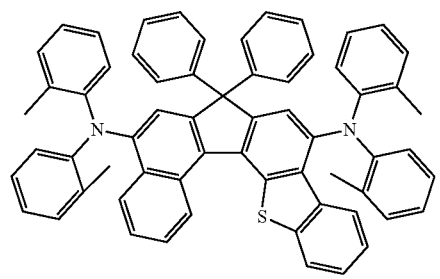
<Chemical Formula 233>
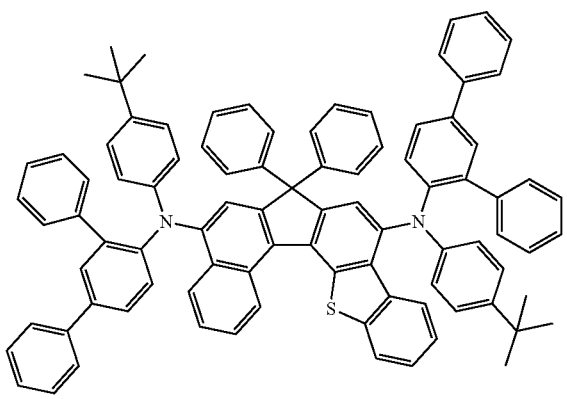
<Chemical Formula 234>
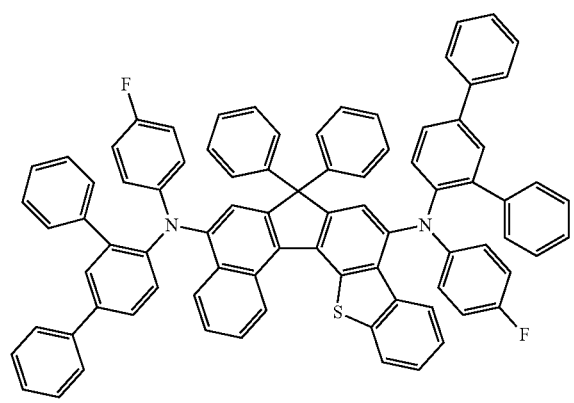
<Chemical Formula 235>
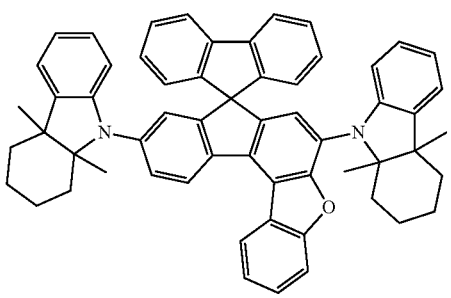
<Chemical Formula 236>
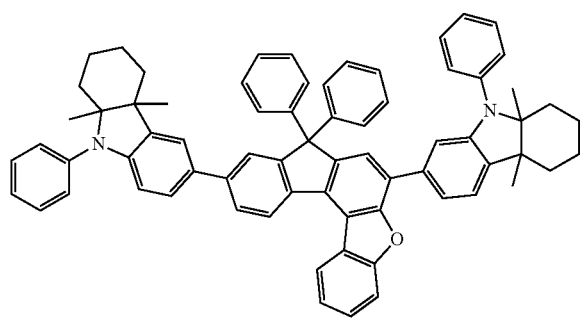
<Chemical Formula 237>
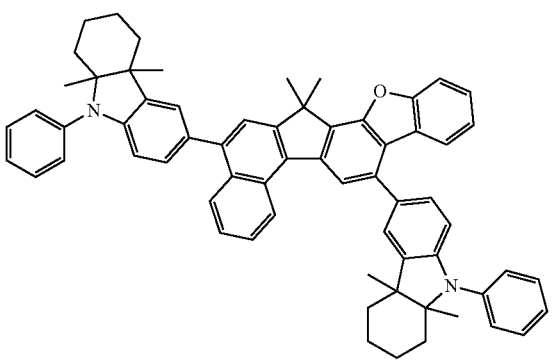

<Chemical Formula 238>

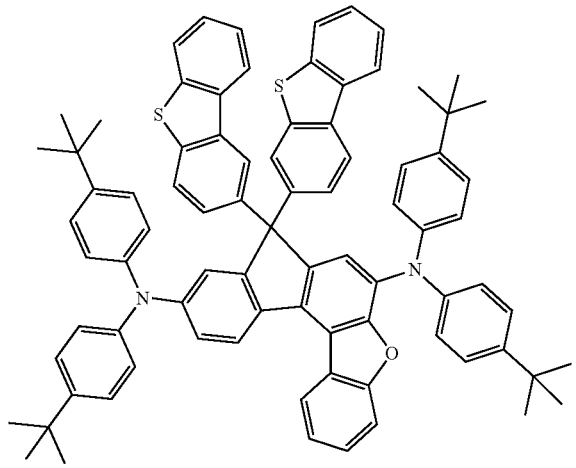

<Chemical Formula 239>

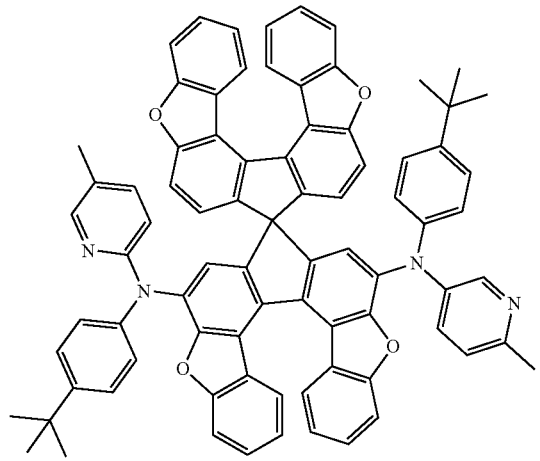

In some embodiments of the present disclosure, the substituents Ar$_{21}$ to Ar$_{23}$ on the compound represented by Chemical Formula C may be the same or different and may each be a substituted or unsubstituted aryl of 6 to 20 carbon atoms, wherein one or two of Ar$_{21}$ to Ar$_{23}$ may be the substituent represented by Structural Formula A wherein t may be 1 or 2.

In some embodiment of the present disclosure, the linker L$_{21}$ of Chemical Formula C may be a single bond or a substituted or unsubstituted arylene of 6 to 20 carbon atoms.

The compound of Chemical Formula C may be exemplified by, but is not limited to, the following [Compound 1] to [Compound 48].

[Cpd. 1]

[Cpd. 2]

[Cpd. 3]

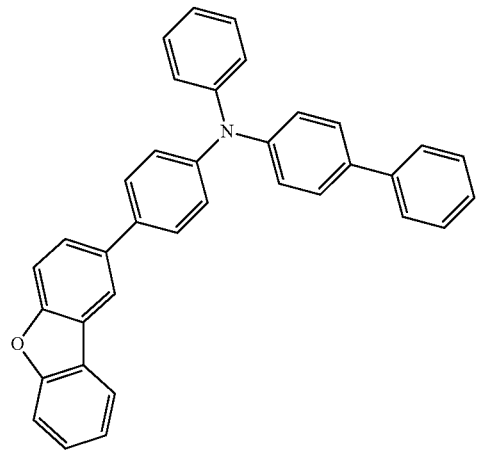

[Cpd. 4]

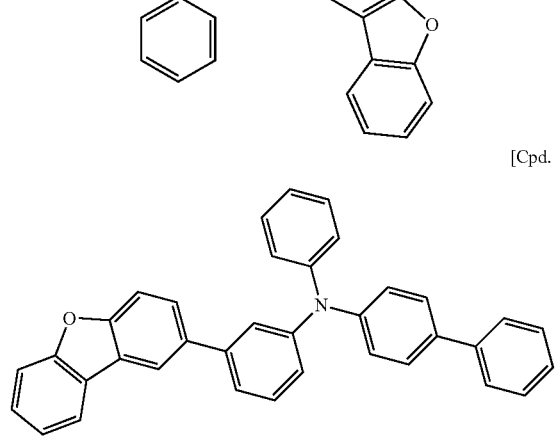

-continued
[Cpd. 5]
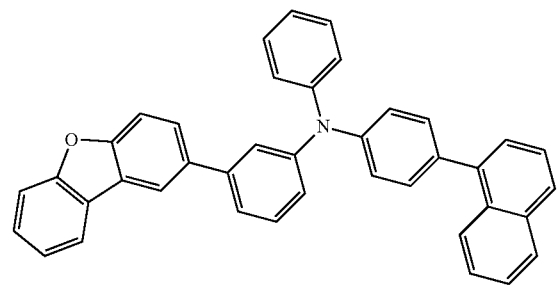
[Cpd. 6]
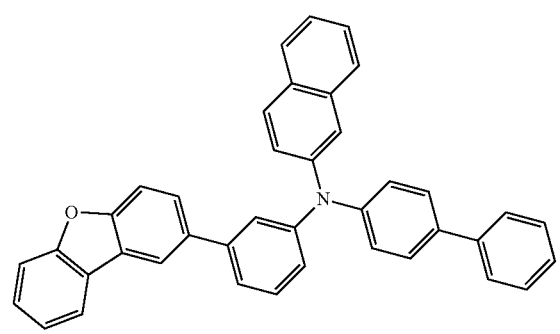
[Cpd. 7]
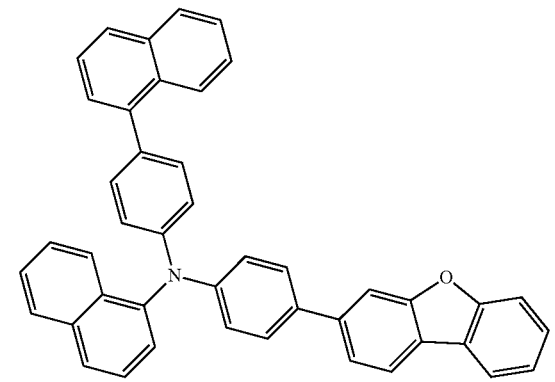
[Cpd. 8]
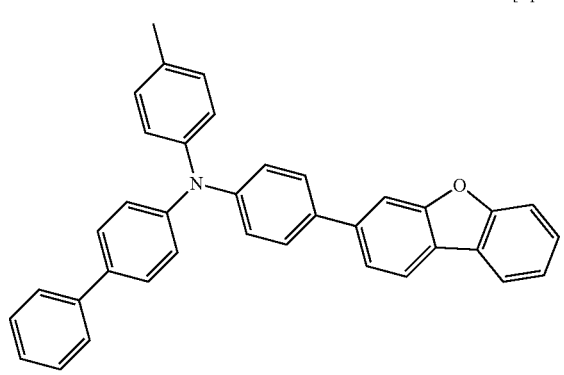
[Cpd. 9]
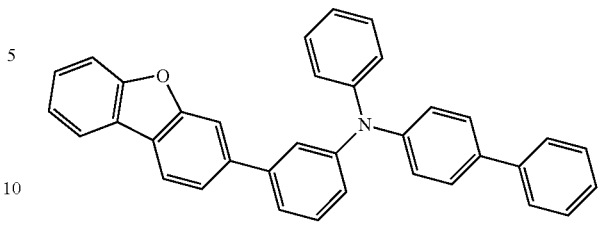
[Cpd. 10]
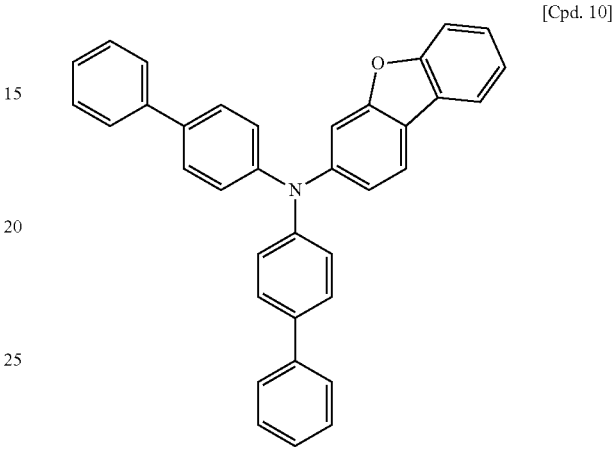
[Cpd. 11]
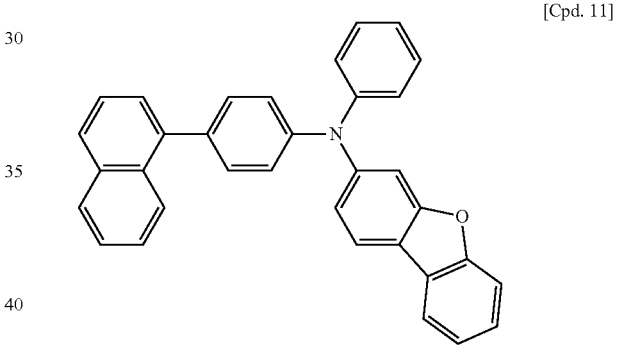
[Cpd. 12]
[Cpd. 13]
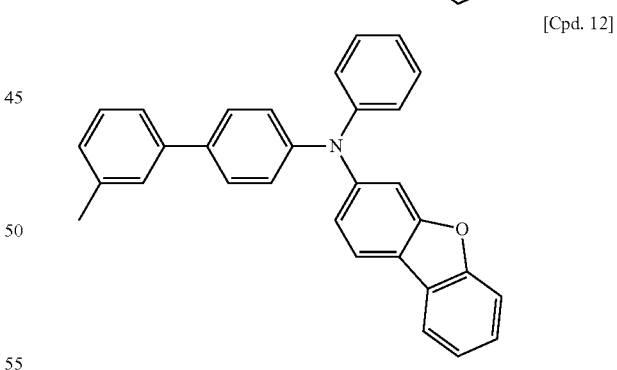

[Cpd. 14]
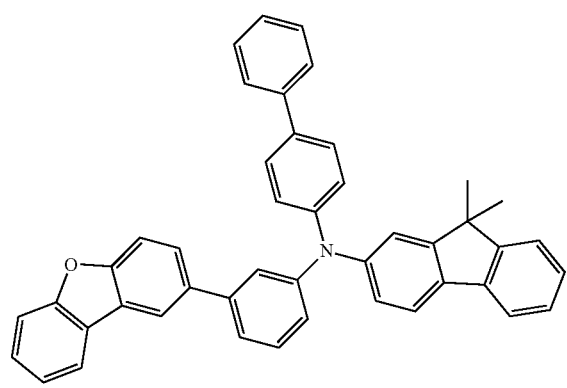
[Cpd. 15]
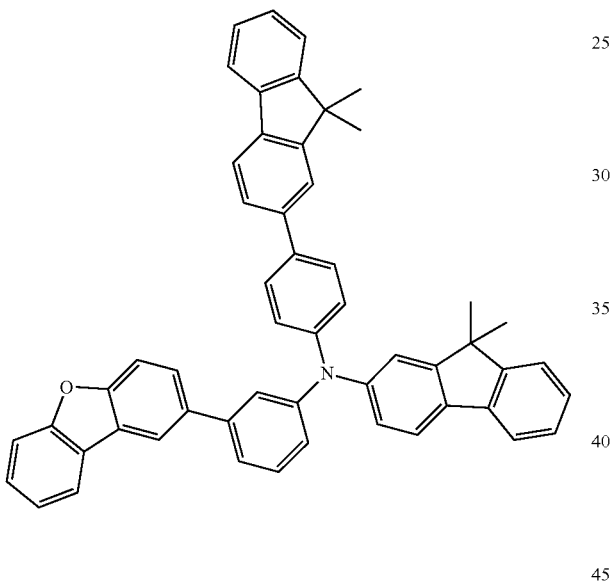
[Cpd. 16]
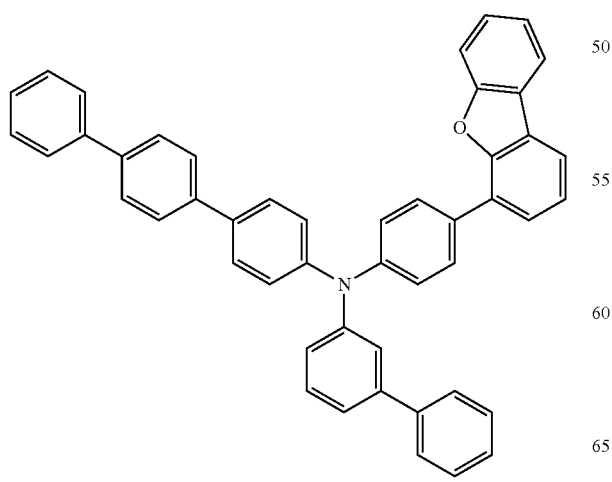
[Cpd. 17]
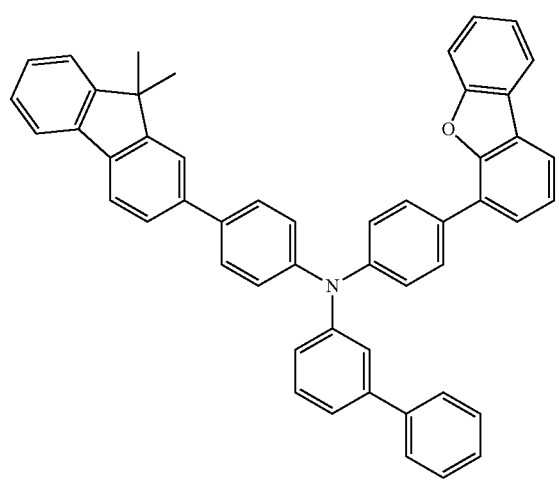
[Cpd. 18]
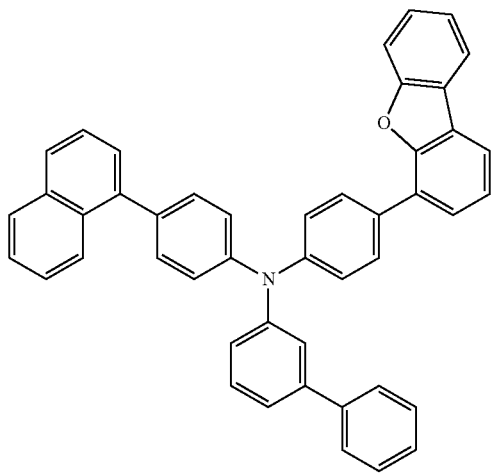
[Cpd. 19]
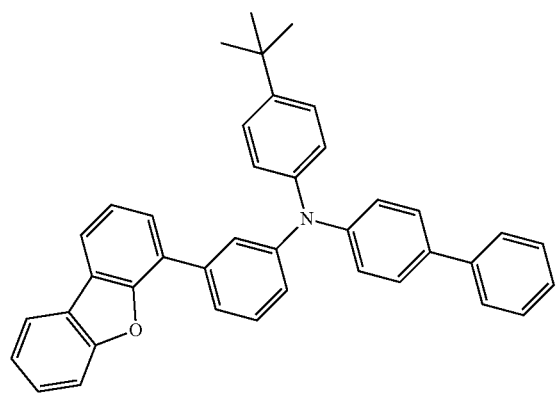

[Cpd. 20]
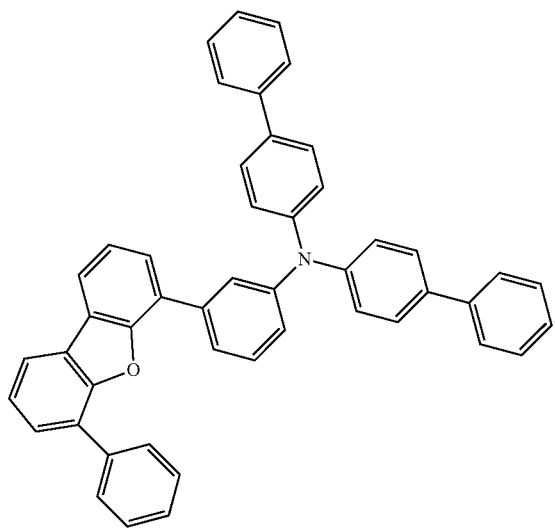
[Cpd. 21]
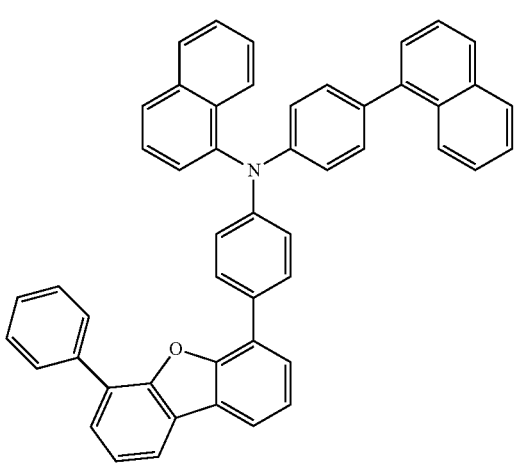
[Cpd. 22]
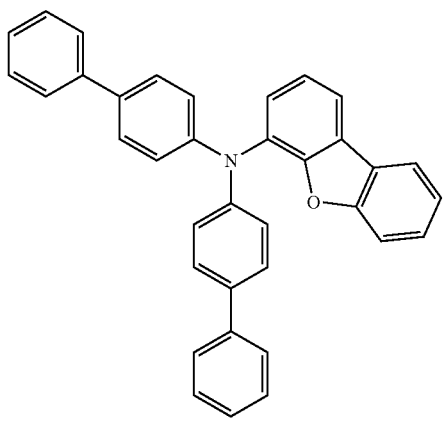
[Cpd. 23]
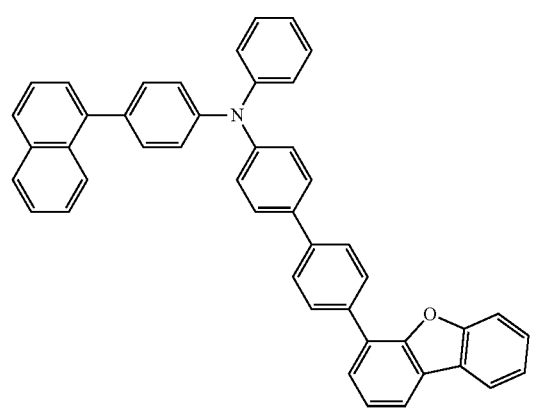
[Cpd. 24]
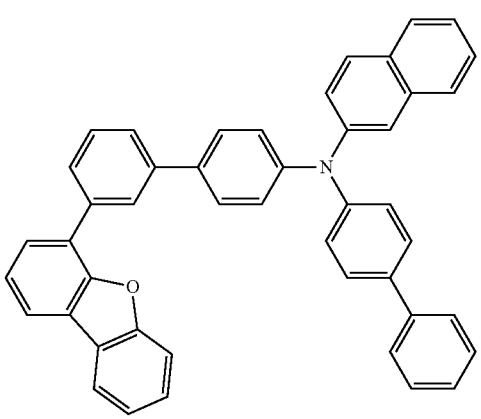
[Cpd. 25]
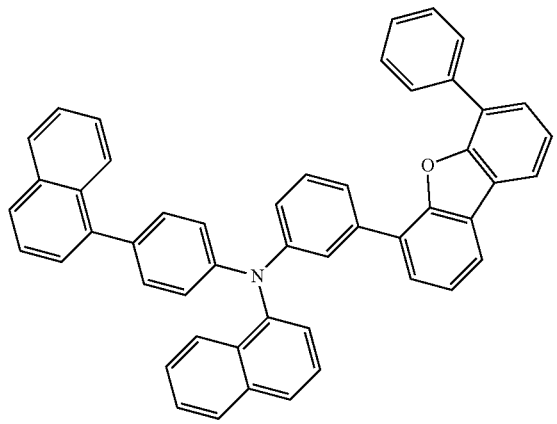

[Cpd. 26]
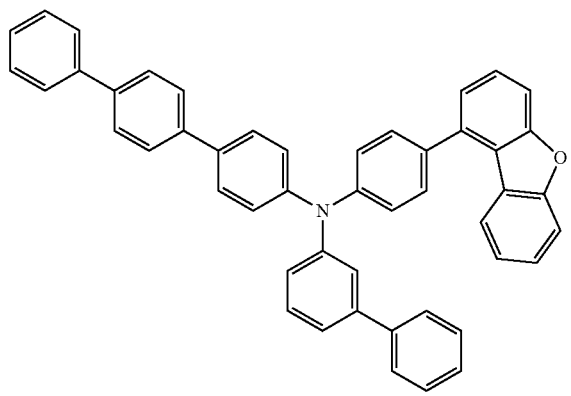
[Cpd. 27]
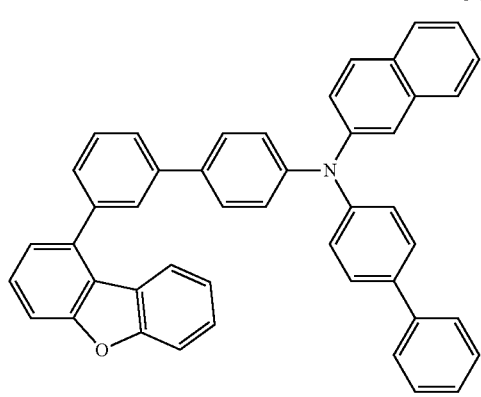
[Cpd. 28]
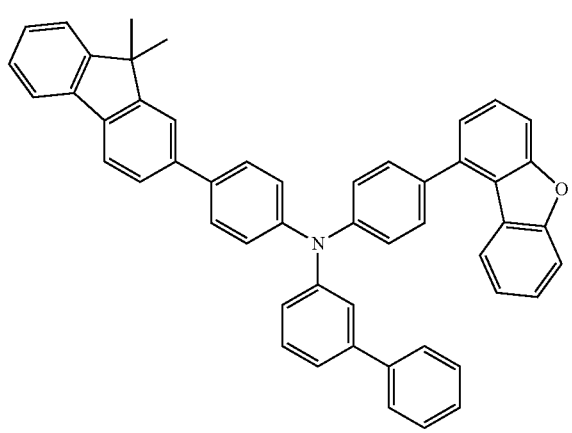
[Cpd. 29]
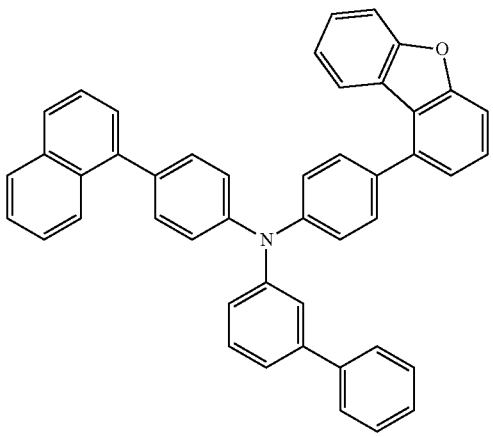
[Cpd. 30]
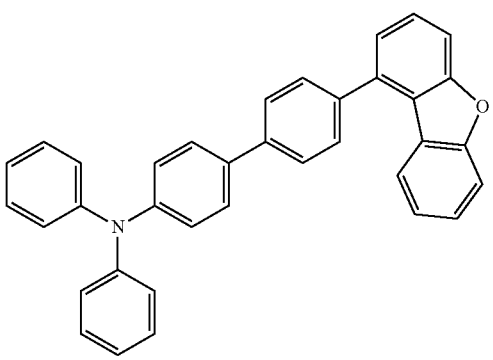
[Cpd. 31]
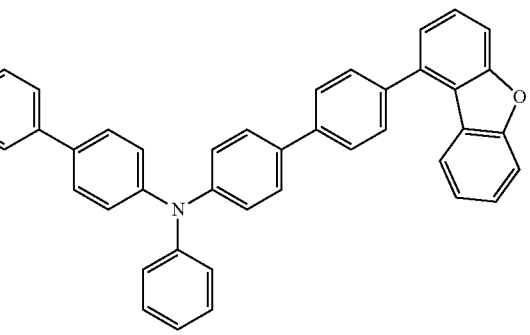
[Cpd. 32]
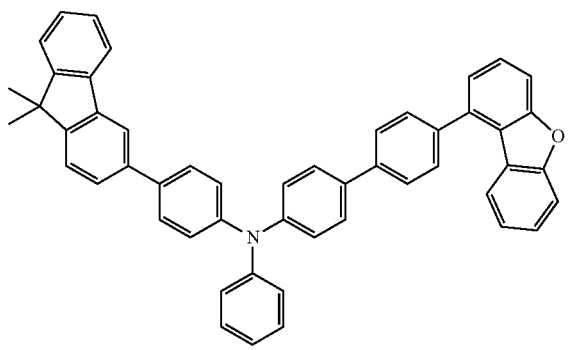

[Cpd. 33]
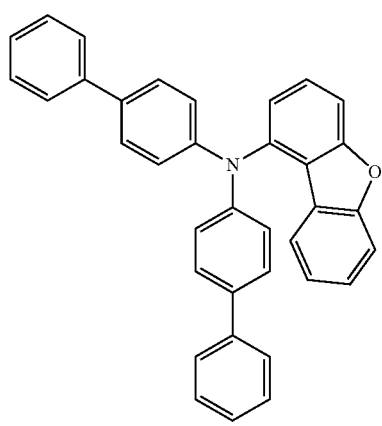
[Cpd. 36]
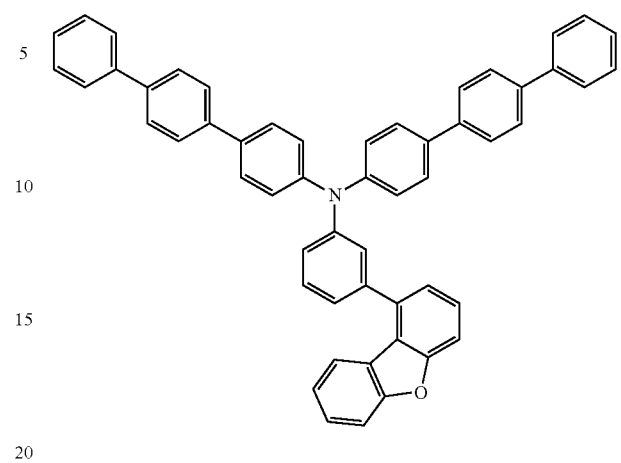
[Cpd. 34]
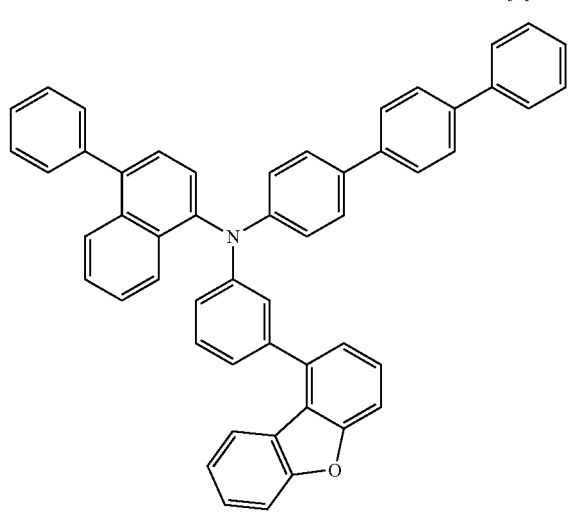
[Cpd. 37]
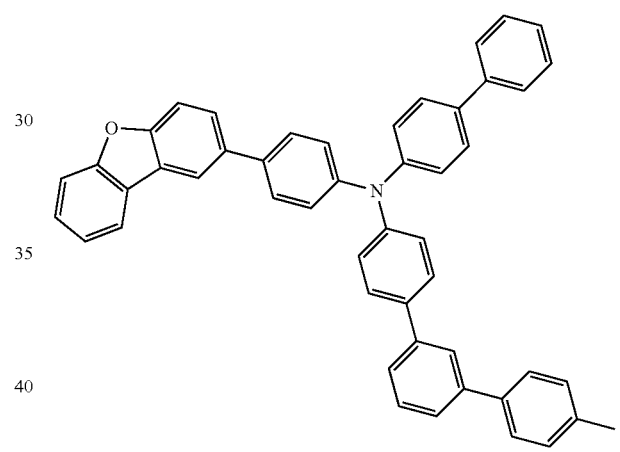
[Cpd. 35]
[Cpd. 38]
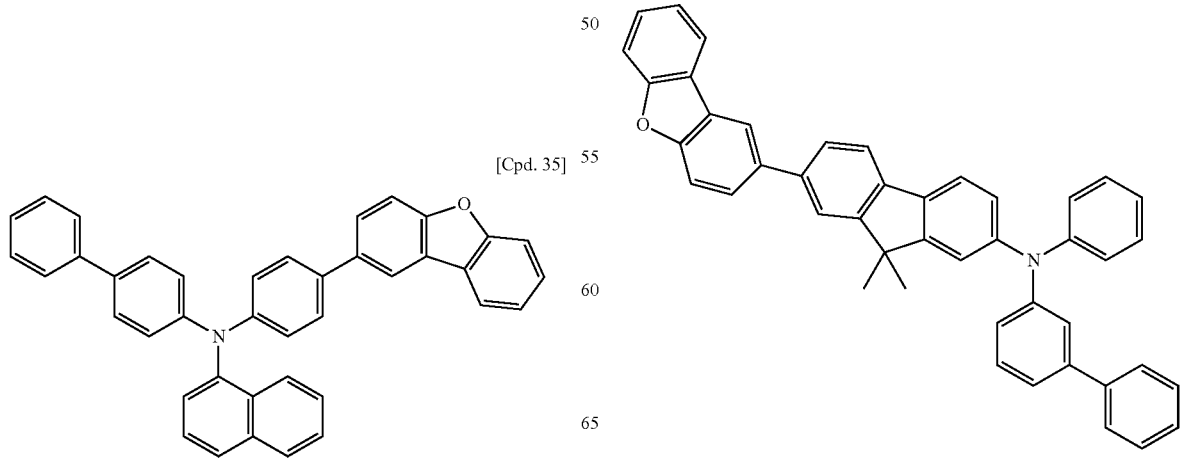

[Cpd. 39]
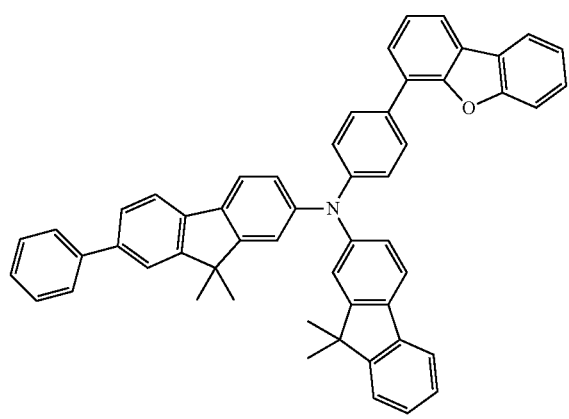
[Cpd. 40]
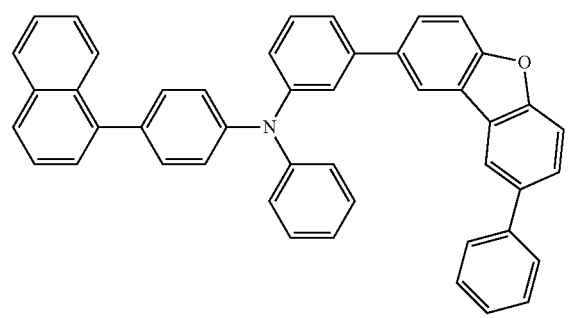
[Cpd. 41]
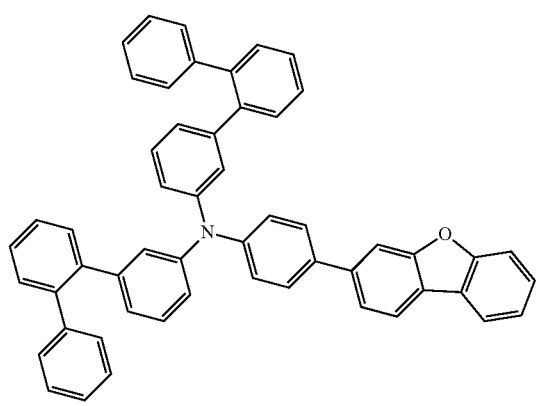
[Cpd. 42]
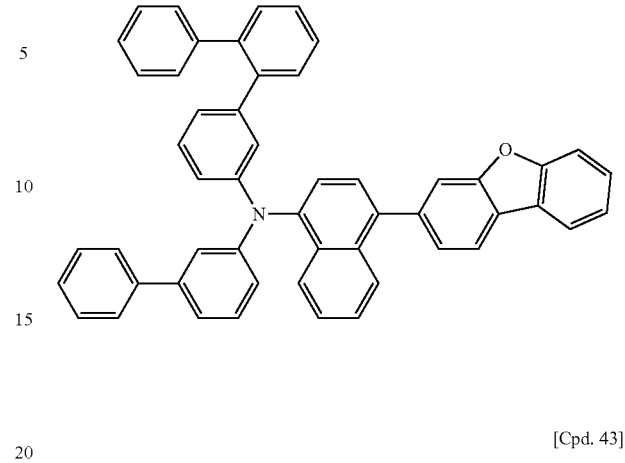
[Cpd. 43]
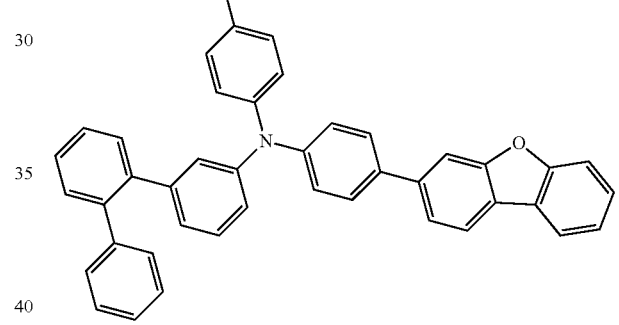
[Cpd. 44]
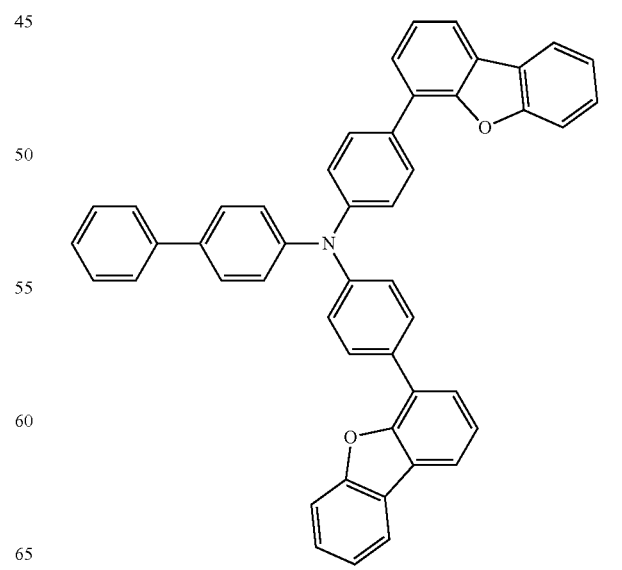

[Cpd. 45]

[Cpd. 46]

[Cpd. 47]

[Cpd. 48]

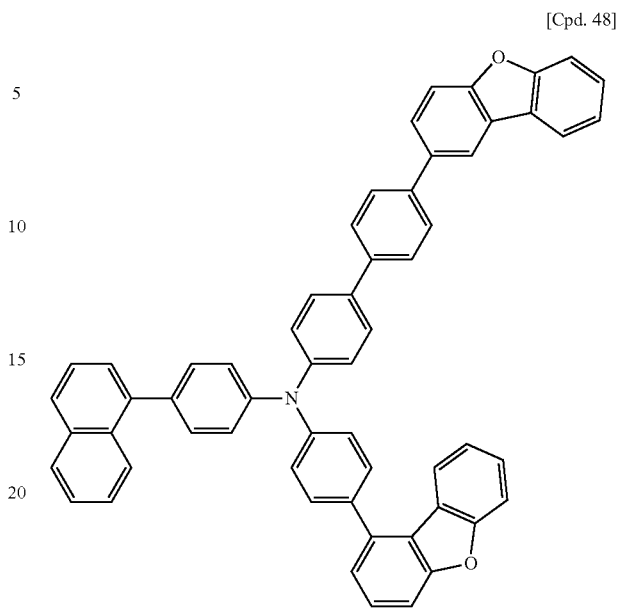
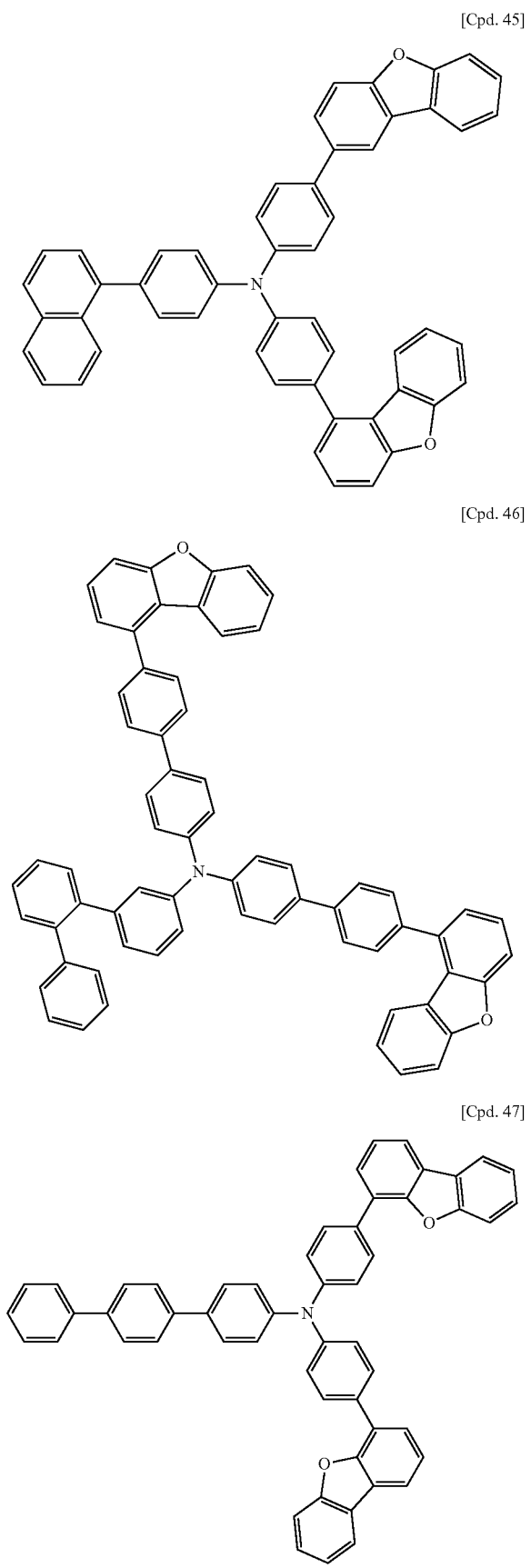

The light-emitting layer of the organic light-emitting diode according to the present disclosure includes a host and a dopant.

In this regard, the amine compounds represented by Chemical Formula A and B serve as the dopant while the electron-blocking layer as a constituent of the organic light-emitting diode comprises the compound represented by Chemical Formula C.

The organic light-emitting diode according to the present disclosure in which the amine compounds represented by Chemical Formulas A and B serve as dopants in the light-emitting layer while the compound represented by Chemical Formula C is used in the electron-blocking layer exhibits higher efficiency than those of the conventional art.

Generally, an electron-blocking layer (EBL) is introduced between a light-emitting layer and a hole transport layer in an organic light-emitting diode in order to prevent electrons from being injected into the hole transport layer without combination in the light-emitting layer and to retain electrons within the light-emitting layer, thereby enhancing the recombination of electrons with holes.

Suitable for use in an electron-blocking layer is a material that can function to transport holes, but does not readily delivers electrons. When the hole transport layer transports holes well and the electron-blocking layer (EBL) effectively performs its function, the organic electroluminescent device can operate at low voltages with enhanced luminous efficiency and luminance as well as a prolonged lifetime. In the present disclosure, the compound of Chemical Formula C is used in the electron-blocking layer while the amine compounds of Chemical Formulas A and B serve as dopants in the light-emitting layer.

According to some embodiments of the present disclosure, the host compound as a constituent of the light-emitting layer may include at least one compound represented by the following Chemical Formula H, but is not limited thereto:

[Chemical Formula H]

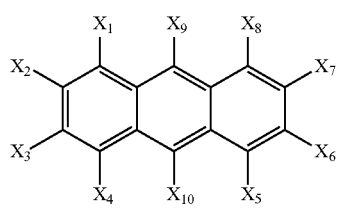

wherein, $X_1$ to $X_{10}$ may be the same or different, and are each independently selected from the group consisting of a hydrogen atom, a deuterium atom, a substituted or unsubstituted alkyl of 1 to 30 carbon atoms, a substituted or unsubstituted alkenyl of 2 to 30 carbon atoms, a substituted or unsubstituted cycloalkyl of 3 to 30 carbon atoms, a substituted or unsubstituted cycloalkenyl of 5 to 30 carbon atoms, a substituted or unsubstituted alkoxy of 1 to 30 carbon atoms, a substituted or unsubstituted aryloxy of 6 to 30 carbon atoms, a substituted or unsubstituted alkylthioxy of 1 to 30 carbon atoms, a substituted or unsubstituted arylthioxy of 6 to 30 carbon atoms, a substituted or unsubstituted alkylamine of 1 to 30 carbon atoms, a substituted or unsubstituted arylamine of 6 to 30 carbon atoms, a substituted or unsubstituted aryl of 6 to 50 carbon atoms, a substituted or unsubstituted heteroaryl of 3 to 50 carbon atoms containing O, N or S as a heteroatom, a substituted or unsubstituted silicone, a substituted or unsubstituted boron, a substituted or unsubstituted silane, a carbonyl, a phosphoryl, an amino, a nitrile, a hydroxyl, a nitro, a halogen, an amide, and an ester wherein two adjacent ones may form a fused, aliphatic, aromatic, heteroaliphatic or heteroaromatic ring.

In accordance with a preferred aspect thereof, the present disclosure addresses an organic light-emitting diode, comprising a first electrode; a second electrode facing the first electrode; and an electron-blocking layer and a light-emitting layer sequentially interposed between the first electrode and the second electrode, wherein the light-emitting layer comprises at least one of the amine compounds represented by Chemical Formula A or B as a dopant, and the electron-blocking layer comprises at least one of the compounds represented by Chemical Formula C.

In some embodiments of the present disclosure, the content of the dopant in the light-emitting layer may range from about 0.01 to 20 parts by weight based on 100 parts by weight of the host, but is not limited thereto.

Also, the light-emitting layer may further comprise various dopant and host materials in addition to the dopant and the host.

A combination of the dopant suitably selected from the amine compounds represented by Chemical Formula A and B in the light-emitting layer and the compound represented by Chemical Formula C in the electron-blocking layer enables high luminous efficiency of the diode.

Also, the organic light-emitting diode of the present disclosure may further comprise at least one selected from among a hole injection layer, a hole transport layer, an electron transport layer, and an electron injection layer in addition to the electron-blocking layer and the light-emitting layer.

Below, a description will be given of the organic light-emitting diode of the present disclosure, with reference to FIGURE.

FIGURE is a schematic cross-sectional view of the structure of an organic light-emitting diode according to some embodiments of the present disclosure.

As shown in FIGURE, the organic light-emitting diode has a structure in which a hole transport layer is interposed between a first electrode and a light-emitting layer and an electron transport layer is interposed between the light-emitting layer and a second electrode; that is, the organic light-emitting diode comprises an anode 20, a hole transport layer 40, an electron-blocking layer 45, an organic light-emitting layer 50 comprising a host and a dopant, an electron transport layer 60, and a cathode 80, sequentially.

Optionally a hole injection layer 30 and an electron injection layer 70 may be interposed between the anode 20 and the hole transport layer 40 and between the light-emitting layer 50 and the cathode 80, respectively.

Reference is now made to FIGURE with regard to the fabrication of the organic light-emitting diode of the present disclosure.

First, a substrate 10 is coated with an anode electrode material to form an anode 20. So long as it is used in a typical organic EL device, any substrate may be taken as the substrate 10. Preferable is an organic substrate or a transparent plastic substrate that exhibits excellent transparency, surface smoothness, ease of handling, and waterproofness. As the anode electrode material, indium tin oxide (ITO), indium zinc oxide (IZO), tin oxide ($SnO_2$), or zinc oxide (ZnO) may be used owing to their high transparency and electroconductivity.

A hole injection layer material is applied on the anode electrode 20 by thermal deposition in a vacuum or by spin coating to form a hole injection layer 30. Subsequently, thermal deposition in a vacuum or spin coating of a hole transport layer material may also be conducted to form a hole transport layer 40 on the hole injection layer 30.

No particular limitations are imposed on the hole injection layer material, as long as it is typically used in the art. As examples, mention may be made of 2-TNATA [4,4',4"-tris (2-naphthylphenyl-phenylamino)-triphenylamine], NPD [N,N'-di(1-naphthyl)-N,N'-diphenylbenzidine)], TPD [N,N'-diphenyl-N,N'-bis(3-methylphenyl)-1,1'-biphenyl-4,4'-diamine], and DNTPD [N,N'-diphenyl-N,N'-bis-[4-(phenyl-m-tolyl-amino)-phenyl]-biphenyl-4,4'-diamine].

So long as it is typically used in the art, any material may be selected for the hole transport layer without particular limitations. Examples include, but are not limited to, N,N'-bis(3-methylphenyl)-N,N'-diphenyl-[1,1-biphenyl]-4,4'-diamine (TPD) or N,N'-di(naphthalen-1-yl)-N,N'-diphenyl-benzidine (a-NPD).

In addition, the electron-blocking layer 45 may be formed on the hole transport layer 40 by subjecting the EBL material represented by Chemical Formula C to vacuum thermal deposition or spin coating. To form the electron-blocking layer 45, any compound that is well-known in the art may be used in combination with the organic compound of the present disclosure.

Then, a light-emitting layer 50 may be deposited on the electron-blocking layer 45 by deposition in a vacuum or by spin coating.

Here, the light-emitting layer may consist of a host and a dopant, and dopant and host materials are as mentioned above.

In some embodiments of the present disclosure, the light-emitting layer particularly ranges in thickness from 50 to 2,000 Å.

Thereafter, the electron transport layer 60 may be deposited on the light-emitting layer via vacuum deposition or spin coating, followed by forming the electron injection layer 70 on the electron transport layer 60 and then the cathode 80 on the electron injection layer 70, thereby fabricating an OLED.

So long as it functions to stably transport the electrons from the cathode, any known material may be used for the electron transport layer. Examples of the known electron transport material include quinoline derivatives, particularly tris(8-quinolinolate)aluminum (Alq3), Liq, TAZ, Balq, beryllium bis(benzoquinolin-10-oate: Bebq2), compound 201, compound 202, BCP, and the oxadiazole derivatives PBD, BMD, and BND, but are not limited thereto.

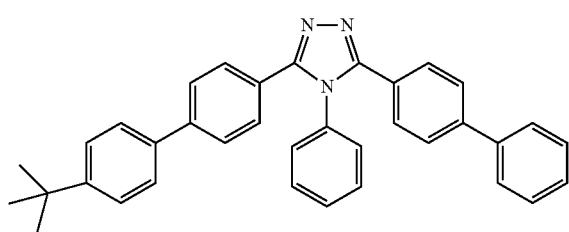

TAZ

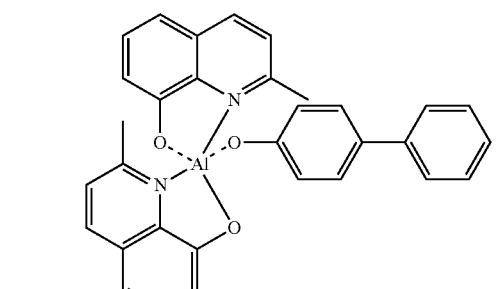

BAlq

<Cpd. 201>

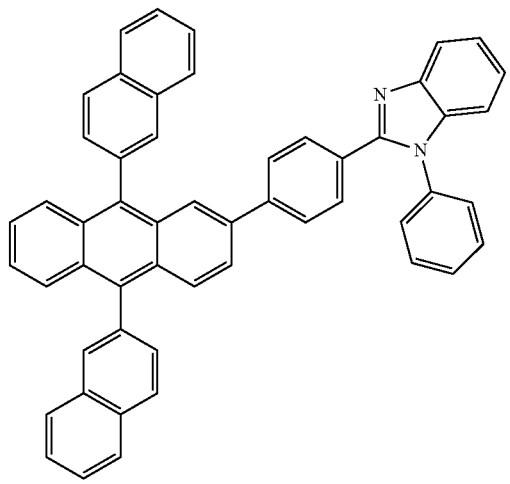

<Cpd. 202>

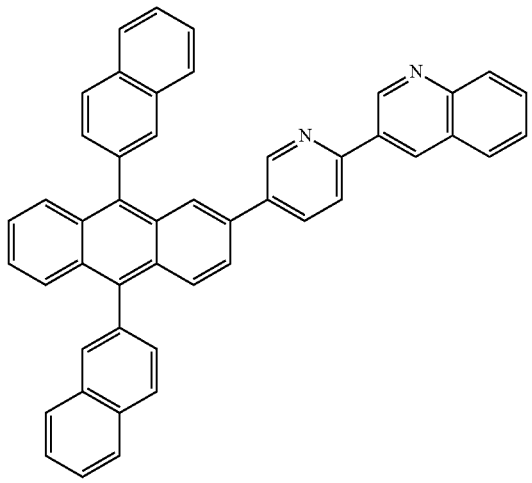

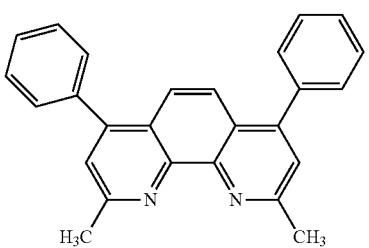

BCP

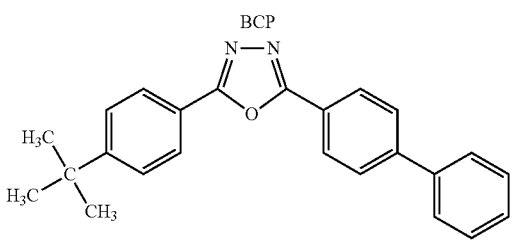

PBD

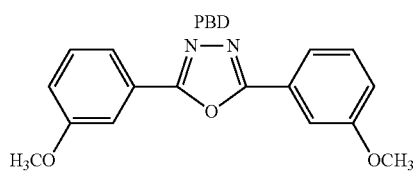

BMD

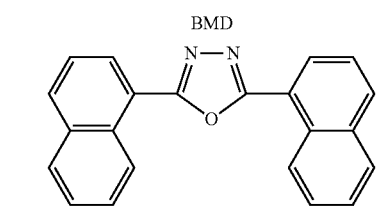

BND

As described above, an electron injection layer (EIL) is positioned on the electron transport layer in the organic light-emitting diode of the present disclosure. So long as it functions to facilitate the injection of electrons from the cathode, any known material may be available for forming the electron injection layer, without particular limitations.

By way of example, the material for the electron injection layer may be CsF, NaF, LiF, NaCl, $Li_2O$, or BaO. The conditions for depositing the electron injection layer are dependent on the compound that is employed, but may fall within the range of conditions for the formation of the hole injection layer.

The electron injection layer may range in thickness from about 1 Å to about 100 Å, and particularly from about 3 Å to about 90 Å. Given this thickness range, the electron injection layer can exhibit satisfactory electron injection properties without an actual increase in driving voltage.

The cathode may be made of a metal or metal alloy such as lithium (Li), magnesium (Mg), aluminum (Al), aluminum-lithium (Al—Li), calcium (Ca), magnesium-indium (Mg—In), and magnesium-silver (Mg—Ag). Alternatively, ITO or MO may be employed to form a transparent cathode for a top-emitting organic light-emitting diode.

In another embodiment, the light-emitting diode of the present disclosure may further comprise a light-emitting layer, made of a blue light-emitting material, a green light-emitting material, or a red light-emitting material, which can emit light in a wavelength range of 380 nm to 800 nm. That is, the light-emitting layer in the organic light-emitting diode of the present disclosure may have a multilayer structure in which the additional blue, green, and/or red light-emitting layer may be made of a fluorescent or phosphorescent material.

Further, one or more layers selected from among the above-mentioned layers may be deposited using a single molecule deposition process or a solution process.

Here, the deposition process is a process by which a material is vaporized in a vacuum or at a low pressure and deposited to form a layer, and the solution process is a method in which a material is dissolved in a solvent and applied for the formation of a thin film by means of inkjet printing, roll-to-roll coating, screen printing, spray coating, dip coating, spin coating, etc.

Also, the organic light-emitting diode of the present disclosure may be applied to a device selected from among flat display devices, flexible display devices, monochrome or white flat illumination devices, and monochrome or white flexible illumination devices.

A better understanding of the light-emitting diode according to the present disclosure may be obtained through the following examples which are set forth to illustrate, but are not to be construed as the limit of the present disclosure.

EXAMPLES

Synthesis Example 1: Synthesis of Compound of Chemical Formula 1

Synthesis Example 1-(1): Synthesis of Intermediate 1-a

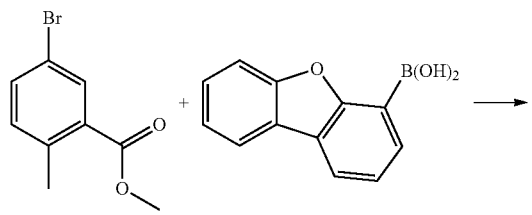

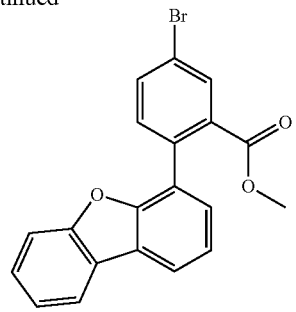

<Intermediate 1-a>

In a 500-mL round-bottom flask reactor, methyl 5-bromo-2-iodobenzoate (25.0 g, 73 mmol), 4-dibenzofuran boronic acid (18.7 g, 88 mmol), tetrakis (triphenylphosphine)palladium (1.7 g, 0.15 mmol), and potassium carbonate (20.2 g, 146.7 mmol) stirred together with toluene (125 mL), tetrahydrofuran (125 mL), and water (50 mL) for 10 hrs at 80° C. After completion of the reaction, the reaction mixture was cooled to room temperature and extracted with ethyl acetate. The organic layer thus formed was separated, concentrated in a vacuum, and purified by column chromatography to afford <Intermediate 1-a>. (75.0 g, 60.1%).

Synthesis Example 1-(2): Synthesis of [Intermediate 1-b]

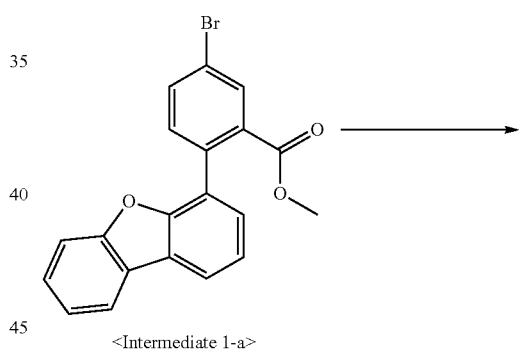

<Intermediate 1-a>

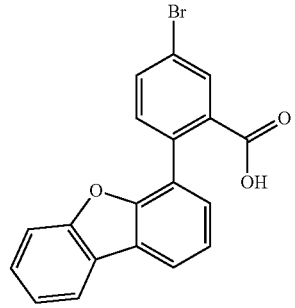

<Intermediate 1-b>

In a 500-mL round-bottom flask reactor, <Intermediate 1-a> (17.0 g, 45 mmol), sodium hydroxide (2.14 g, 54 mmol) and ethanol (170 ml) were stirred together for 48 hrs under reflux. After the completion of the reaction was confirmed by thin layer chromatography, the reaction mixture was cooled to room temperature. The chilled solution was acidified with drops of 2-N HCl, followed by stirring for 30 min. The solid thus formed was filtered, and recrystallized in dichloromethane and n-hexane to afford <Intermediate 1-b>. (14.5 g, 88.6%)

Synthesis Example 1-(3): Synthesis of [Intermediate 1-c]

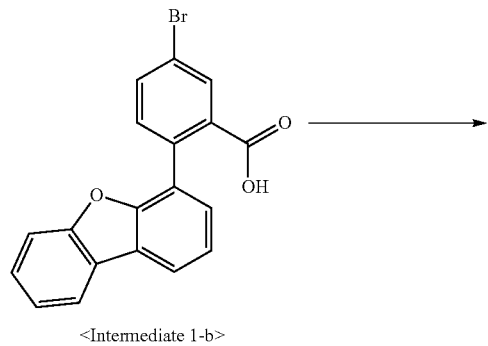

<Intermediate 1-b>

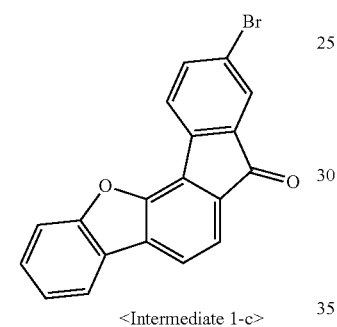

<Intermediate 1-c>

In a 250-mL round-bottom flask reactor, <Intermediate 1-b> (14.5 g, 39 mmol) and methanesulfonic acid (145 ml) were stirred together for 3 hrs at 80° C. After the completion of the reaction was confirmed by thin layer chromatography, the reaction mixture was cooled to room temperature and dropwise added to ice water (150 ml). After stirring for 30 min, the solid thus formed was filtered and washed with water and methanol to afford <Intermediate 1-c>. (11.50 g, 83.4%)

Synthesis Example 1-(4): Synthesis of [Intermediate 1-d]

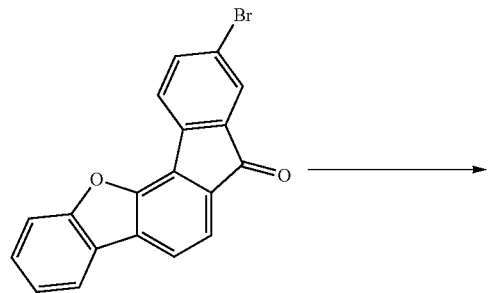

<Intermediate 1-c>

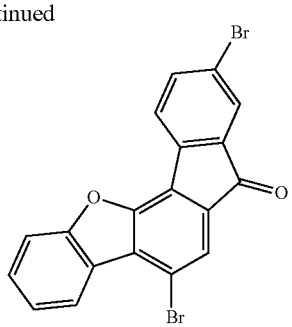

<Intermediate 1-d>

In a 1-L round-bottom flask reactor, <Intermediate 1-c> (11.5 g, 33 mmol) and dichloromethane (300 ml) were stirred together at room temperature. A dilution of bromine (3.4 ml, 66 mmol) in dichloromethane (50 ml) was dropwise added, followed by stirring at room temperature for 8 hrs. After completion of the reaction, the reaction mixture was stirred together with acetone (100 ml). The solid thus formed was filtered, and washed with acetone. Recrystallization in monochlorobenzene afforded <Intermediate 1-d>. (11.0 g, 78%)

Synthesis Example 1-(5): Synthesis of [Intermediate 1-e]

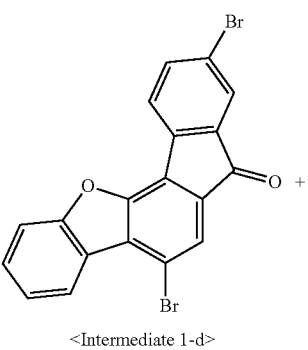

<Intermediate 1-d>

<Intermediate 1-e>

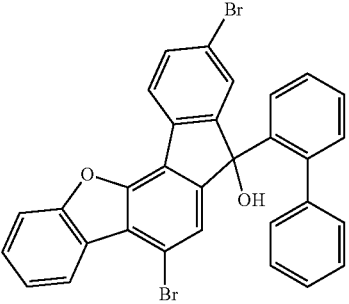

In a 250-ml round-bottom flask reactor, 2-bromobiphenyl (8.4 g, 0.036 mol) and tetrahydrofuran (110 ml) were chilled at −78° C. under a nitrogen atmosphere. At the same temperature, n-butyl lithium (19.3 nil, 0.031 mol) was dropwise added to the reaction solution which was then stirred for 2 hrs. Thereafter, <Intermediate 1-d> (11.0 g, 0.026 mol) was added little by little to the reaction solution, and stirred at room temperature. When the reaction mixture started to change color, the reaction was monitored via thin layer chromatography. After the reaction was stopped with H$_2$O (50 ml), extraction was conducted with ethylacetate and water. The organic layer was separated, concentrated in a vacuum, and recrystallized in acetonitrile to afford <Intermediate 1-e> as a solid. (12.2 g, 81.5%)

Synthesis Example 1-(6): Synthesis of [Intermediate 1-f]

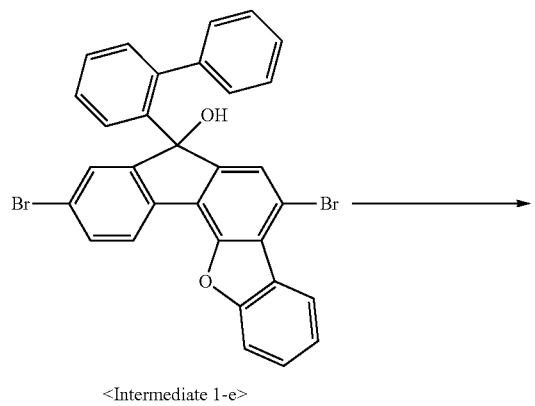

<Intermediate 1-e>

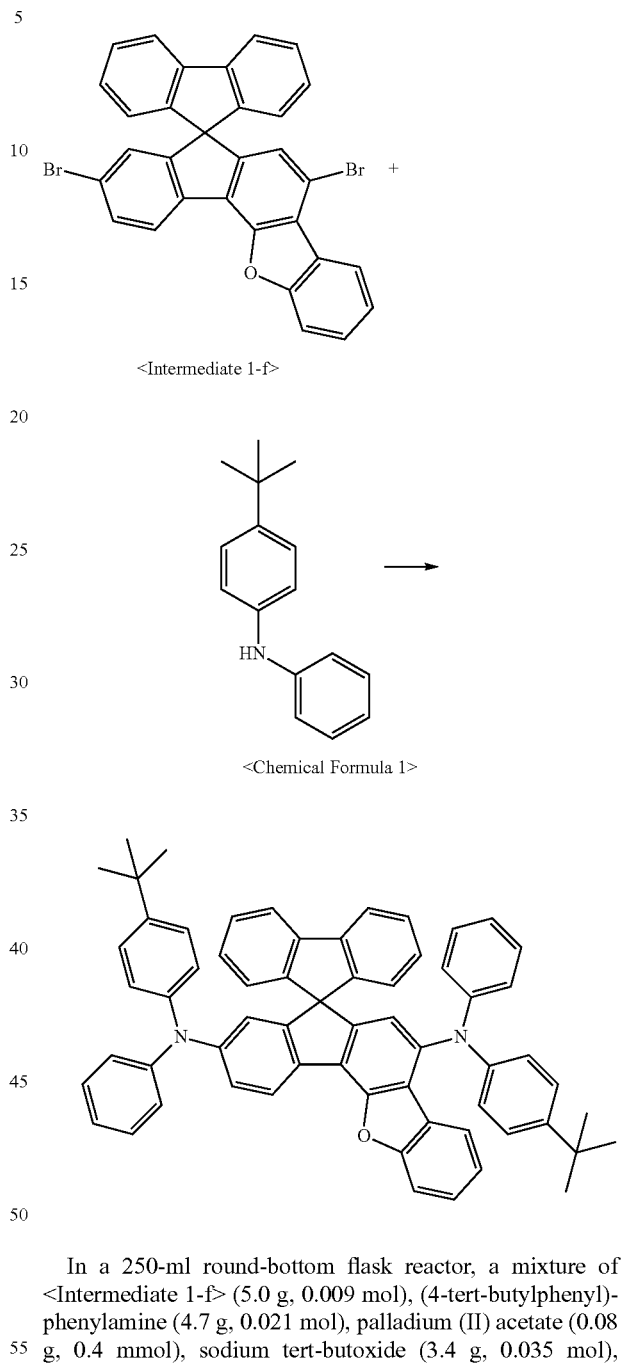

<Intermediate 1-f>

<Intermediate 1-f>

<Chemical Formula 1>

In a 250-ml round-bottom flask reactor, a mixture of <Intermediate 1-e> (12.0 g, 0.021 mol), acetic acid (120 ml), and sulfuric acid (2 ml) was stirred for 5 hrs under reflux. When a precipitate was formed, the completion of the reaction was monitored using thin layer chromatography. The reaction mixture was then cooled to room temperature and filtered. The filtrate was washed with H$_2$O and methanol and dissolved in monochlorobenzene. Following silica gel chromatography, the fraction was concentrated and cooled to room temperature to give <Intermediate 1-f>. (10.7 g, 90%>

Synthesis Example 1-(7): Synthesis of Compound of Chemical Formula 1

In a 250-ml round-bottom flask reactor, a mixture of <Intermediate 1-f> (5.0 g, 0.009 mol), (4-tert-butylphenyl)-phenylamine (4.7 g, 0.021 mol), palladium (II) acetate (0.08 g, 0.4 mmol), sodium tert-butoxide (3.4 g, 0.035 mol), tri-tert-butyl phosphine (0.07 g, 0.4 mmol), and toluene (60 ml) were stirred together for 2 hrs under reflux. After completion of the reaction, the reaction mixture was cooled to room temperature and then extracted with dichloromethane and water. The organic layer thus formed was separated, dried over magnesium sulfate, and concentrated in a vacuum. The concentrate was purified by column chromatography and recrystallized in dichloromethane and acetone to yield the compound of Chemical Formula 1 as a solid (2.9 g, 38%).

MS (MALDI-TOF): m/z 852.41 [M+]

Synthesis Example: Synthesis of Compound of Chemical Formula 231

Synthesis Example 2-(1): Synthesis of Intermediate 2-a

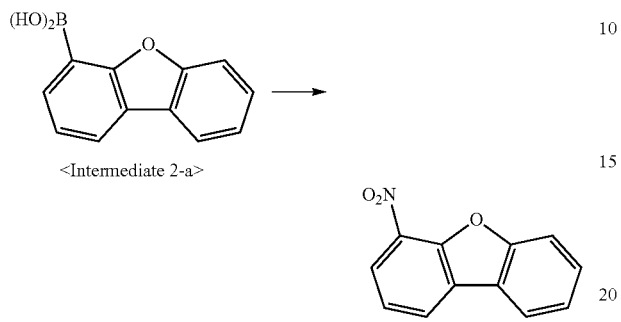

<Intermediate 2-a>

In a 1-L round-bottom flask reactor, dibenzofuran-4-bronic acid (85.0 g, 0.401 mol), bismuth (III) nitrate pentahydrate (99.2 g, 0.200 mol), and toluene (400 ml) were reacted at 70° C. for 3 hrs under a nitrogen atmosphere while stirring. After completion of the reaction, the reaction mixture was cooled to room temperature and washed with toluene. Filtration afforded <Intermediate 2-a> as a solid (61.5 g, 72%).

Synthesis Example 2-(2): Synthesis of Intermediate 2-b

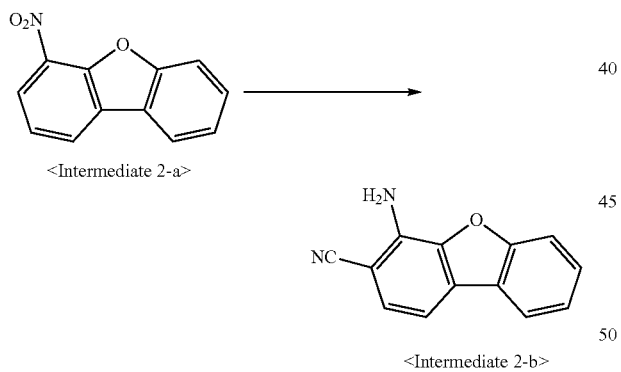

<Intermediate 2-a>

<Intermediate 2-b>

In a 2-L round-bottom flask reactor, ethylcyanoacetate (202.9 g, 1.794 mol), and dimethylformamide (500 ml) were added with potassium hydroxide (67.10 g, 1.196 mol), potassium cyanide (38.95 g, 0.598 mol), and dimethylformamide (200 ml), followed by stirring at room temperature. To this reaction solution, <Intermediate 2-a> (127.5 g, 0.737 mol) was slowly added while stirring at 50° C. for 72 hrs. After completion of the reaction, an aqueous sodium hydroxide solution (25%, 200 ml) was added, and stirred for 3 hrs under reflux. Subsequently, the reaction mixture was cooled to room temperature, followed by extraction with ether acetate and water. The organic layer was separated and concentrated. Purification by column chromatography afforded <Intermediate 2-b> (20.0 g, 16%).

Synthesis Example 2-(3): Synthesis of Intermediate 2-c

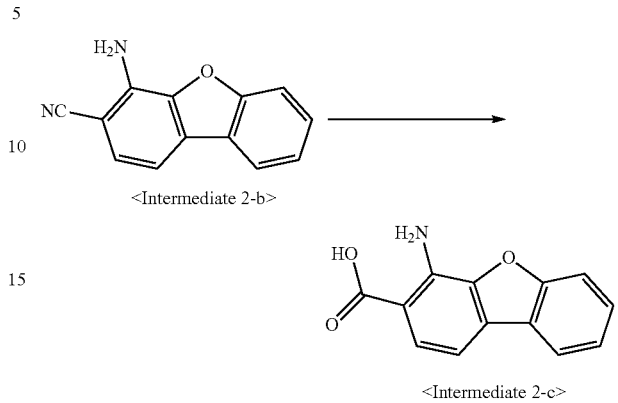

<Intermediate 2-b>

<Intermediate 2-c>

In a 2-L round-bottom flask reactor, <Intermediate 2-b> (20.0 g, 0.096 mol), ethanol (600 ml), and an aqueous solution (170 ml) of potassium hydroxide solution (142.26 g, 2.53 mol) were stirred for 12 hrs under reflux. After completion of the reaction, the reaction mixture was cooled to room temperature, and acidified with 6 N HCl (400 ml). Then, the reaction mixture was stirred for 20 min, and filtered. The filtrate was washed with ethanol to afford <Intermediate 2-c> as a solid (17.0 g, 88.5%).

Synthesis Example 2-(4): Synthesis of Intermediate 2-d

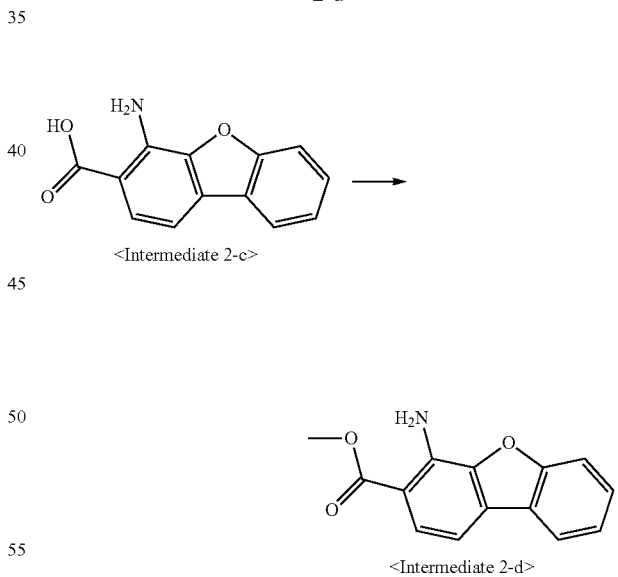

<Intermediate 2-c>

<Intermediate 2-d>

In a 2-L round-bottom flask reactor, <Intermediate 2-c> (17.0 g, 0.075 mol) and sulfuric acid (15 ml) were stirring together for 72 hrs under reflux. After completion of the reaction, the reaction mixture was cooled to room temperature and extracted with ethylacetate and water. The organic layer was separated, and washed with an aqueous sodium hydrogen carbonate solution. An excess of methanol was added during vacuum concentration, followed by filtration to afford <Intermediate 2-4:1> as a solid (14.0 g, 77.6%).

Synthesis Example 2-(5): Synthesis of Intermediate 2-e

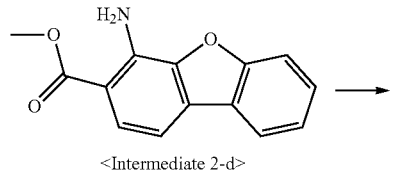

<Intermediate 2-d>

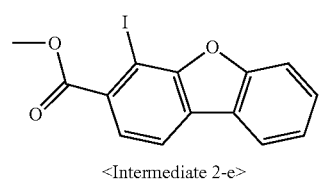

<Intermediate 2-e>

In a 500-mL round-bottom flask reaction, <Intermediate 2-4:1> (14.0 g, 0.058 mol), HCl (20 ml), and water (100 ml) were stirred together for 1 hr at 0° C. At the same temperature, an aqueous solution (50 ml) of sodium nitrite (7.4 g, 0.116 mol) was dropwise added to the reaction mixture and then stirred for 1 hr. An aqueous solution (100 ml) of potassium iodide (30.0 g, 0.180 mol) was dropwise added with care not to increase the temperature of the reaction solution above 5° C. Stirring was continued for 5 hrs at room temperature, and after completion of the reaction, the reaction mixture was washed with an aqueous sodium thiosulfate solution, and extracted with ethylacetate and water. The organic layer was separated and concentrated in a vacuum. Purification through column chromatography gave <Intermediate 2-e> (9.1 g, 48%).

Synthesis Example 2-(6): Synthesis of Intermediate 2-f

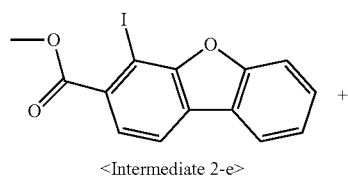

<Intermediate 2-e>

+

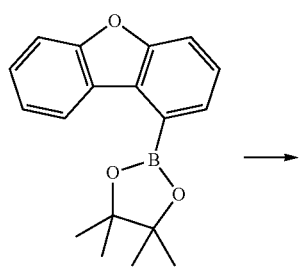

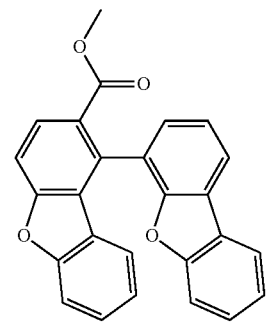

<Intermediate 2-f>

In a 250-mL round-bottom flask reactor, <Intermediate 2-e> (9.3 g, 25 mmol), 4-dibenzofuranborate (8.3 g, 28 mmol), tetrakis(triphenylphosphine)palladium (0.6 g, 0.05 mmol), and potassium carbonate (6.7 g, 50 mmol) were placed, and then toluene (50 mL), tetrahydrofuran (50 mL), and water (20 mL) were added. The temperature of the reactor was elevated to 80° C. before stirring for 10 hrs. After completion of the reaction, the temperature was cooled to room temperature, and extraction was conducted with ethylacetate. The organic layer thus formed was concentrated in a vacuum and purified by column chromatography to afford <Intermediate 2-f> (5.3 g, 52.3%).

Synthesis Example 2-(7): Synthesis of Intermediate 2-g

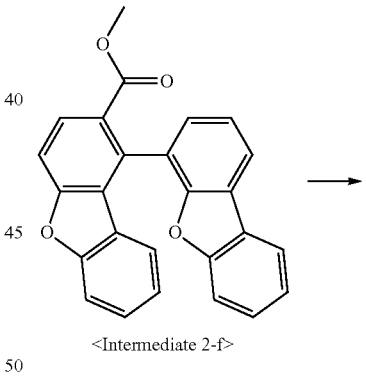

<Intermediate 2-f>

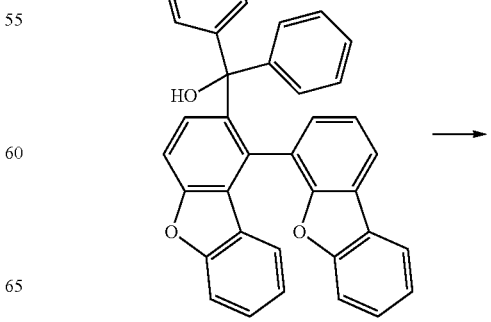

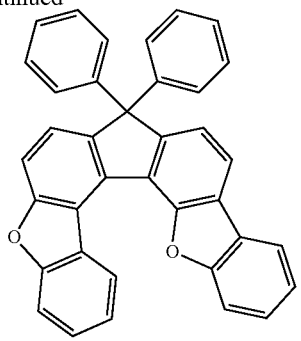

<Intermediate 2-g>

In a 500-ml round-bottom flask reactor, bromobenzene (25.5 g, 0.163 mol) and tetrahydrofuran (170 ml) were cooled to −78° C. in a nitrogen atmosphere. N-butyl lithium (95.6 ml, 0.153 mol) was dropwise added to the chilled solution, and stirred for 1 hr at the same temperature. Then, <Intermediate 44> (20.0 g, 0.051 mol) was added at room temperature while stirring. After completion of the reaction, the reaction mixture was stirred together with water (50 ml), and extraction with ethyl acetate and water was conducted. The organic layer was concentrated and the concentrate was mixed with acetic acid (200 ml) and HCl (1 ml) by stirring at 80° C. After completion of the reaction, the reaction mixture was cooled to room temperature, and the precipitate thus formed was filtered, and washed with methanol to afford <Intermediate 2-g> (20.0 g, 78%).

Synthesis Example 2-(8): Synthesis of Intermediate 2-h

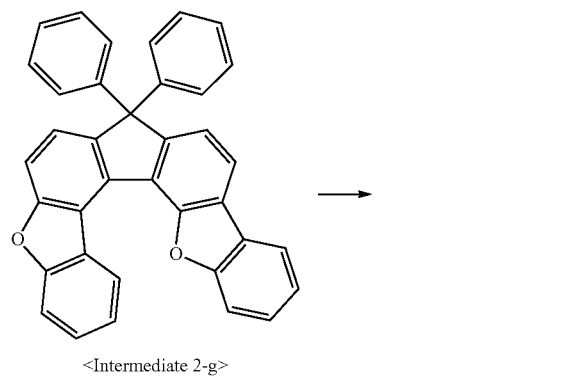

<Intermediate 2-g>

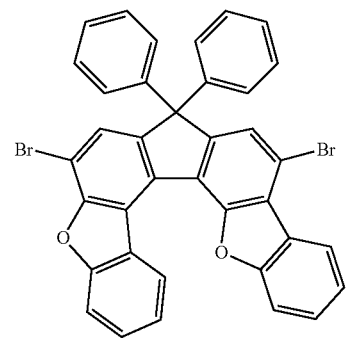

<Intermediate 2-h>

In a 100-mL round-bottom flask reactor, <Intermediate 2-g> (20 g, 58 mmol) and dichloromethane (40 ml) were stirred together at room temperature. A dilution of bromine (5.8 ml, 116 mmol) in dichloromethane (10 ml) was dropwise added, followed by stirring at room temperature for 8 hrs. After completion of the reaction, the reaction mixture was stirred together with acetone (20 ml). The solid thus formed was filtered, and washed with acetone. Recrystallization in monochlorobenzene afforded <Intermediate 2-h> (15.8 g, 55%)

Synthesis Example 2-(9): Synthesis of Compound of Chemical 231

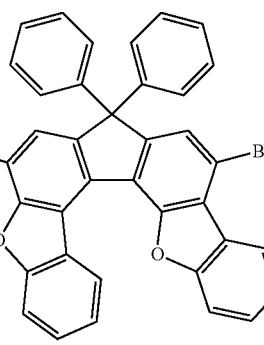

<Intermediate 2-h>

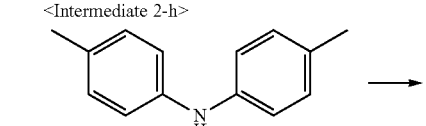

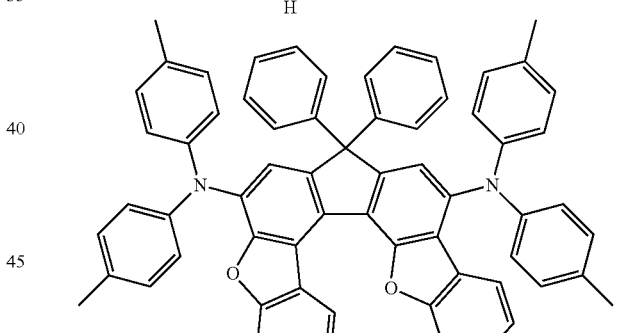

<Chemical Formula 231>

In a 100-ml round-bottom flask reactor, a mixture of <Intermediate 2-h> (4.0 g, 0.006 mol), di-p-tollylamine (3.2 g, 0.016 mol), palladium (II) acetate (0.08 g, 0.4 mmol), sodium tert-butoxide (3.2 g, 0.032 mol), tri-tert-butyl phosphine (0.08 g, 0.4 mmol), and toluene (50 ml) were stirred together for 2 hrs under reflux. After completion of the reaction, the reaction mixture was cooled to room temperature and then extracted with dichloromethane and water. The organic layer thus formed was separated, dried over magnesium sulfate, and concentrated in a vacuum. The concentrate was purified by column chromatography and recrystallized in dichloromethane and acetone to yield <Chemical Formula 231> as a solid (2.1 g, 41%).

MS (MALDI-TOF): m/z 888.37 [M$^+$]

Synthesis Example 3: Synthesis of Compound 21

Synthesis Example 3-(1): Synthesis of Intermediate 3-a

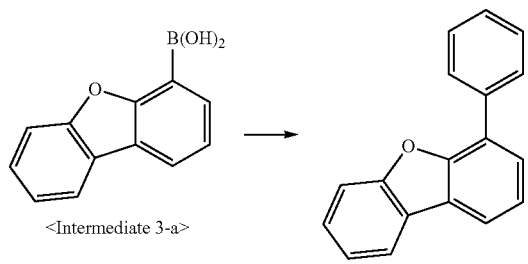 [SMILES: OB(O)c1cccc2c1oc1ccccc12 ; c1ccc(-c2cccc3c2oc2ccccc23)cc1]

In a 2-L round-bottom flask reactor, bromobenzene (100.0 g, 637 mmol), 4-dibenzofuran boronic acid (18.7 g, 88 mmol), tetrakis(triphenylphosphine)palladium (1.7 g, 0.15 mmol), and potassium carbonate (437.9 g, 700 mmol) were stirred together with toluene (500 mL), tetrahydrofuran (500 mL) and water (200 mL) at 80° C. for 10 hrs. After completion of the reaction, the reaction mixture was cooled to room temperature and extracted with ethyl acetate. The organic layer thus formed was isolated, and concentrated in a vacuum. Purification via column chromatography afforded <Intermediate 3-a> (78.0 g, 50%).

Synthesis Example 3-(2): Synthesis of Intermediate 3-b

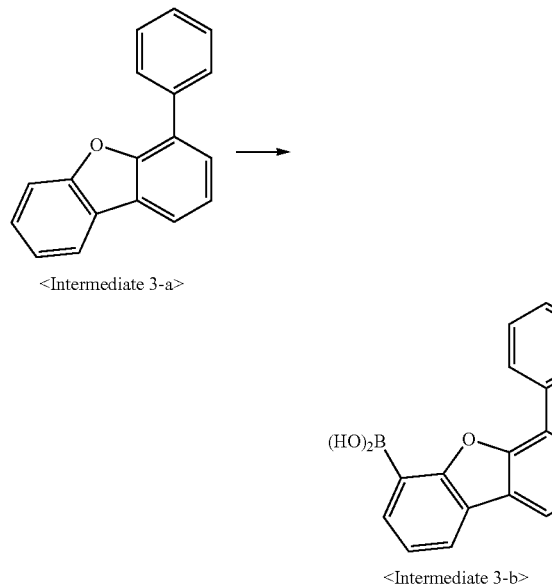

In a 2-L round-bottom flask reactor, <Intermediate 3-a> (78.0 g, 318 mmol) and tetrahydrofuran (800 ml) were cooled together to −78° C. in a nitrogen atmosphere. N-butyl lithium (239 ml, 382 mmol) was dropwise added to the cold solution, and stirred for 2 hr at the same temperature. Then, trimethyl borate (46.3 g, 446 mmol) was added little by little at room temperature while stirring. When the reaction mixture started to change color, the reaction was monitored via thin-layer chromatography. After the reaction was stopped with H$_2$O (400 ml), extraction was conducted with ethyl acetate and water. The organic layer was separated, concentrated in a vacuum, and recrystallized in acetonitrile to afford <Intermediate 3-b> as a solid (65.1 g, 71%).

Synthesis Example 3-(3): Synthesis of Intermediate 3-c

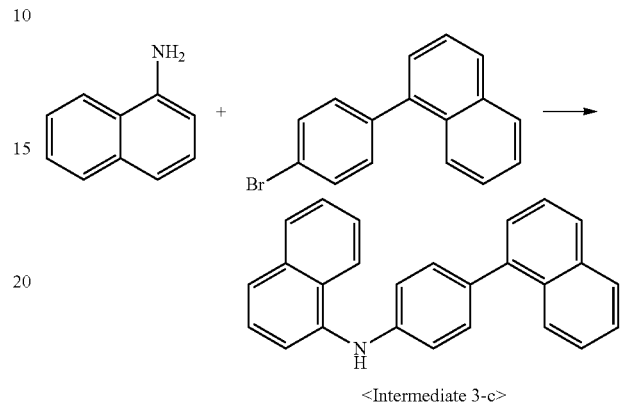

In a 2-L round-bottom flask reactor, 1-aminonaphthalene (30.0 g, 191 mmol), 1-(4-bromo-phenyl)-naphthalene (113.4 g, 181 mmol), palladium (II) acetate (0.9 g, 4 mmol), sodium tert-butoxide (85.0 g, 382 mmol), tert-butyl phosphine (0.8 g, 4 mmol), and toluene (1000 ml) were stirred together for 2 hrs under reflux. After completion of the reaction, the reaction mixture was cooled to room temperature. The reaction mixture was extracted with dichloromethane and water, and the organic layer was separated and concentrated in a vacuum. Following column chromatography, recrystallization in dichloromethane and acetone afforded <Intermediate 3-c> as a solid (35.0 g, 53%).

Synthesis Example 3-(4): Synthesis of Intermediate 3-d

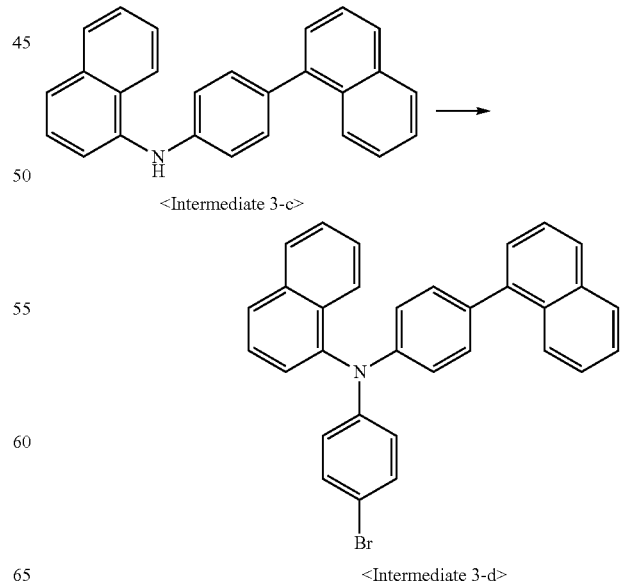

In a 1-L round-bottom flask reactor, <Intermediate 3-c> (35.0 g, 101 mmol), 4-bromo-iodobenzene (69.7 g, 112 mmol), palladium(II) acetate (0.5 g, 2 mmol), sodium tert-butoxide (45.1 g, 203 mmol), tri-tert-butyl phosphine (0.4 g, 2 mmol), and toluene (500 ml) were stirred together for 2 hrs under reflux. After completion of the reaction, the reaction mixture was cooled to room temperature. The reaction mixture was extracted with dichloromethane and water, and the organic layer was separated and concentrated in a vacuum. Following column chromatography, recrystallization in dichloromethane and acetone afforded <Intermediate 3-4:1> as a solid (225.9 g, 51%).

Synthesis Example 3-(5): Synthesis of Compound 21

In a 500-ml round-bottom flask reactor, <Intermediate 3-b> (13.7 g, 22 mmol), <Intermediate 3-d> (10.0 g, 20 mmol), tetrakis(triphenylphosphine)palladium (0.5 g, 0.4 mmol), and potassium carbonate (5.5 g, 40 mmol) were placed, followed by toluene (100 mL), tetrahydrofuran (100 mL) and water (40 mL). The reaction mixture was heated to 80° C. and stirred for 10 hrs. After completion of the reaction, the reaction mixture was cooled to room temperature. Recrystallization in dichloromethane and acetone afforded <Compound 21> (6.4 g, 48%).

MS (MALDI-TOF): m/z 663.26 [M$^+$]

Synthesis Example 4: Synthesis of Compound 31

Synthesis Example 4-(1): Synthesis of Intermediate 4-a

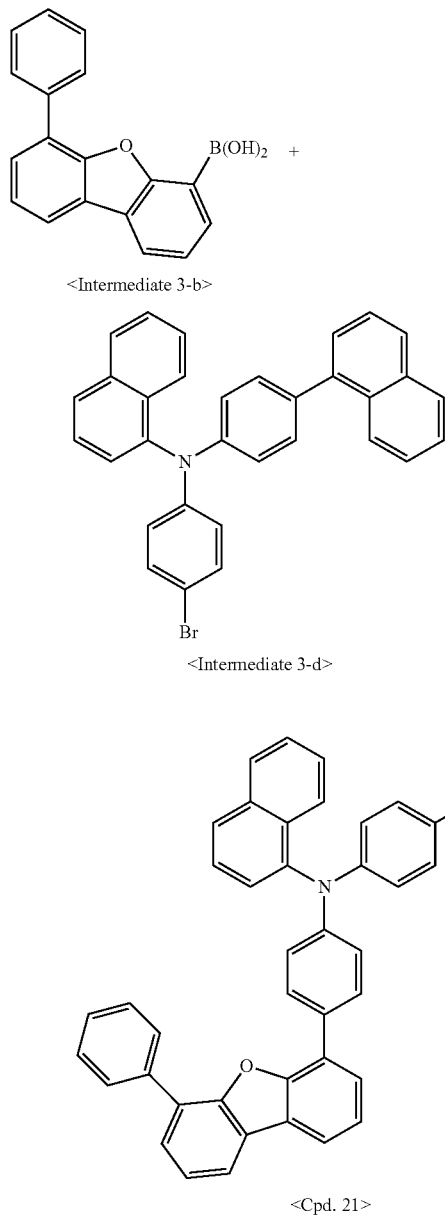

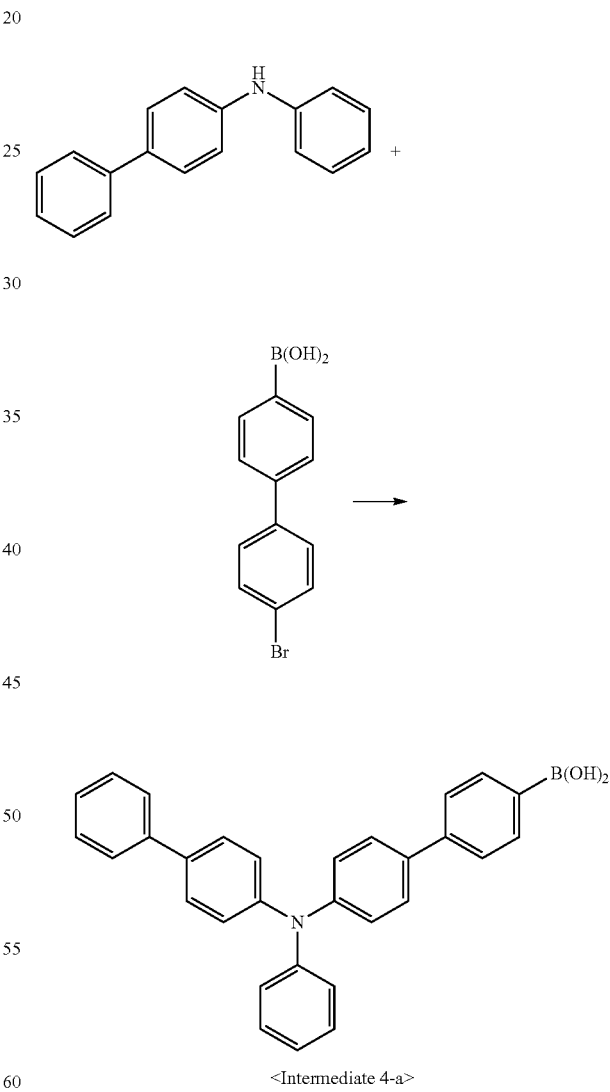

<Intermediate 4-a> was synthesized in the same manner as in Synthesis Example 3-(4), with the exception that 에서 대신 4-(phenylamino)biphenyl and 4-bromobiphenyl-4'-boronic acid were used instead of <Intermediate 3-c> and 4-bromo-iodobenzene, respectively.

Synthesis Example 4-(2): Synthesis of Compound 31

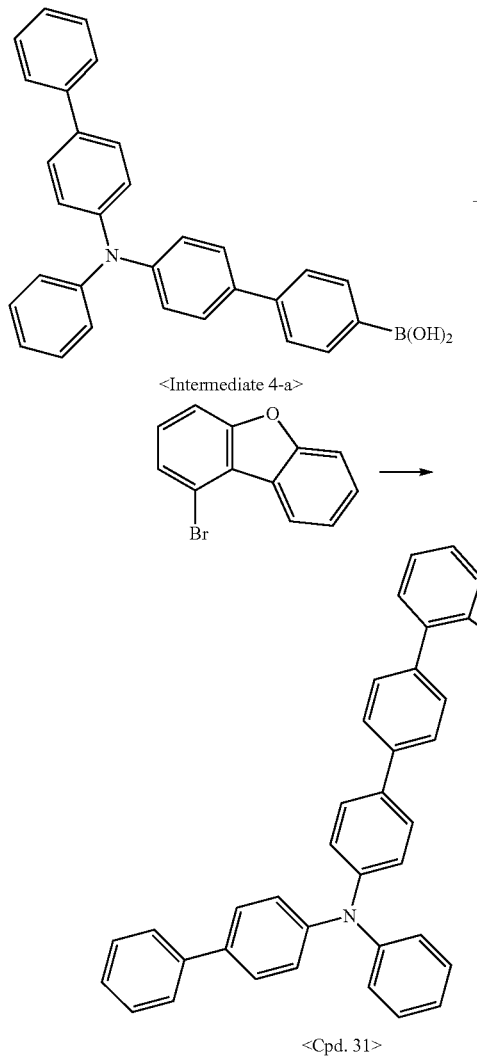

<Compound 31> was synthesized in the same manner as in Synthesis Example 3-(1), with the exception that 1-bromodibenzofuran and <Intermediate 4-a> were used instead of bromobenzene and 4-dibenzofuran boronic acid, respectively.

MS (MALDI-TOF): m/z 563.22 [M$^+$]

Examples 1 to 4: Fabrication of Organic Light-Emitting Diodes

An ITO glass substrate was patterned to have a translucent area of 2 mm×2 mm and cleansed. The ITO glass was mounted in a vacuum chamber that was then set to have a base pressure of 1×10$^{-7}$ torr. On the ITO glass substrate, films were formed of DNTPD (400 Å) and α-NPD (200 Å) in that order. Then, an electron-blocking layer (50 Å) was formed of the compounds listed in Table 1, below. In addition, a light-emitting layer (200Å) was formed of a mixture of BH and BDI (weight ratio 97:3). On the light-emitting layer, then, [Chemical Formula E-1] for an electron transport layer (300 Å), [Chemical Formula E-2] for an electron injection layer (5 Å), and Al (1000 Å) were deposited in the order to fabricate an organic light-emitting diode.

The organic light-emitting diode thus obtained was measured at 10 mA/cm$^2$ for luminescence properties.

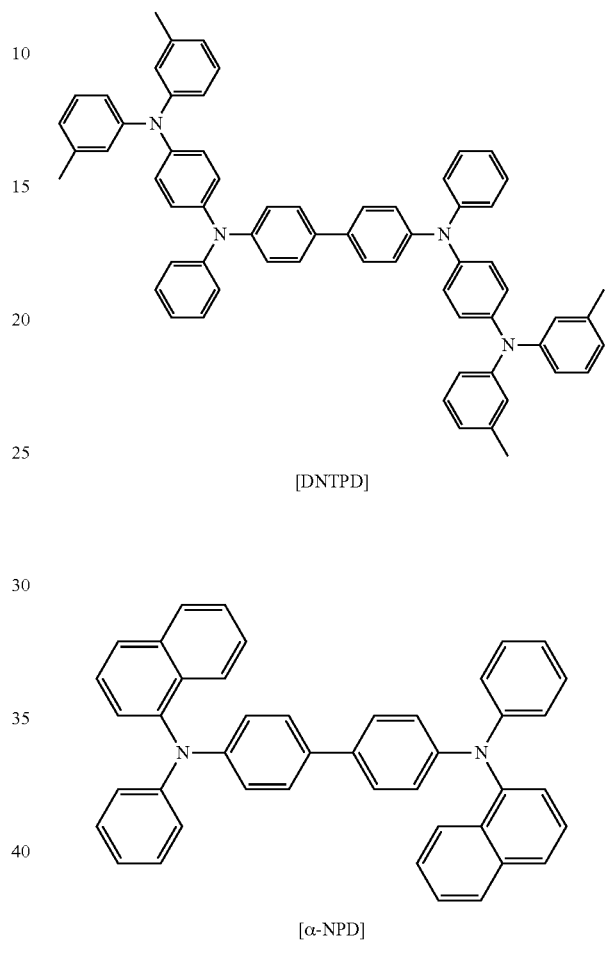

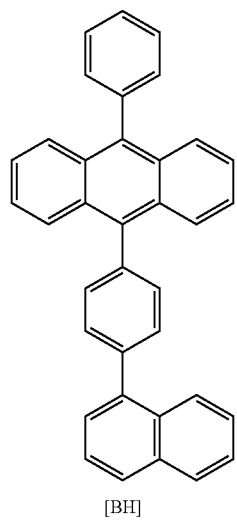

-continued

[Chemical Formula E-1]

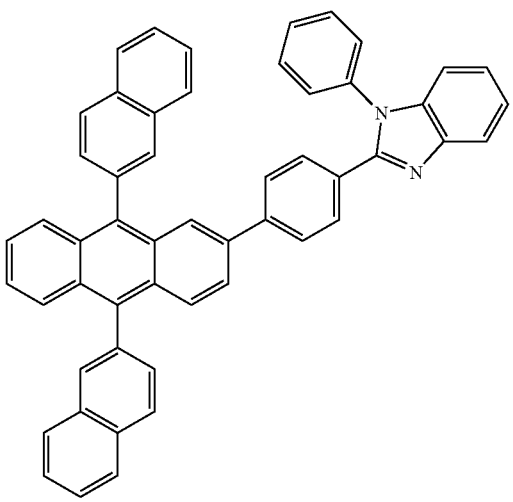

[Chemical Formula E-2]

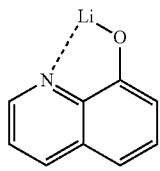

Comparative Examples 1 and 2

Organic light-emitting diodes were fabricated in the same manner as in Examples 1 to 4, with the exception that [EBL] was used for the electron-blocking layer. The organic light-emitting diode thus obtained was measured at 10 mA/cm² for luminescence properties.

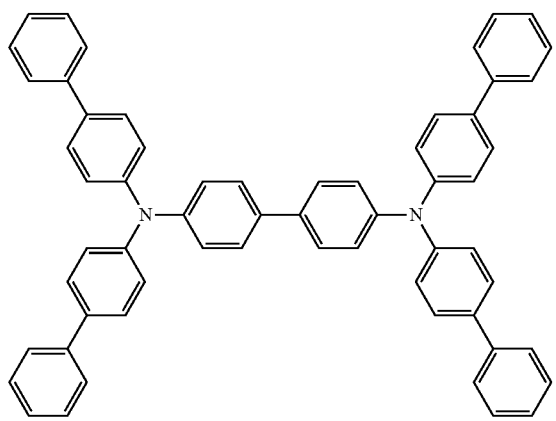

[EBL]

Comparative Example 3

An ITO glass substrate was patterned to have a luminescent area of 2 mm×2 mm and cleansed. The ITO glass was mounted in a vacuum chamber that was then set to have a base pressure of 1×10⁻⁷ torr. On the ITO glass substrate, films were formed of DNTPD (400 Å) and α-NPD (200 Å) in that order. A light-emitting layer (200Å) was formed of a mixture of BH and BDI (weight ratio 97:3). Then, [Chemical Formula E-2] for an electron transport layer (300 Å), [Chemical Formula E-1] for an electron injection layer (5 Å), and Al (1000 Å) were deposited in that order to fabricate an organic light-emitting diode.

TABLE 1

| Ex. # | Dopant | Electron-Blocking layer | Cd/A | CIEx | CIEy |
|---|---|---|---|---|---|
| 1 | Chemical Formula 1 | Cpd. 21 | 8.7 | 0.139 | 0.103 |
| 2 | Chemical Formula 1 | Cpd. 31 | 8.5 | 0.139 | 0.103 |
| 3 | Chemical Formula 231 | Cpd. 21 | 8.5 | 0.139 | 0.101 |
| 4 | Chemical Formula 231 | Cpd. 31 | 8.6 | 0.139 | 0.102 |
| C. 1 | Chemical Formula 1 | EBL | 8.0 | 0.138 | 0.103 |
| C. 2 | Chemical Formula 231 | EBL | 7.9 | 0.138 | 0.103 |
| C. 3 | Chemical Formula 1 | — | 6.8 | 0.138 | 0.103 |

As is understood from the data of Table 1, the organic light-emitting diodes of the present disclosure exhibited higher luminous efficiency (1 m/V) than the organic light-emitting diodes using the compounds of Comparative Examples 1 to 3, thereby demonstrating their high applicability to organic electroluminescence devices.

Therefore, the organic light-emitting diode according to the present disclosure can operate at lower voltages with higher efficiency than those of the conventional art.

Although the preferred embodiments of the present disclosure have been disclosed for illustrative purposes, those skilled in the art will appreciate that various modifications, additions and substitutions are possible, without departing from the scope and spirit of the disclosure as disclosed in the accompanying claims.

What is claimed is:

1. An organic light-emitting diode, comprising:
   a first electrode;
   a second electrode facing the first electrode; and
   an electron-blocking layer and a light-emitting layer sequentially interposed between the first electrode and the second electrode,
   wherein the light-emitting layer comprises at least one of the amine compounds represented by the following Chemical Formula B, and the electron-blocking layer comprises the compound represented by the following Chemical Formula C:

[Chemical Formula B]

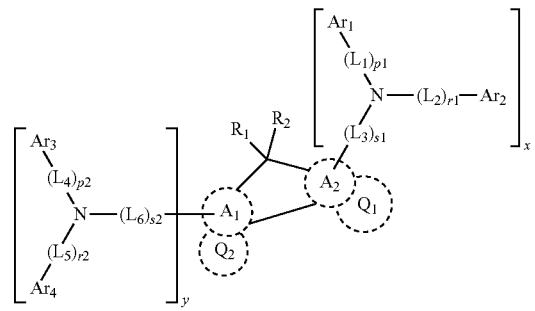

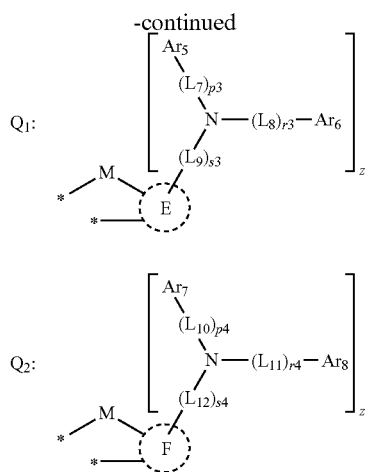

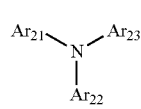

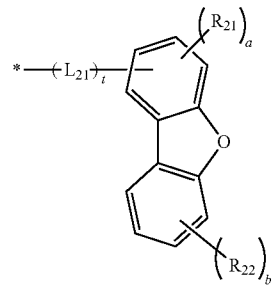

wherein, $A_1$, $A_2$, E, and F are the same or different, and are each independently a substituted or unsubstituted aromatic hydrocarbon ring of 6 to 50 carbon atoms, or a substituted or unsubstituted heteroaromatic ring of 2 to 40 carbon atoms wherein two adjacent carbon atoms of the aromatic ring $A_1$ and two adjacent carbon atoms of the aromatic ring $A_2$ form a 5-membered fused ring together with a carbon atom to which substituents $R_1$ and $R_2$ are bonded;

linkers $L_1$ to $L_{12}$ are the same or different, and are each independently a direct bond or a substituted or unsubstituted arylene of 6 to 60 carbon atoms;

M is any one selected from among N—$R_3$, $CR_4R_5$, O, and S;

$R_1$ to $R_5$, and $Ar_1$ to $Ar_8$ are the same or different, and are each independently any one selected from among hydrogen, deuterium, a substituted or unsubstituted alkyl of 1 to 30 carbon atoms, a substituted or unsubstituted aryl of 6 to 50 carbon atoms, a substituted or unsubstituted cycloalkyl of 3 to 30 carbon atoms, a substituted or unsubstituted heteroaryl of 2 to 50 carbon atoms, a substituted or unsubstituted alkylsilyl of 1 to 30 carbon atoms, a substituted or unsubstituted arylsilyl of 6 to 30 carbon atoms, a substituted or unsubstituted alkyl germanium of 1 to 30 carbon atoms, a substituted or unsubstituted aryl germanium of 6 to 30 carbon atoms, a cyano, a nitro, and a halogen, with a proviso that $R_1$ and $R_2$ together may form a mono- or polycyclic aliphatic or aromatic ring, which may be a heterocyclic ring containing a heteroatom selected from among N, O, P, Si, and S as a ring member;

p1 to p4, r1 to r4, and s1 to s4 are each independently an integer of 1 to 3, with a proviso that when any of them is 2 or greater, the corresponding linkers are the same or different, x is 1, and y and z are the same or different and are each independently an integer of 0 or 1; and in the alternative for $Ar_1$ to $Ar_8$, $Ar_1$ forms a ring with $Ar_2$, $Ar_3$ forms a ring with $Ar_4$, $Ar_5$ forms a ring with $Ar_6$, and $Ar_7$ forms a ring with $Ar_8$, two adjacent carbon atoms of the $A_2$ ring moiety of Chemical Formula B occupy respective positions * of structural Formula $Q_1$ to form a fused ring and, two adjacent carbon atoms of the $A_1$ ring moiety of Chemical Formula B occupy respective positions * of structural Formula $Q_2$ to form a fused ring, wherein, $Ar_{21}$ to $Ar_{23}$ are the same or different and are each independently selected from among a substituted or unsubstituted aryl of 6 to 50 carbon atoms, a substituted or unsubstituted heteroaryl of 3 to 50 carbon atoms containing O, N or S as a heteroatom, and a compound represented by the following Structural Formula A, with a proviso that at least one of $Ar_{21}$ to $Ar_{23}$ is the compound of Structural Formula A:

[Structural Formula A]

wherein, $L_{21}$ is selected from among a single bond, a substituted or unsubstituted aryl of 6 to 50 carbon atoms, and a substituted or unsubstituted heteroaryl of 3 to 50 carbon atoms containing O, N or S as a heteroatom;

t is an integer of 1 to 3, with a proviso that when it is 2 or greater, the corresponding $L_{21}$'s is the same or different, $R_{21}$ and $R_{22}$ are the same or different, and are each independently selected from the group consisting of hydrogen, deuterium, a substituted or unsubstituted alkyl of 1 to 30 carbon atoms, a substituted or unsubstituted cycloalkyl of 3 to 30 carbon atoms, a substituted or unsubstituted aryl of 6 to 50 carbon atoms, a substituted or unsubstituted heteroaryl of 3 to 50 carbon atoms containing O, N or S as a heteroatom, a nitrile, a nitro, and a halogen;

a is an integer of 0 to 3, and b is an integer of 0 to 4, with a proviso that when a and b are each 2 or greater, the corresponding $R_{21}$'s and $R_{22}$'s are the same or different, wherein the term 'substituted' in the expression 'substituted or unsubstituted' for Chemical Formulas B and C means having at least one substituent selected from the group consisting of a deuterium, a cyano, a halogen, a nitro, an alkyl of 1 to 24 carbon atoms, a halogenated alkyl of 1 to 24 carbon atoms, an aryl of 6 to 24 carbon atoms, an arylalkyl of 7 to 24 carbon atoms, a heteroaryl of 2 to 24 carbon atoms or a heteroarylalkyl of 2 to 24 carbon atoms, an alkylsilyl of 1 to 24 carbon atoms, an arylsilyl of 6 to 24 carbon atoms.

2. The organic light-emitting diode of claim 1, wherein the light-emitting layer comprises a host and a dopant, the amine compound of Chemical Formula B serving as the dopant.

3. The organic light-emitting diode of claim 1, wherein $A_1$, $A_2$, E, and F of Chemical Formula B are identical or different, and are each independently a substituted or unsubstituted aromatic hydrocarbon ring of 6 to 50 carbon atoms.

4. The organic light-emitting diode of claim 3, wherein the substituted or unsubstituted aromatic hydrocarbon ring of 6 to 50 carbon atoms is selected from among compounds represented by [Structural Formula 10] to [Structural Formula 21]:

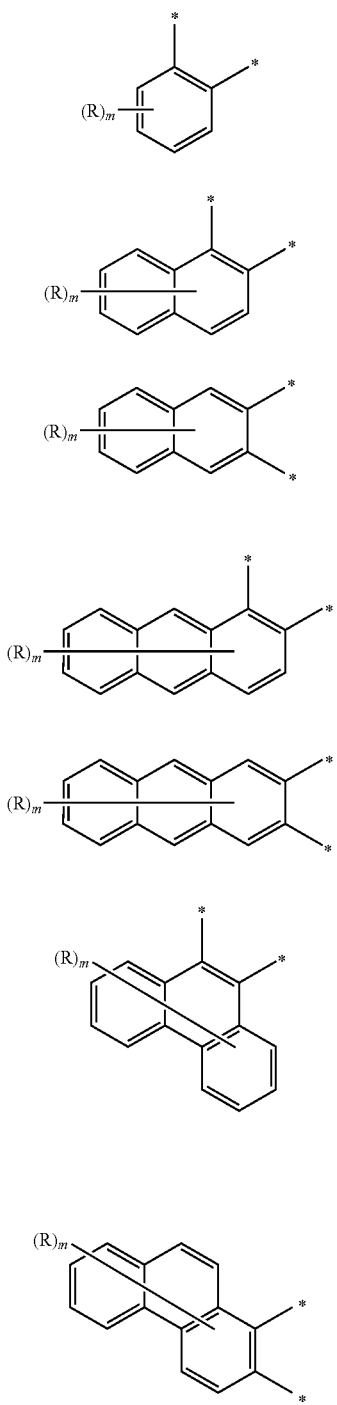

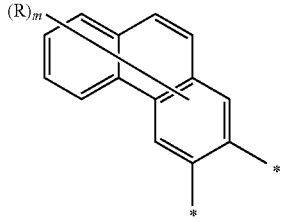

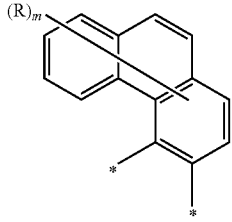

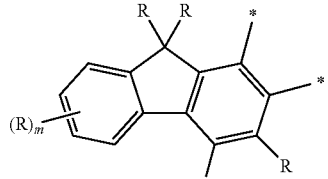

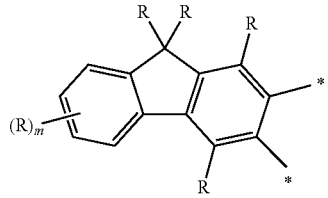

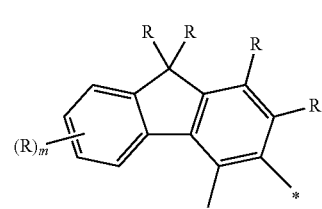

wherein,

"-*" for moiety $A_1$ or $A_2$ denotes a bonding site for forming a 5-membered ring containing the carbon atom connected to both $R_1$ and $R_2$, and "-*" for moiety E or F denotes a bonding site for forming a 5-membered ring containing M of the structural Formula $Q_1$ and $Q_2$ with moiety $A_1$ or $A_2$, when one of aromatic hydrocarbon rings of [Structural Formula 10] to [Structural Formula 21] for $A_1$ or $A_2$ is bonded to Structural Formula $Q_1$ or Structural Formula $Q_2$, two adjacent carbon atoms of the aromatic hydrocarbon ring occupy respective positions * of Structural Formula $Q_1$ or $Q_2$ to form a fused ring; and R in Structural Formulas 10 to 21 is selected from the group consisting of a hydrogen, a deuterium, a cyano, a halogen, a nitro, an alkyl of 1 to 24 carbon atoms, an aryl of 6 to 24 carbon atoms, an arylalkyl of 7 to 24 carbon atoms, a heteroaryl of 2 to 24 carbon atoms, a heteroarylalkyl of 2 to 24 carbon atoms, an alkylsilyl of 1 to 24 carbon atoms, and an arylsilyl of 6 to 24 carbon atoms, and m is an integer of 1 to 8, with the proviso that when m is 2 or greater or when 2 or more Rs are present, the corresponding Rs are the same or different.

5. The organic light-emitting diode of claim 1, wherein the linkers $L_1$ to $L_{12}$ of Chemical Formula B represent single bonds, or are each any one selected from the following [Structural Formula 22], [Structural Formula 23], [Structural Formula 25], [Structural Formula 27], [Structural Formula 28], and [Structural Formula 30], p1 to p4, r1 to r4, and s1 to s4 are each 1 or 2, and x is 1:

[Structural Formula 22]

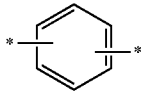

[Structural Formula 23]

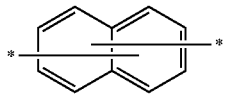

[Structural Formula 25]

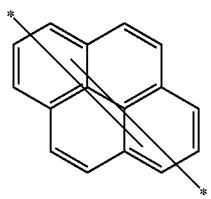

[Structural Formula 27]

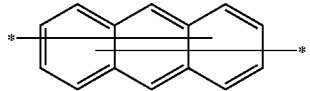

[Structural Formula 28]

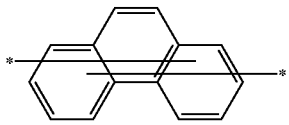

[Structural Formula 30]

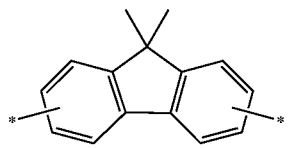

wherein hydrogen or deuterium is positioned on a carbon atom as a member in aromatic rings of the linkers.

6. The organic light-emitting diode of claim 1, wherein linker $L_{21}$ of Chemical Formula C is a single bond or a substituted or unsubstituted arylene of 6 to 20 carbon atoms.

7. The organic light-emitting diode of claim 1, wherein x and y are each 1 and z is 0 or 1 in Chemical Formula B.

8. The organic light-emitting diode of claim 1, wherein the substituents $Ar_{21}$ to $Ar_{23}$ on the compound represented by Chemical Formula C are the same or different and are each a substituted or unsubstituted aryl of 6 to 20 carbon atoms, one or two of $Ar_{21}$ to $Ar_{23}$ being the substituent represented by Structural Formula A wherein t is 1 or 2.

9. The organic light-emitting diode of claim 1, wherein the amine compound is any one selected from among compounds represented by the following [Chemical Formula 25] to [Chemical Formula 32], [Chemical Formula 85], [Chemical Formula 91], [Chemical Formula 92], [Chemical Formula 97], [Chemical Formula 98], [Chemical Formula 102], [Chemical Formula 117], [Chemical Formula 142] to [Chemical Formula 149], [Chemical Formula 160], [Chemical Formula 162], [Chemical Formula 164], [Chemical Formula 165], [Chemical Formula 197] to [Chemical Formula 201], [Chemical Formula 210], [Chemical Formula 222] to [Chemical Formula 224], [Chemical Formula 227] to [Chemical Formula 231], and [Chemical Formula 239], <Chemical Formula 25>

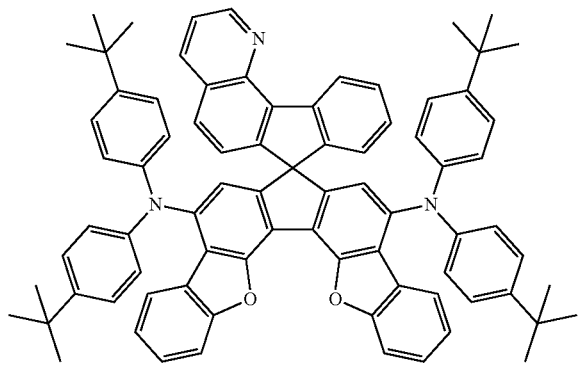

<Chemical Formula 26>
<Chemical Formula 27>
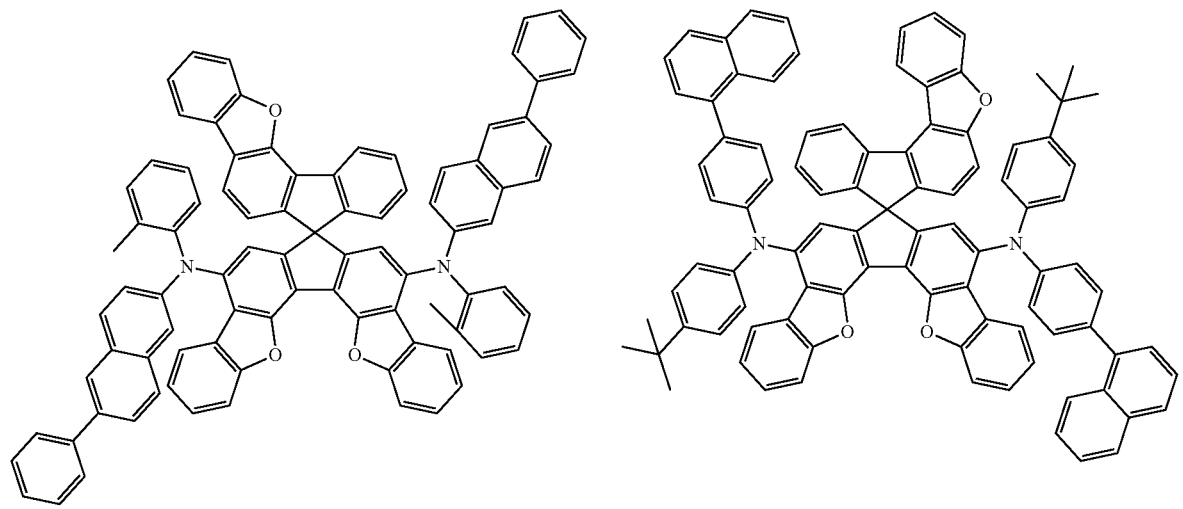
<Chemical Formula 28>
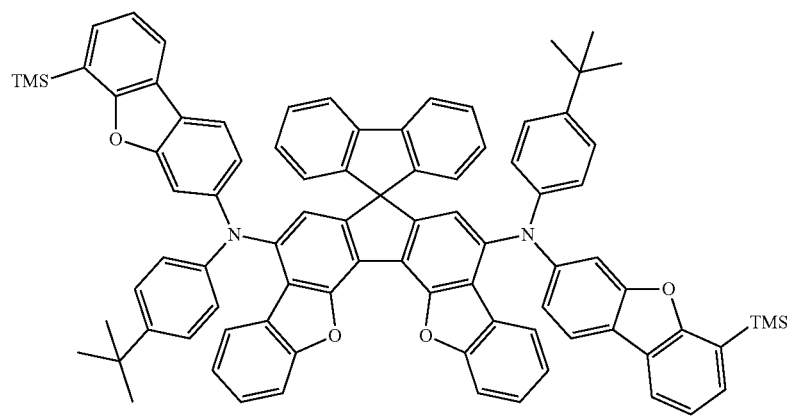
<Chemical Formula 29>
<Chemical Formula 30>
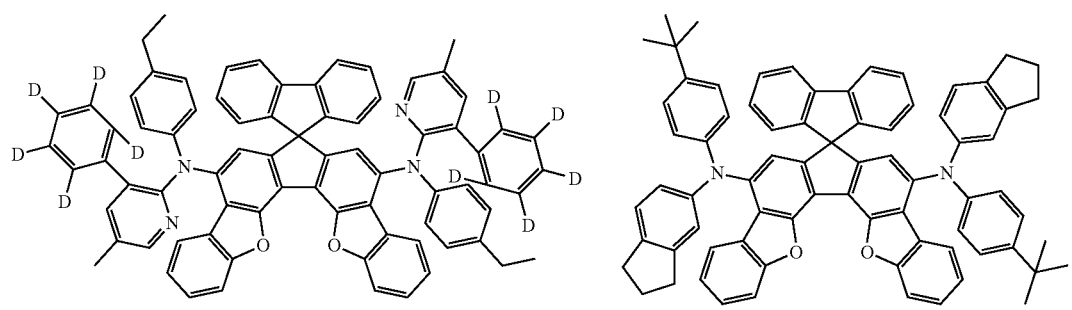

<Chemical Formula 31>
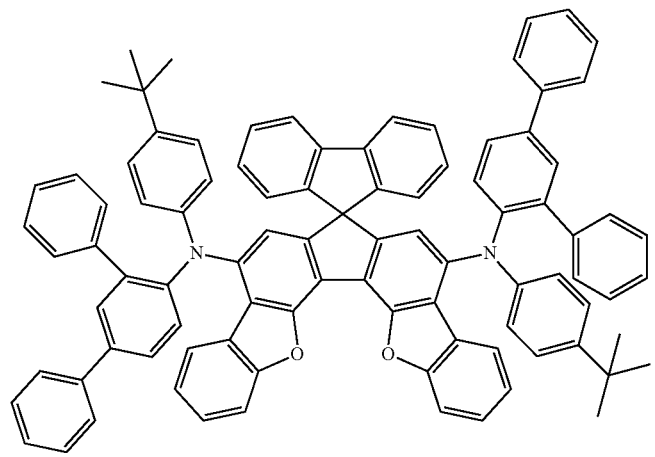
<Chemical Formula 32>
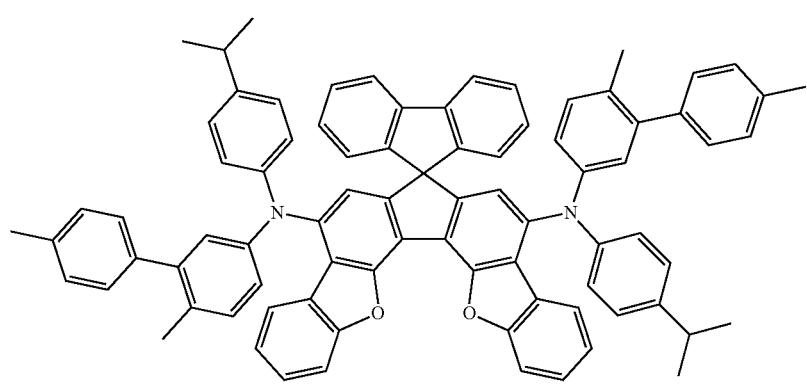
<Chemical Formula 85>
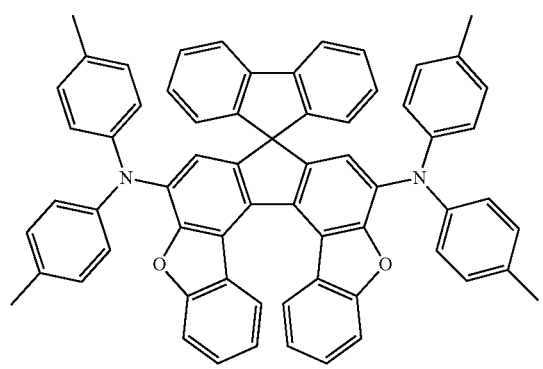
<Chemical Formula 91>
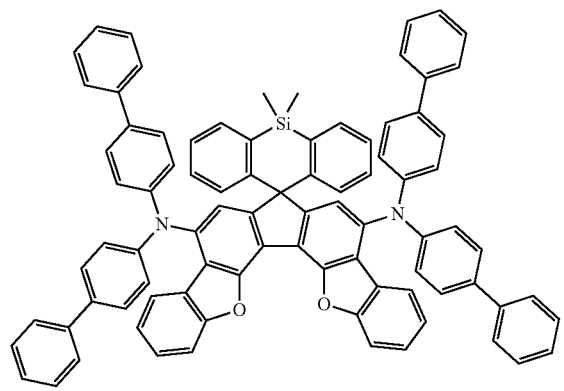

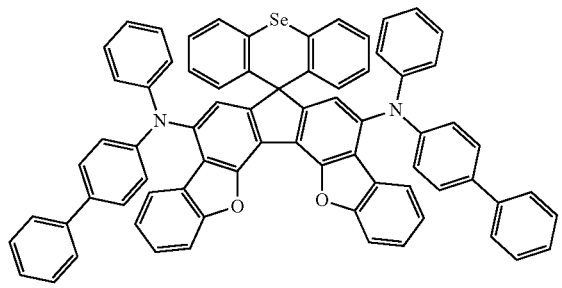
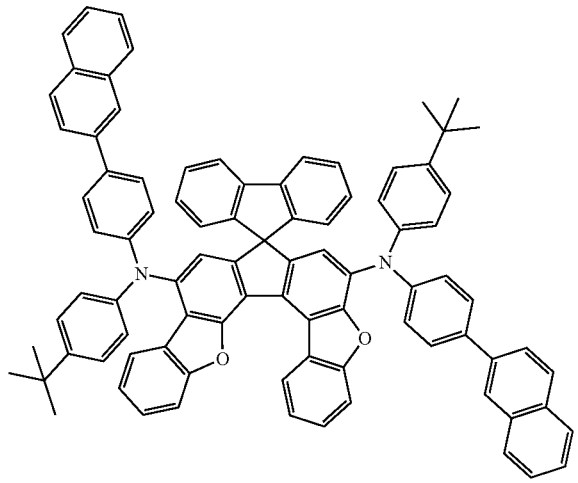
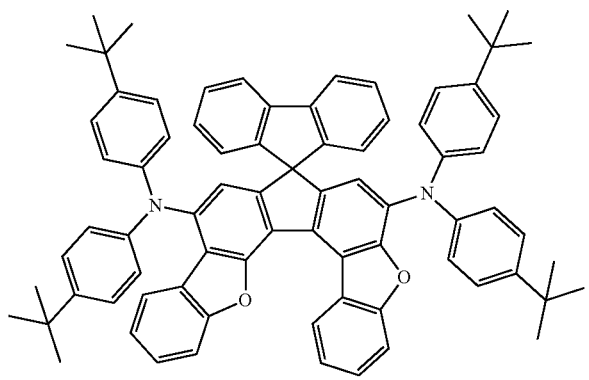
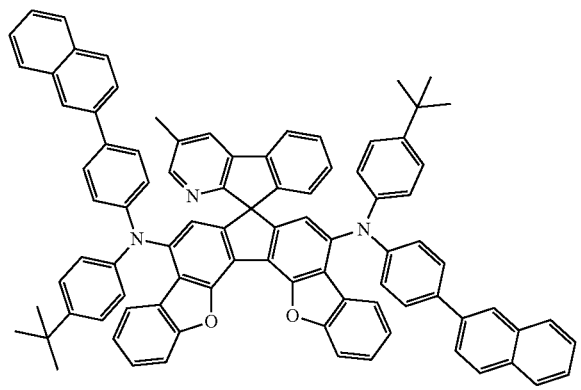

<Chemical Formula 117>
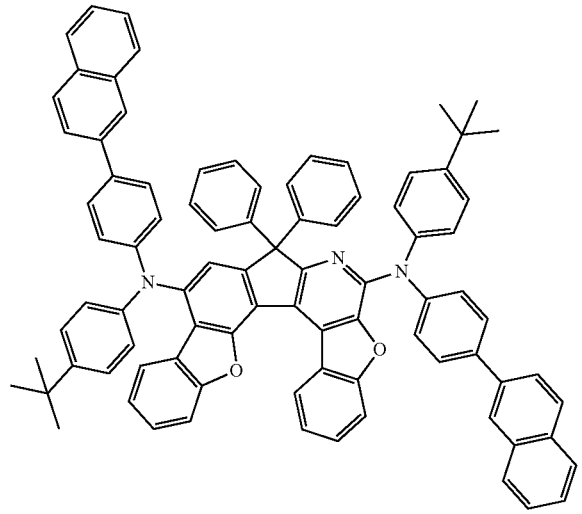
<Chemical Formula 142>
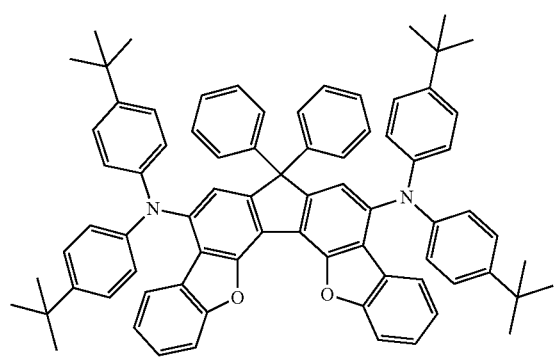
<Chemical Formula 143>
<Chemical Formula 144>
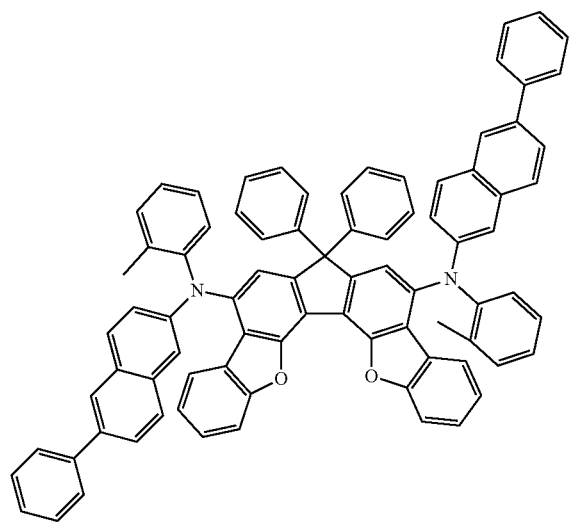
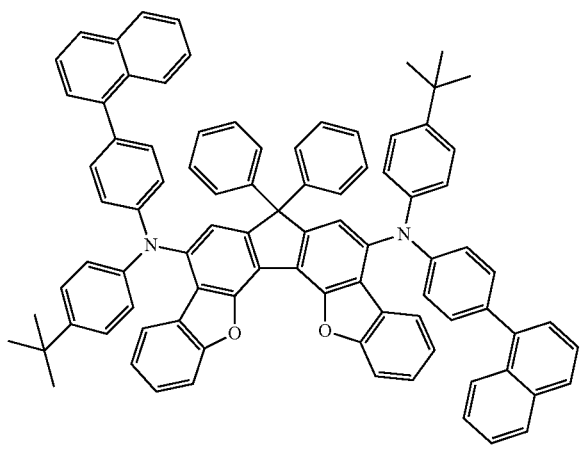

<Chemical Formula 145>
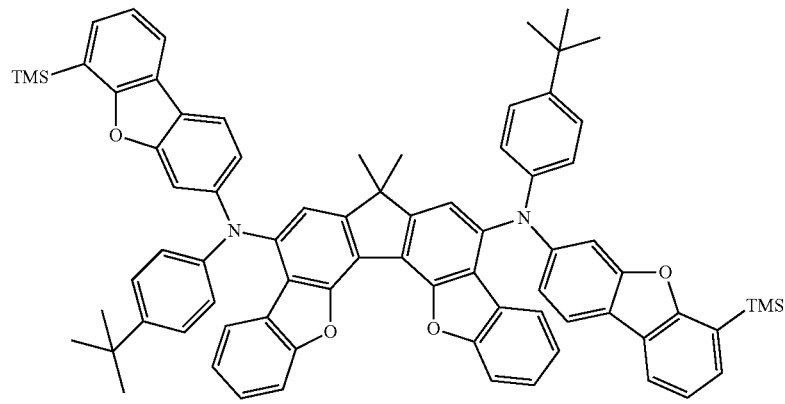
<Chemical Formula 146>
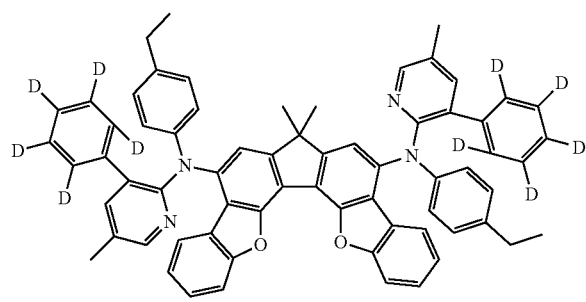
<Chemical Formula 147>
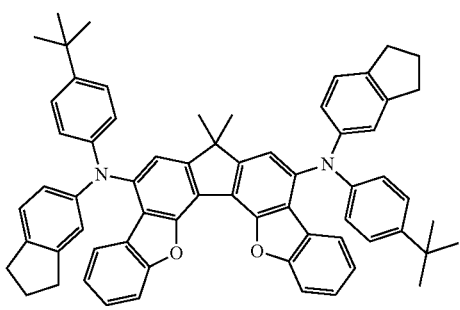
<Chemical Formula 148>
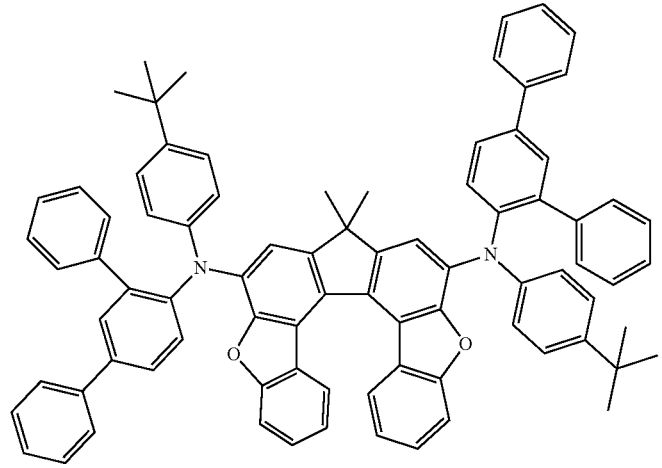
<Chemical Formula 149>
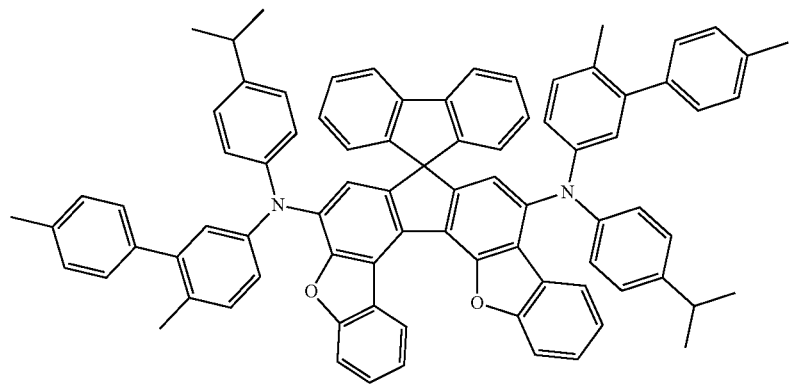

<Chemical Formula 160>
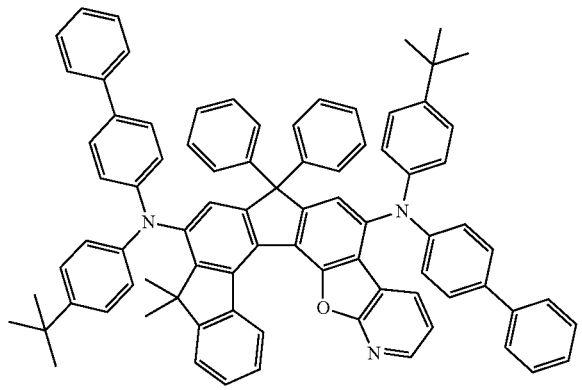
<Chemical Formula 162>
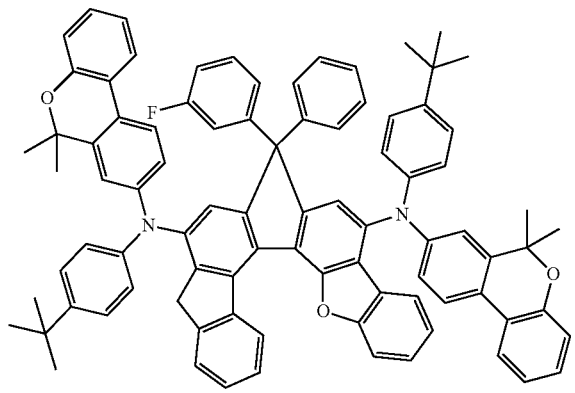
<Chemical Formula 164>
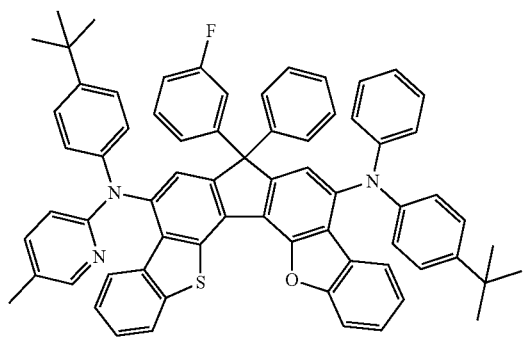
<Chemical Formula 165>
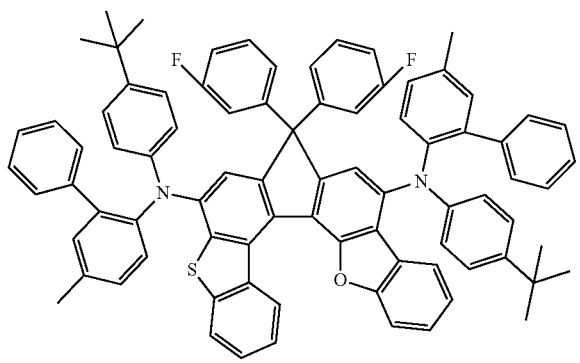

<Chemical Formula 197>
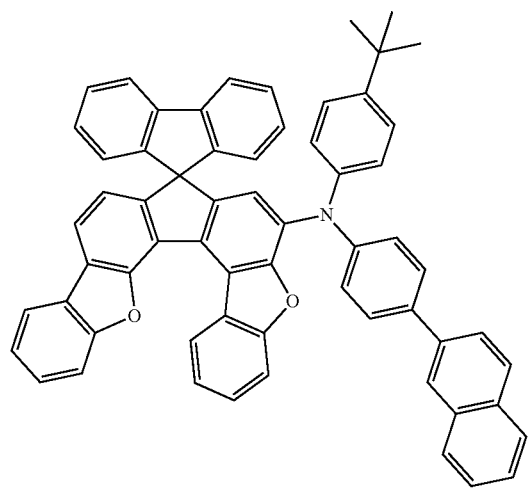
<Chemical Formula 198>
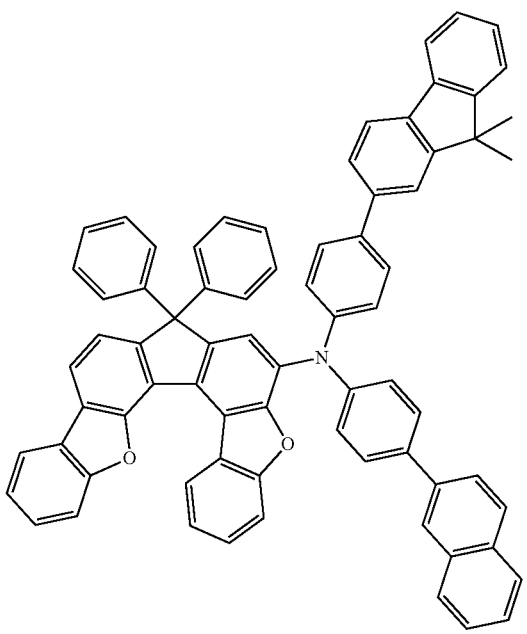
<Chemical Formula 199>
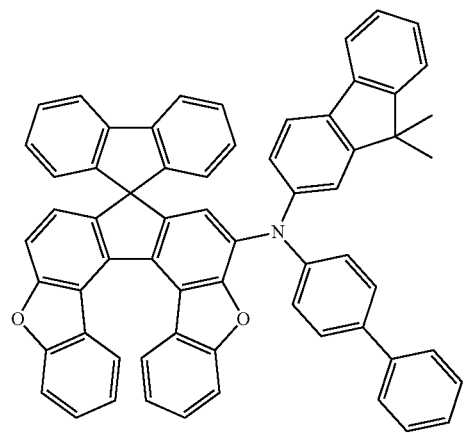
<Chemical Formula 200>
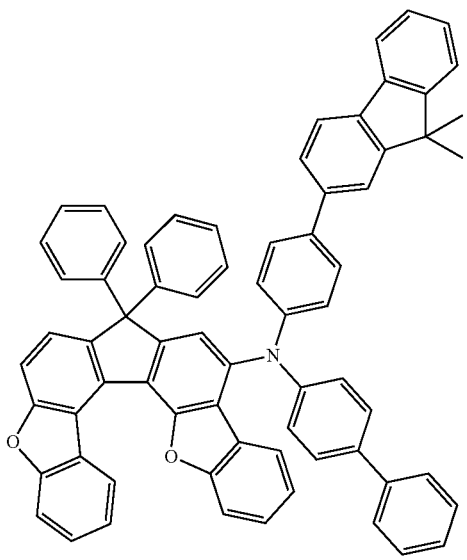

<Chemical Formula 201>
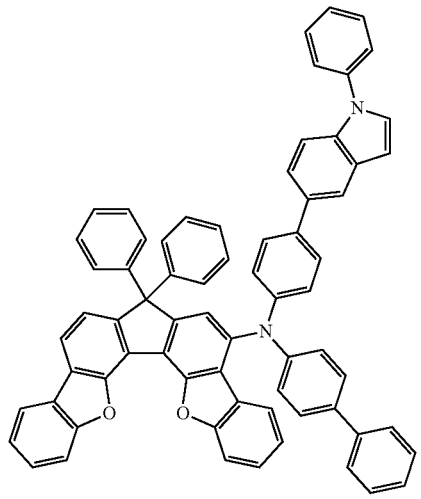
<Chemical Formula 210>
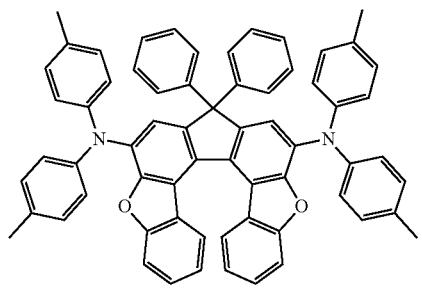
<Chemical Formula 222>
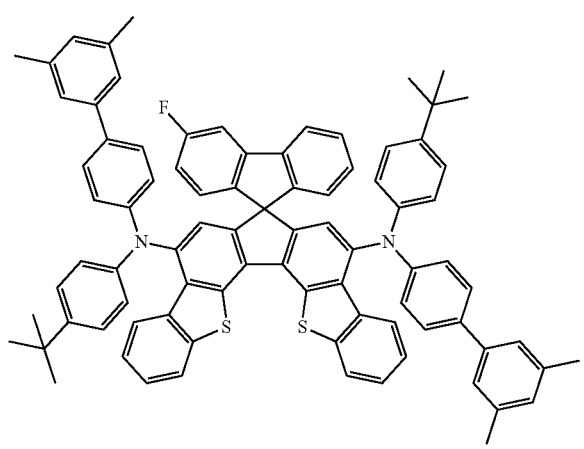
<Chemical Formula 223>
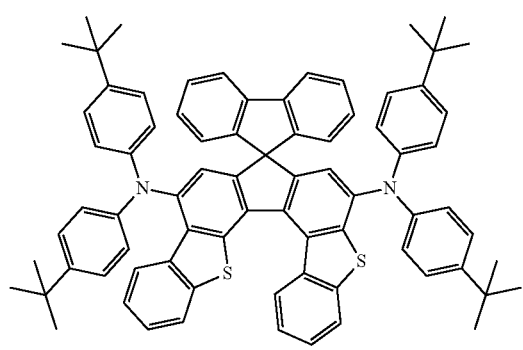
<Chemical Formula 224>
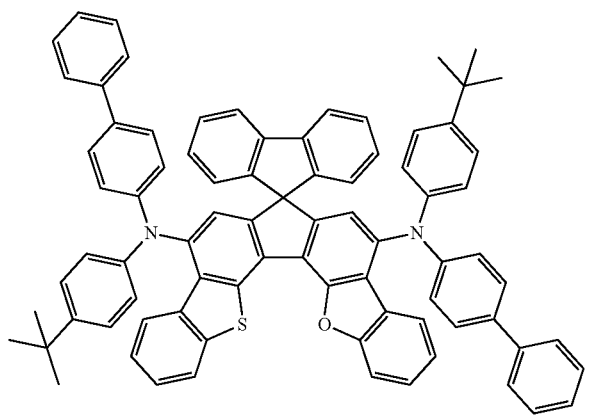

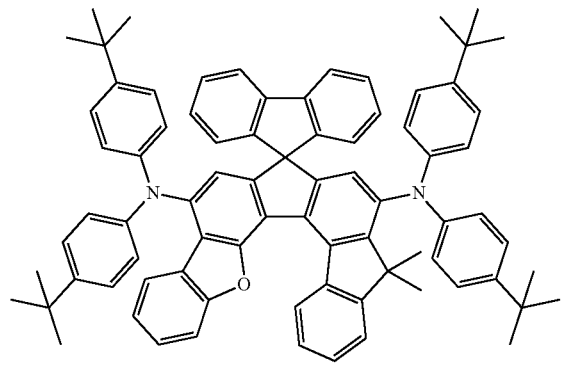
<Chemical Formula 227>
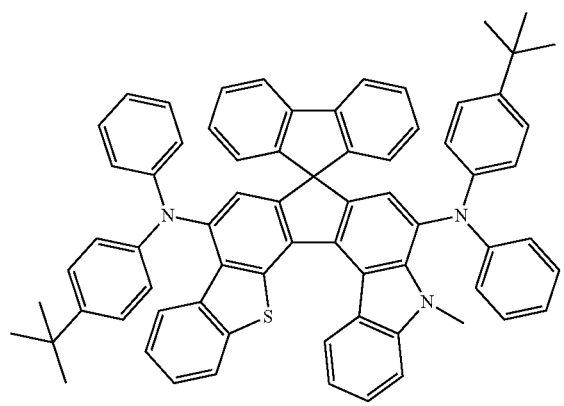
<Chemical Formula 228>
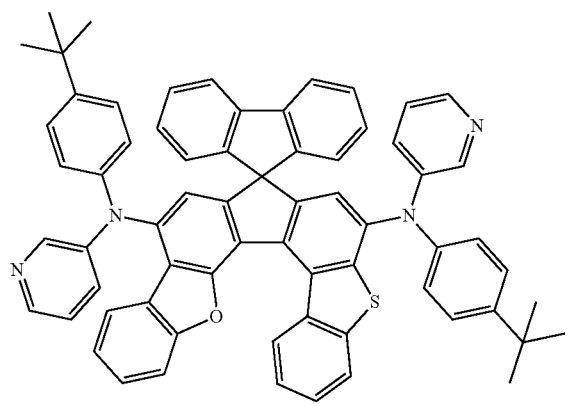
<Chemical Formula 229>
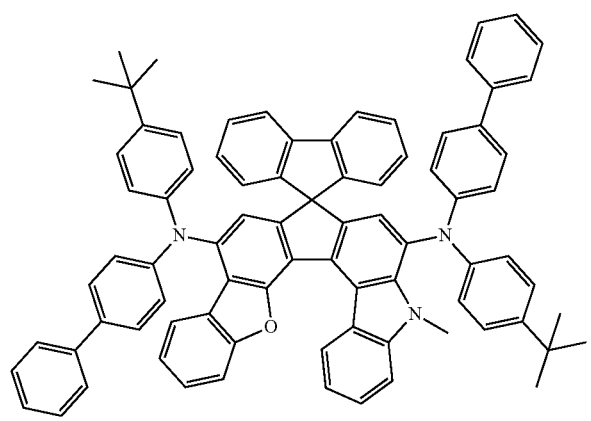
<Chemical Formula 230>
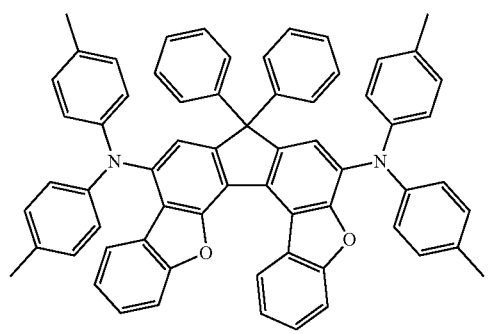
<Chemical Formula 231>

<Chemical Formula 239>
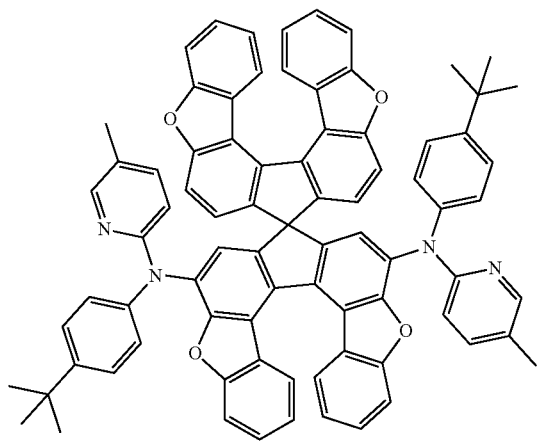
10. The organic light-emitting diode of claim 1, wherein the compound represented by Chemical Formula C is any one selected from among the following Compounds 1 to 48:
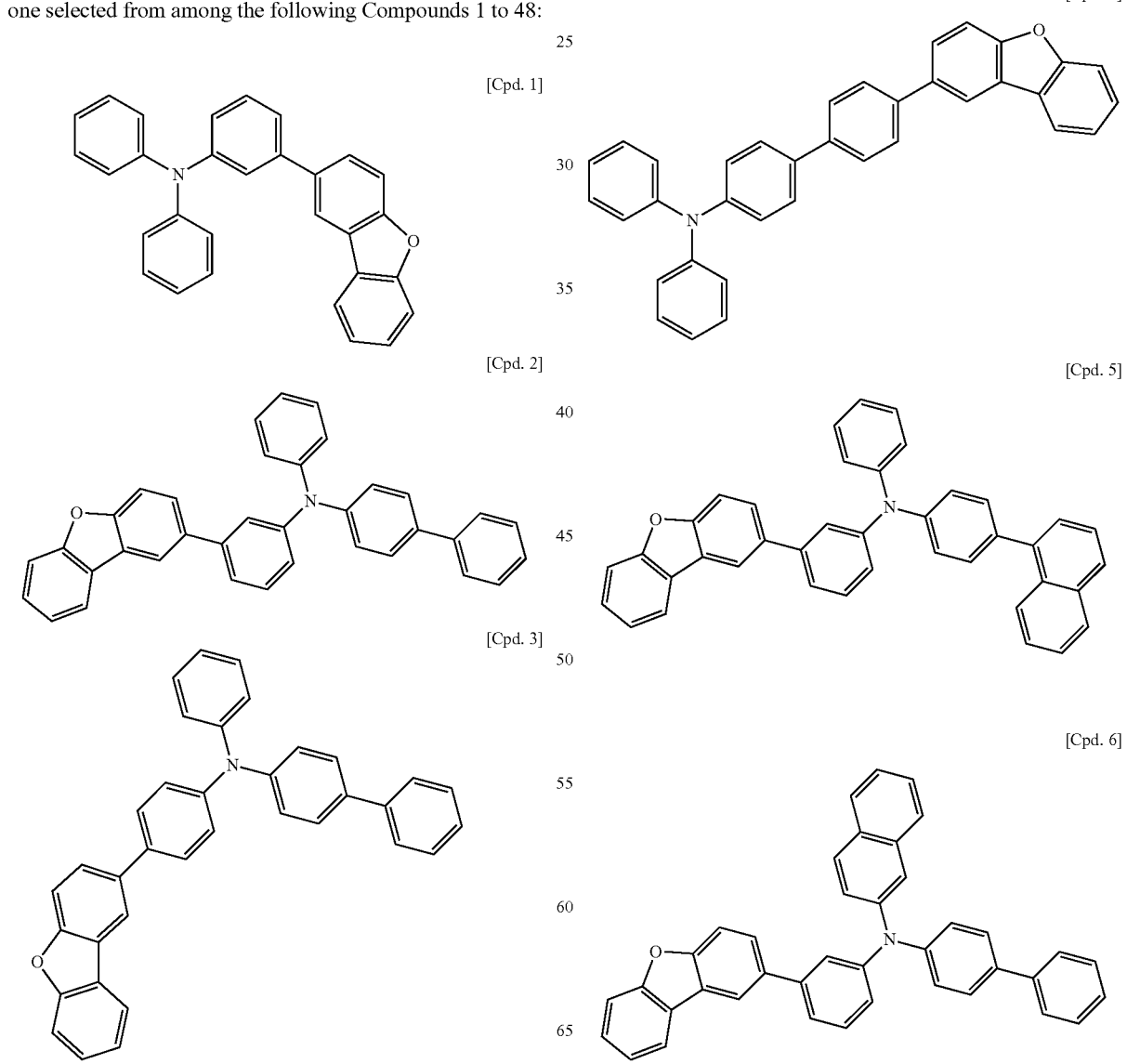

[Cpd. 7]
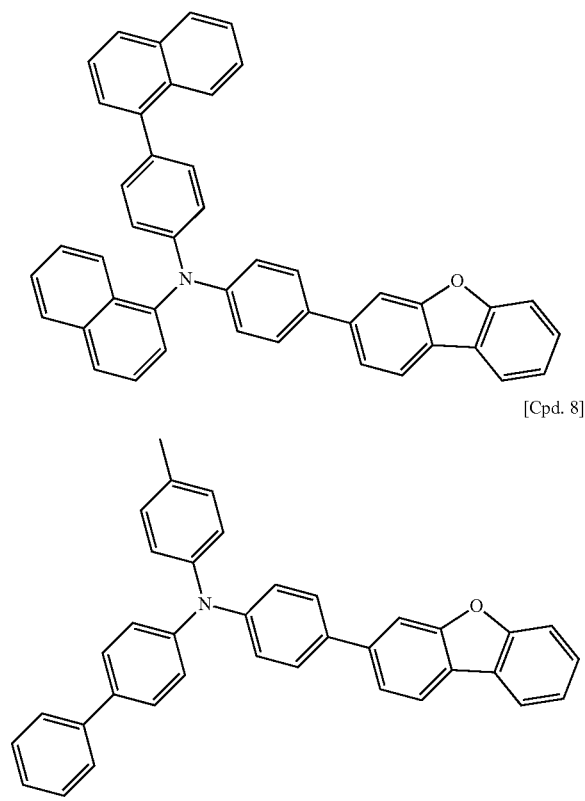
[Cpd. 8]
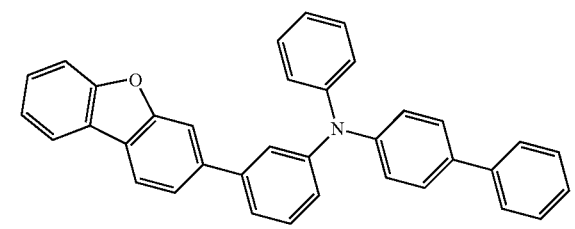
[Cpd. 9]
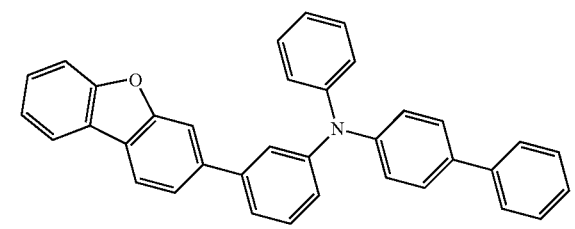
[Cpd. 10]
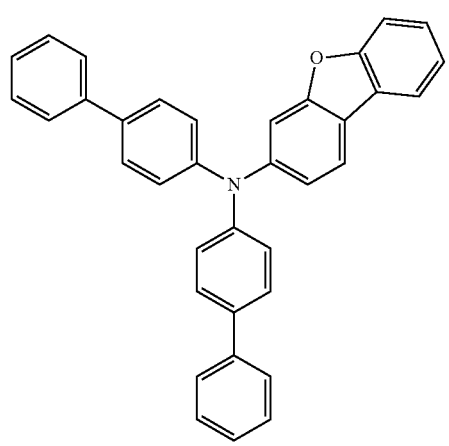
[Cpd. 11]
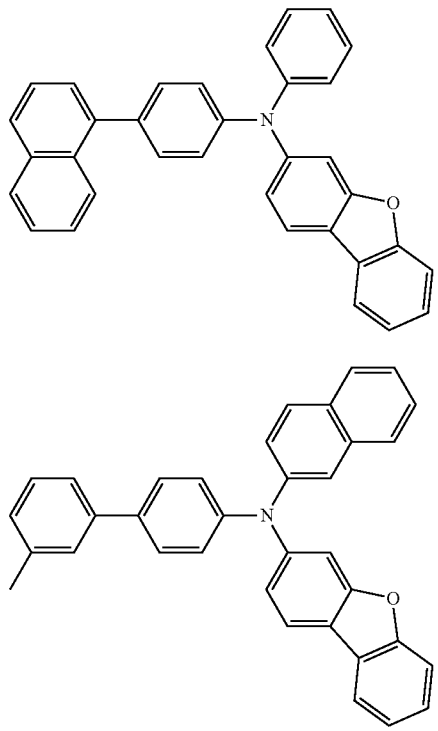
[Cpd. 12]
[Cpd. 13]
[Cpd. 14]
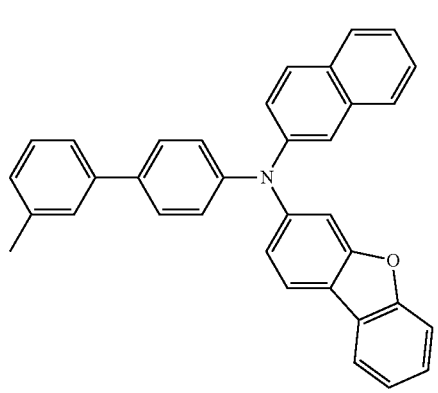

[Cpd. 15]
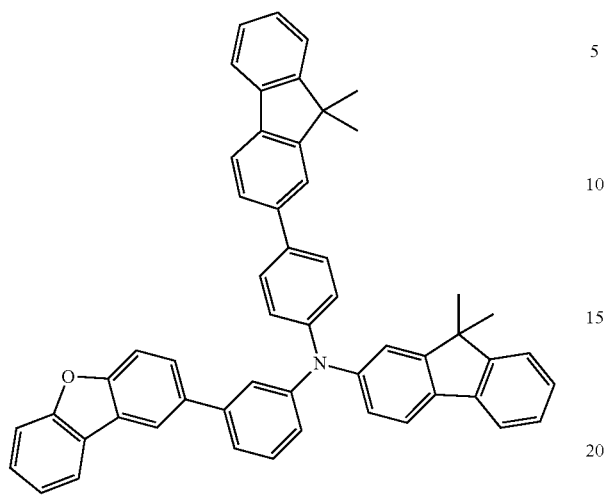
[Cpd. 16]
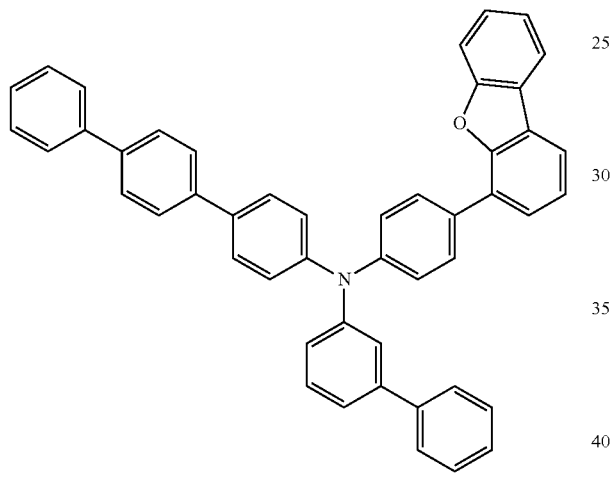
[Cpd. 17]
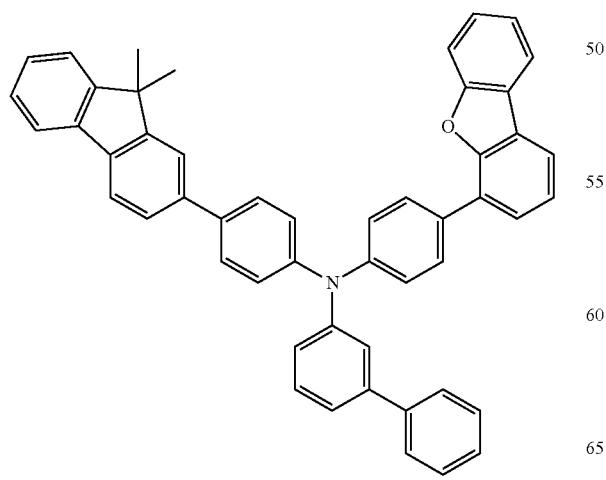
[Cpd. 18]
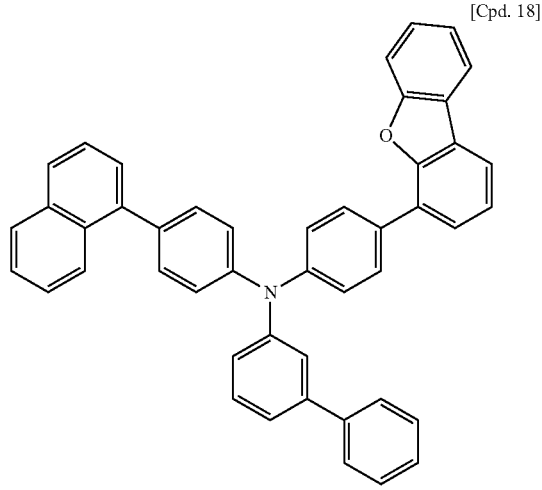
[Cpd. 19]
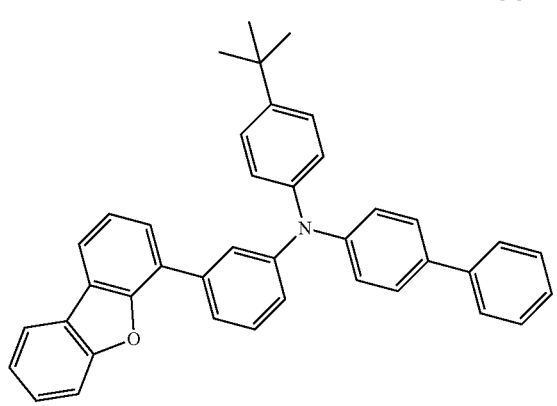
[Cpd. 20]

[Cpd. 21]
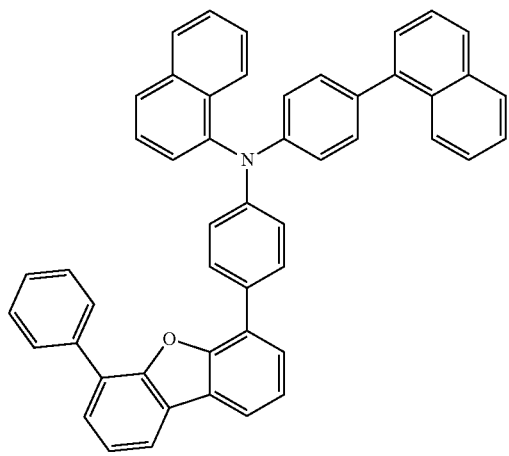
[Cpd. 24]
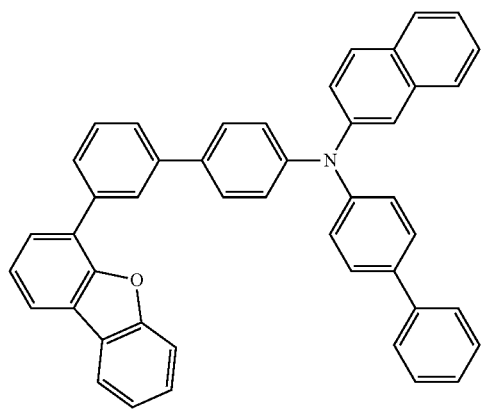
[Cpd. 22]
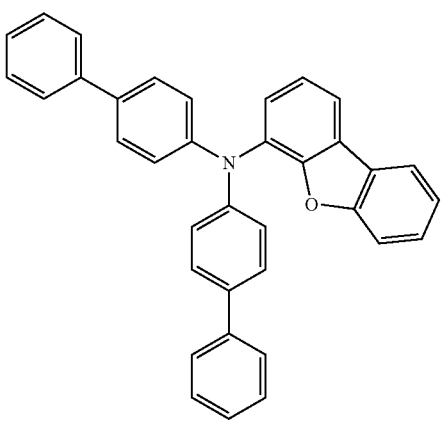
[Cpd. 25]
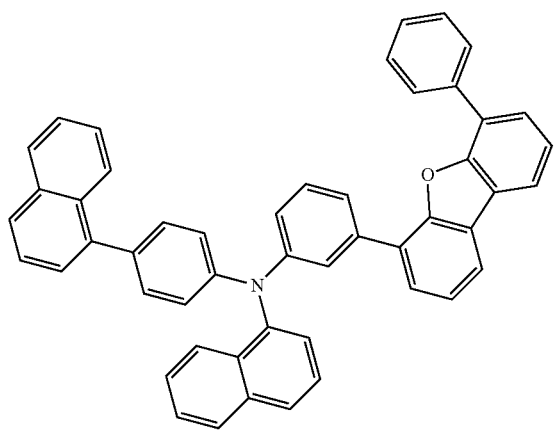
[Cpd. 23]
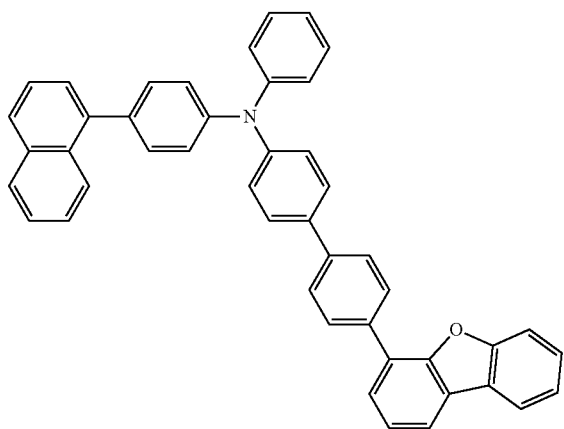
[Cpd. 26]
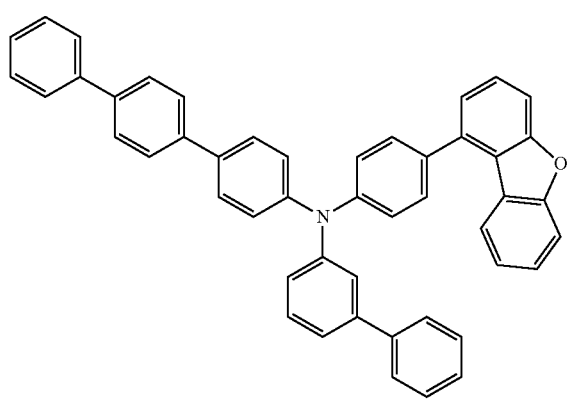

[Cpd. 27]
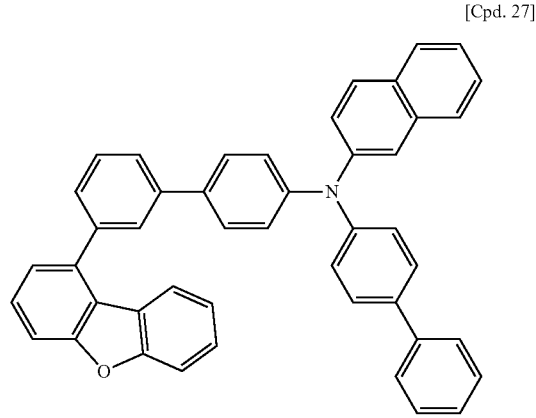
[Cpd. 28]
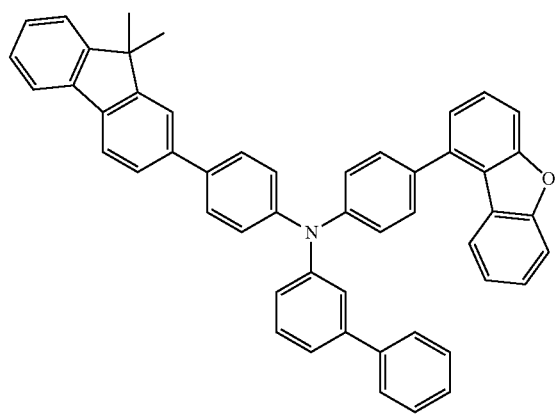
[Cpd. 29]
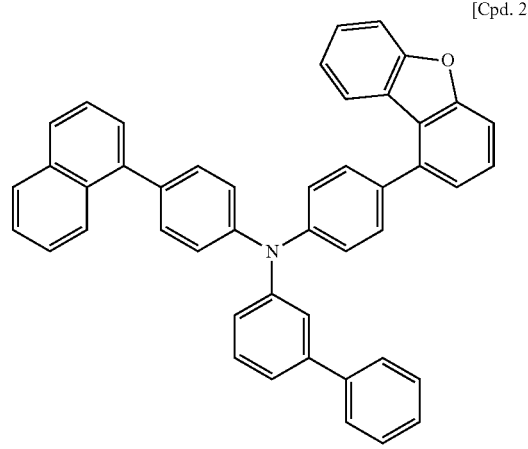
[Cpd. 30]
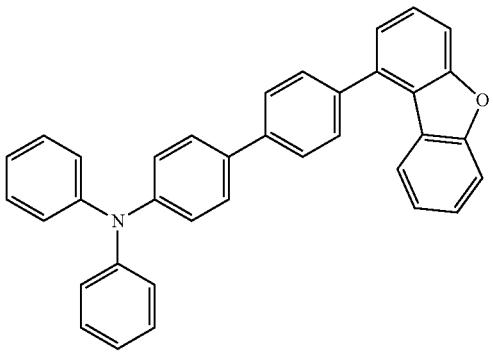
[Cpd. 31]
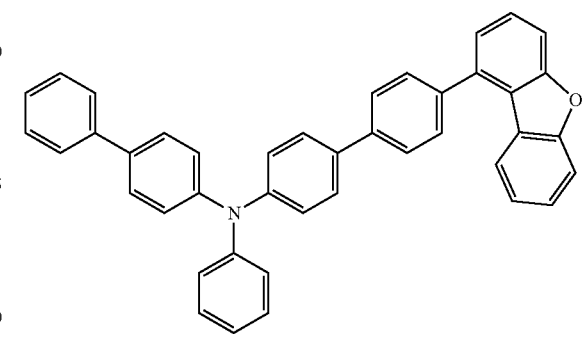
[Cpd. 32]
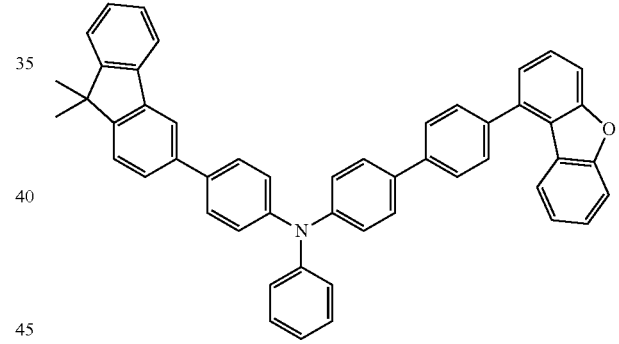
[Cpd. 33]
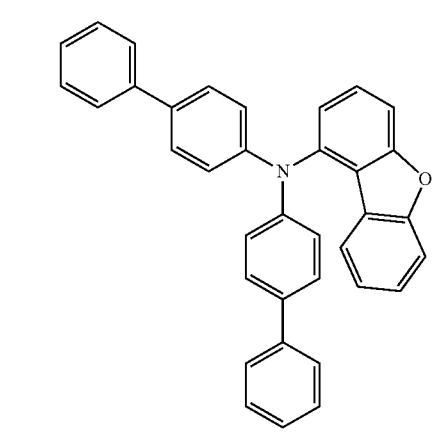

[Cpd. 34]
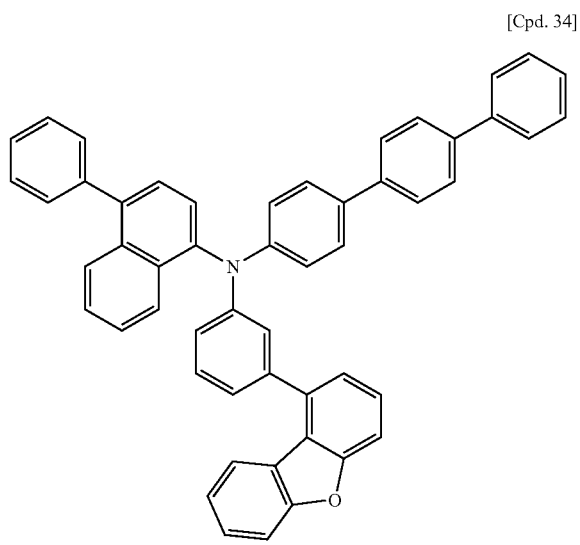
[Cpd. 37]
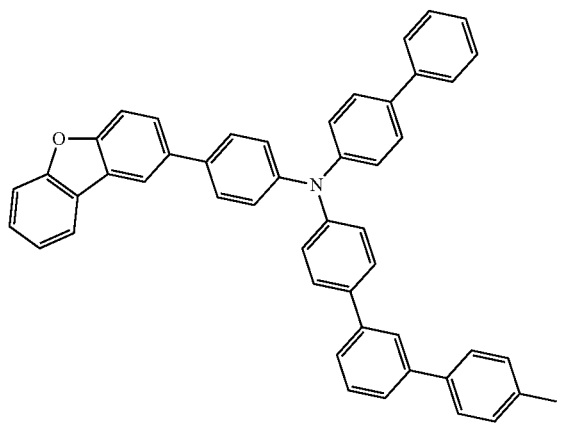
[Cpd. 35]
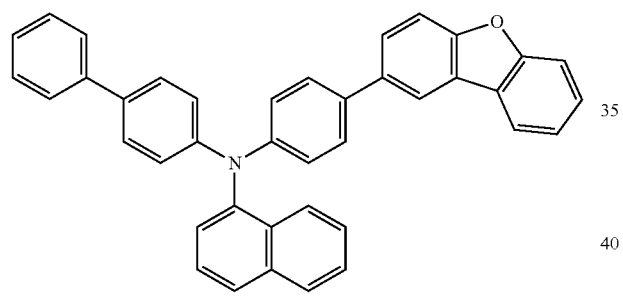
[Cpd. 38]
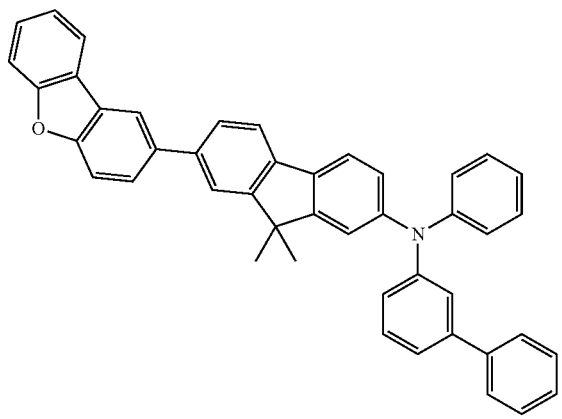
[Cpd. 36]
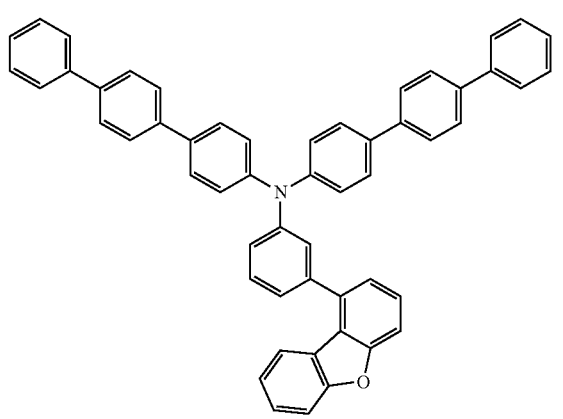
[Cpd. 39]
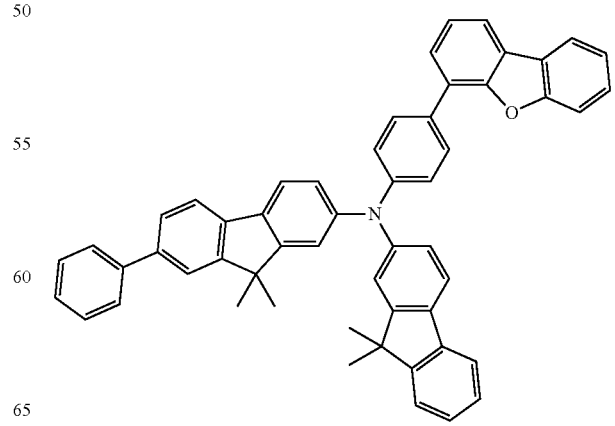

[Cpd. 40]
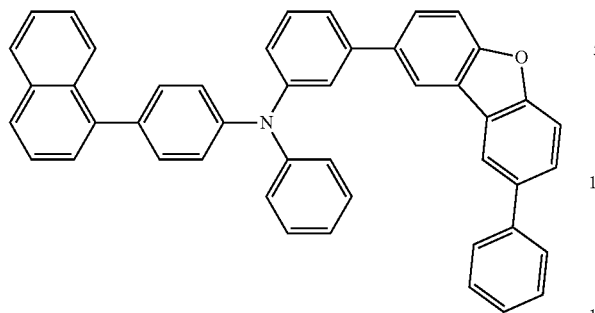
[Cpd. 43]
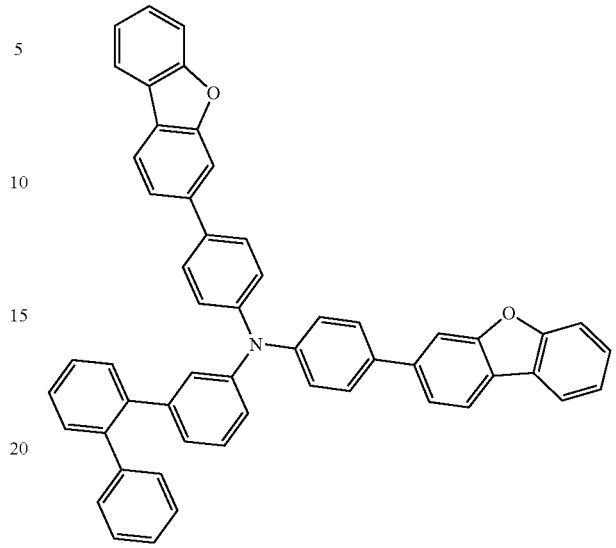
[Cpd. 41]
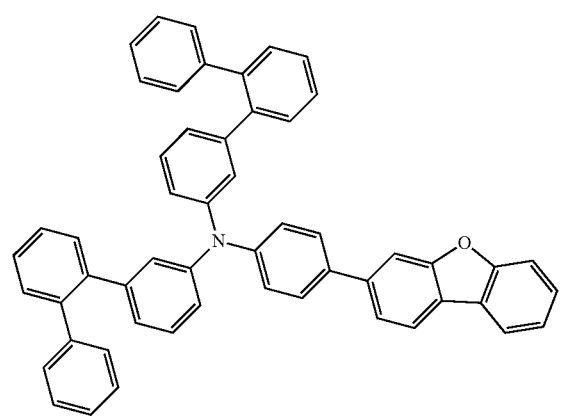
[Cpd. 44]
[Cpd. 42]
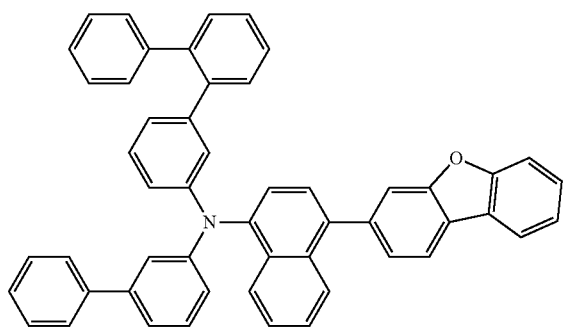
[Cpd. 45]
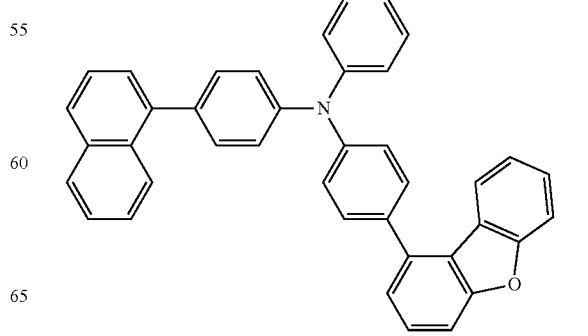

[Cpd. 46]

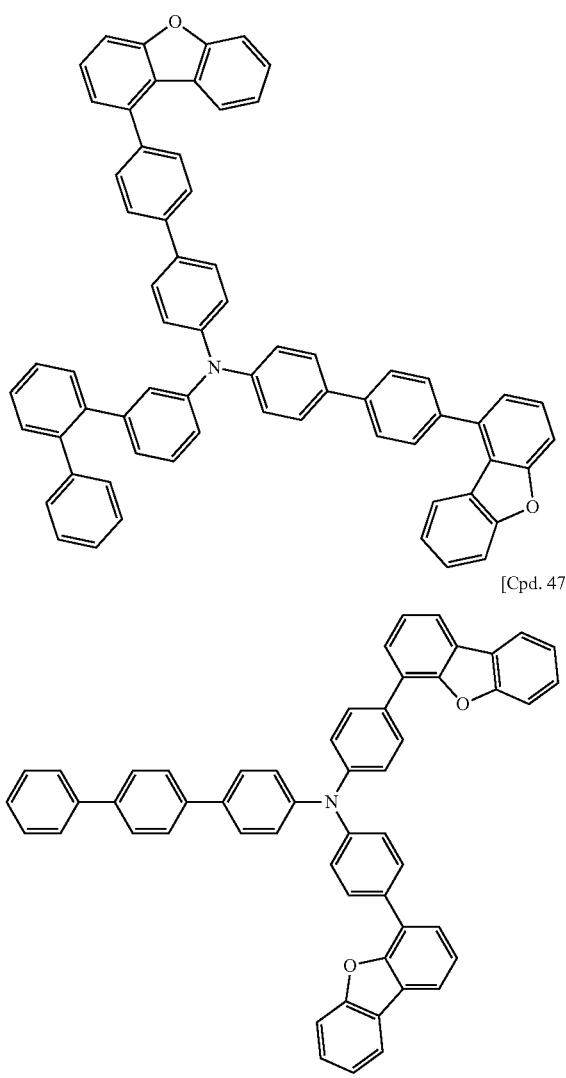

[Cpd. 47]

[Cpd. 48]

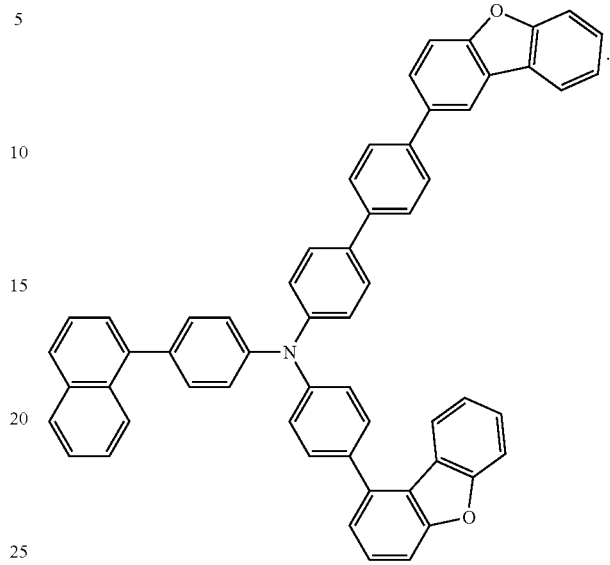

11. The organic light-emitting diode of claim 1, wherein the organic light-emitting diode comprises at least one of a hole injection layer, a hole transport layer, an electron transport layer, and an electron injection layer, in addition to the electron-blocking layer and the light-emitting layer.

12. The organic light-emitting diode of claim 11, wherein at least one of the layers is formed using a deposition process or a solution process.

13. The organic light-emitting diode of claim 1, wherein organic light-emitting diode is used for a device selected from among a flat display device, a flexible display device, a monochrome or white flat illumination device, and a monochrome or white flexible illumination device.

* * * * *